(12) United States Patent
Chodosh et al.

(10) Patent No.: US 7,119,185 B2
(45) Date of Patent: Oct. 10, 2006

(54) HORMONALLY UP-REGULATED, NEU-TUMOR-ASSOCIATED KINASE

(75) Inventors: Lewis A. Chodosh, West Chester, PA (US); Heather P. Gardner, Palo Alto, CA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 580 days.

(21) Appl. No.: 10/032,256

(22) Filed: Dec. 21, 2001

(65) Prior Publication Data

US 2005/0186668 A1 Aug. 25, 2005

Related U.S. Application Data

(60) Provisional application No. 60/257,073, filed on Dec. 21, 2000.

(51) Int. Cl.
*C07H 21/02* (2006.01)
*C07H 21/04* (2006.01)

(52) U.S. Cl. ...................... 536/23.1; 536/23.2; 536/23.5
(58) Field of Classification Search ................ 536/23.1, 536/23.2, 23.5
See application file for complete search history.

(56) References Cited

PUBLICATIONS

Gardner et al. (Genomics 2000, 64, 46–59).*
NCBI database for nucleotides (Accession No.: AF055919, Apr. 28, 1999, See attached comparison).*
Alberts et al. (Molecular Biology of the Cell, see attached).*
Naylor, L.H. (Biochemical Pharmacology 1999, 58:749–757).*
Aasheim, H.C., Terstappen, L. W., and Logtenberg, T. "Regulated expression of the Eph–related receptor tyrosine kinase Hek11 in early human B lymphopoiesis." *Blood* 90: 3613–3622 (1997).
Adams, R. H., Wilkinson, G. A., Weiss, C., Diella, F., Gale, N. W., Deutsch, U., Risau, W., and Klein, R. "Roles of ephrinB ligands and EphB receptors in cardiovascular development: De–marcation of arterial/venous domains, vascular morphogenesis, and sprouting angiogenesis." *Genes Dev.* 13: 295–306 (1999).
Adnane, J., Gaudray, P., Dionne, C. A., Crumley, G., Jaye, M., Schlessinger, J., Jeanteur, P., Birnbaum, D., and Theillet, C. "BEK and FLG, two receptors to members of the FGF family, are amplified in subsets of human breast cancers," *Oncogene* 6:659–663 (1991).
Alderson, A., Sabelli, P., Dickinson, J., Cole, D., Richardson, M., Kreis, M., Shewry, P., and Halford, N. "Complementation of snf1, a mutation affecting global regulation of carbon metabolism in yeast, by a plant protein kinase cDNA," *Proc. Natl. Acad. Sci. USA* 88: 8602–8605 (1991).

Andres, A.–C., Zuercher, G., Djonov, V., Flueck, M., and Ziemiecki, A. "Protein tyrosine kinase expression during the estrous cycle and carcinogenesis of the mammary gland." *Int. J. Cancer* 63: 288–296 (1995).
Becker, W., Heukelbach, J., Kentrup, H., and Joost, H. G. "Molecular cloning and characterization of a novel mammalian protein kinase harboring a homology domain that defines a sub–family of serine/threonine kinases." *Eur. J. Biochem.* 235: 736–743 (1996).
Bergemann, A. D., Zhang, L., Chiang, M. K., Brambilla, R., Klein, R., and Flanagan, J. G. "Ephrin–B3, a ligand for the receptor EphB3, expressed at the midline of the developing neural tube," *Oncogene* 16:471–480 (1998).
Bessone, S., Vidal, F., Le Bouc, Y., Epelbaum, J., Bluet–Pajot, M. T. and Darmon, M., "EMK protein kinase–null mice: dwarfism and hypofertility associated with alternations in the somatotrope and prolactin pathways." *Dev. Biol.* 214: 87–101 (1999).
Betzl, G., Brem, G. and Weidle, U. H. "Epigenetic modification of transgenes under the control of the mouse mammary tumor virus LTR: tissue–dependent influence on transcription of the transgenes," *Biol. Chem.* 377: 771–719 (1996).
Bishop, D. F., Calhoun, D. H., Bernstein, H. S., Hantzopoulos, P., Quinn, M., and Desnick, R. J. "Human alpha–galactosidase A: Nucleotide sequence of a cDNA clone encoding the mature enzyme." *Proc. Natl. Acad. Sci. USA* 83: 4859–4863 (1986).
Bocchinfuso, W.P. and Korach, K.S. "Mammary gland development and tumorigenesis in estrogen receptor knock-out mice." *J. Mamm. Gland Biol. Neoplasia* 2: 323–334 (1997).
Bohm, H., Brinkmann, V., Drab, M., Henske, A., and Kurzchalia, T.V. "Mammalian homologues of *C. elegans* PAR–1 are asymmetrically localized in epithelial cells and may influence their polarity." *Curr. Biol.* 7: 603–606 (1997).

(Continued)

*Primary Examiner*—Jeffrey Siew
*Assistant Examiner*—Brandon Fetterolf
(74) *Attorney, Agent, or Firm*—Evelyn H. McConathy, Es; Drinker, Biddle & Reath

(57) ABSTRACT

This invention relates generally to a novel serine/threonine protein kinase, specifically to hormonally up-regulated, neu-tumor-associated kinase (HUNK); and to the nucleotide sequence encoding it. The kinase is temporally expressed during postnatal mammary development in a spatially heterogeneous manner in certain subsets of cells, and overexpressed in a subset of primary breast cancers. The invention further relates to an analysis of a correlation between carcinogenesis and postnatal development, particularly mammary development, especially associated with parity; to methods of using the kinase, or gene encoding it, as markers, prognostic tools, screening tools and therapies, in vitro and in vivo, that are based upon that correlation; and to the regulation of pregnancy-induced changes in the mammary tissue that occur in response to estrogen and progesterone.

7 Claims, 16 Drawing Sheets

PUBLICATIONS

Brinkley, P. M., Class, K., Bolen, J. B., and Penhallow, R. C. "Structure and developmental regulation of the murine ctk gene." *Gene* 163: 179–184 (1995).

Buhler, T. A., Dale, T. C., Kieback, C., Humphreys, R. C. and Rosen, J. M. "Localization and quantification of Wnt–2 gene expression in mouse mammary development." *Dev. Biol.* 155: 87–96 (1993).

Cance, W. G. Craven, R. J., Weiner, T. M., and Liu, E. T. "Novel protein kinases expressed in human breast cancer." *Int. J. Cancer* 54: 571–577 (1993).

Cardiff, R. D., and Muller, W. J. "Transgenic mouse models of mammary tumorigenesis." *Cancer Surv.* 16: 97–113 (1993).

Cardiff, R. D., Sinn, E., Muller, W., and Leder, P. "Transgenic oncogene mice. Tumor phenotype predicts genotype." *Am. J. Pathol.* 139: 495–501 (1991).

Carling, D., Aguan, K., Woods, A., Verhoeven, A. J., Beri, R. K., Brennan, C. H., Sidebottom, C., Davison, M. D., and Scott, J. "Mammalian AMP–activated protein kinase is homologous to yeast and plant protein kinases involved in the regulation of carbon metabolism." *J. Biol. Chem.* 269: 11442–11448 (1994).

Carlson, M., Osmond, B., and Botstein, D. "Mutants of yeast defective in sucrose utilization." *Genetics* 98: 25–40 (1981).

Celenza, J. L., Eng, F. J., and Carlson, M. "Molecular analysis f the SNF4 gene of *Saccharomyces cerevisiae*: Evidence for physical association of the SNF4 protein with the SNF1 protein kinase." *Mol. Cell. Biol.* 9: 5045–5054 (1989).

Cho, R. J., Campbell, M. J., Winzeler, E. A., Steinmetz, L., Conway, A., Wodicka, L., Wolfsberg, T. G., Gabrielian, A. E., Landsman, D., Lockhart, D. J., and Davis, R. W. "A genome–wide transcriptional analysis of the mitotic cell cycle." *Mol. Cell* 2: 65–73 (1998).

Chodosh, L. A., D'Cruz, C. M., Gardner, H. P., Ha, S. I., Marquis, S. T., Rajan, J. V., Stairs, D. B., Wang, J. Y., and Wang, M. "Mammary gland development, reproductive history, and breast cancer risk." *Cancer Res.* 59: 1765–1771S (1999).

Chodosh, L. A., Gardner, H. P., Rajan, J. V., Stairs, D. B., Marquis, S. T., and Leder, P. A. "Protein kinase expression during murine mammary development." *Dev. Biol.* 219: 259–276, (2000).

Ciriacy, M. "Isolation and characterization of yeast mutants defective in intermediary carbon metabolism and in carbon catabolite repression." *Mol. Gen. Genet.* 154: 213–220 (1977).

Copeland, N. G., and Jenkins, N. A. "Development and applications of a molecular genetic linkage map of the mouse genome." *Trends Genet.* 7: 113–118 (1991).

Delabar, J. M., Theophile D., Rahmani, Z., Chettah, Z., Blouin, J. L., Prieur, M., Noel, B., and Sinet, P. M., "Molecular mapping of twenty–four features of Down syndrome on chromosome 21." *Eur. J. Hum. Genet.* 1: 114–124 (1993).

Di Fiore, P., Pierce, J. H., Fleming, T. P., Hazan, R., Ullrich, A., King, C. R., Schlessinger, J. and Aaronson, S. A. "Overexpression of the human EGF receptor confers an EGF–dependent transformed phenotype to NIH 3T3 cells." *Cell* 51: 1063–1070 (1990).

Drewes, G., Ebneth, A., Preuss, U., Mandelkow, E. M., and Man–delkow, E. "MARK, a novel family of protein kinases that phosphorylate microtubule–associated proteins and trigger micro–tubule disruption." *Cell* 89: 297–308 (1997).

Dymecki, S. M., Niederhuber, J. E., and Desiderio, S. V. "Specific expression of a tyrosine kinase gene, blk, in B lymphoid cells." *Science* 247: 332–336 (1990).

Elson, A., and Leder, P. "Protein–tyrosine phosphatase epsilon. An isoform specifically expressed in mouse mammary tumors initiated by v–Ha–ras or neu." *J. Biol. Chem.* 270: 2611–26122 (1995).

Fan, C. M., Kuwana, E., Bulfone, A., Fletcher, C. F., Copeland, N. G.,Jenkins N. A., Crews, S., Martinez, S., Puelles, L., Rubenstein, L. R., and Tessier–Lavigne, M. "Expression patterns of two murine homologs of Drosophila single–minded suggest possible roles in embryonic patterning and in the pathogenesis of Down syndrome." *Mol. Cell. Neurosci.* 7: 519 (1996).

Ferrari, S., Manfredini, R., Tagliafico, E., Grande, A., Barbieri, D., Balestri, R., Pizzanelli, M., Zucchini, P., Citro, G., Zupi, G., et al. "Antiapoptotic effect of c–fes protooncogene during granu–locytic differentiation." *Leukemia* 8: S91–94 (1994).

Fields, S., and Song, O. "A novel genetic system to detect protein–protein interactions." *Nature* 340: 245–246 (1989).

Fox, G. M., Holst, P. L., Chute, H. T., Lindberg, R. A., Janssen, A. M., Basu, R., and Welcher, A. A. "cDNA cloning and tissue distribution of five human EPH–like receptor protein–tyrosine kinases." *Oncogene* 10: 897–905 (1995).

Ganju, P., Walls, E., Brennan, J., and Reith, A. D. "Cloning and developmental expression of N5k2, a novel receptor tyrosine kinase implicated in skeletal myogenesis." *Oncogene* 11: 281–290 (1995).

Gavin, B. J. and McMahon, A. P. "Differential regulation of the Wnt gene family during pregnancy and lactation suggests a role in postnatal development of the mammary gland." *Mol. Cell. Biol.* 12: 2418–2423 (1992).

Guo, S. and Kemphues, K. "par–1, a gene required for establishing polarity in *C. elegans* embryos, encodes a putative ser/thr kinase that is asymmetrically distributed." *Cell* 81: 611–620 (1995).

Guy, C. T., Muthuswamy, S. K., Cardiff, R. D., Soriano, P., and Muller, W. J. "Activation of the c–Src tyrosine kinase is required for the induction of mammary tumors in transgenic mice." *Genes Dev.* 8: 23–32 (1994).

Hanks, S. K., Quinn, A. M., and Hunter, T. "The protein kinase family: Conserved features and deduced phylogeny of the catalytic domains." *Science* 241: 42–52 (1988).

Hanks, S., and Quinn, A. "Protein kinase catalytic domain sequence database: Identification of conserved features of primary structure and classification of family members." *Methods Enzymol.* 200: 38–79 (1991).

Hardie, D. G. "Roles of the AMP–activated/SNF1 protein kinase family in the response to cellular stress." *Biochem. Soc. Symp.* 64: 13–27 (1999).

Hardie, D. G., Carling, D. and Halford, N. "Roles ofth Snf1/Rkin1/AMP–activated protein kinase family in the response to environmental and nutritional stress." *Semin. Cell Biol.* 5: 409–416 (1994).

Hardie, D. G., Corton, J., Ching, Y. P., Davies, S. P., and Hawley, S. "Regulation of lipid metabolism by the AMP–activated protein kinase." *Biochem. Soc. Trans.* 25: 1229–1231 (1997).

Hardie, D. G., Salt, I. P., Hawley, S. A., and Davies, S. P. "AMP–activated protein kinase: An ultrasensitive system for monitoring cellular energy charge." *Biochem. J.* 338: 717–722 (1999).

Henderson, B. E., Ross, R. K. and Bernstein, L. "Estrogens as a cause of human cancer: the Richard and Hinda Rosenthal Foundation Award Lecture." *Cancer Res* 48: 246–253 (1988).

Herve, D., Rogard, M., and Levi–Strauss, M. "Molecular analysis of the multiple Golf alpha subunit mRNAs in the rat brain." *Brain Res. Mol. Brain Res.* 32: 125–134 (1995).

Heyer, B. S., Warsowe, J., Solter, D., Knowles, B. B., and Ackerman, S. L. "New member of the Snf1/AMPK kinase family, Melk, is expressed in the mouse egg and preimplantation embryo." *Mol. Reprod. Dev.* 47: 148–156 (1997).

Huang, A. L., Ostrowski, M. C., Berard, D. and Hager, G. L. "Glucocorticoid regulation of the Ha–MuSV p21 gene conferred by sequences from mouse mammary tumor virus." *Cell* 27: 245–255 (1981).

Humphreys, R. C., Lydon, J. P., O'Malley, B. W. and Rosen, J. M. "Use of PRKO mice to study the role of progesterone in mammary gland development." *J. Mamm. Gland Biol. Neoplasia* 2: 343–354 (1997).

Itoh, N., Mima, T., and Mikawa, T. "Loss of fibroblast growth factor receptors is necessay for terminal differentiation of embryonic limb muscle." *Development* 122: 291–300 (1996).

Jenkins, N. A., Copeland, N. G., Taylor, B. A., and Lee, B. K. "Organization, distribution, and stability of endogenous ecotropic murine leukemia virus DNA sequences in chromosomes of Musmusculus." *J. Virol.* 43: 26 (1982)

Jin, L., Fuchs, A., Schnitt, S. J., Yao, Y., Joseph, A., Lamszus, K., Park, M., Goldberg, I. D., and Rosen, E. M. "Expression of scatter factor and c–met receptor in benign and malignant breast tissue." *Cancer* 79: 749–760 (1997).

Kelsey, J. L., Gammon, M. D. and John, E. M. "Reproductive factors and breast cancer." *Epidemiol. Rev.* 15: 36–47 (1993).

Klijin, J., Berns, E., and Foekens, J. "Prognostic factors and response to therapy in breast cancer." In "Breast Cancer" (I. Fentiman and J. Taylor–Papadimitriou, Eds.) 18: 165–198. *Cold Spring Harbor Laboratory Press,* Cold Spring Harbor, NY. (1993).

Kluppel, M., Donoviel, D. B., Brunkow, M. E., Motro, B., and Bernstein, A. "Embryonic and adult expression patterns of the Tec tyrosine kinase gene suggest a role megakaryocytopoiesis, blood vessel development, and melanogenesis." *Cell Growth Differ.* 8: 1249–1256 (1997).

Korenberg, J. R., Chen, X. N., Schipper, R., Sun, Z., Gonsky, R., Gerwehr, S., Carpenter, N., Daumer, C., Dignan, P., Disteche, C., et al. "Down syndrome phenotypes: The consequences of chromosomal imbalance." *Proc. Natl. Acad. Sci. USA* 91: 4997–5001 (1994).

Kozak, M. "An analysis of 59–noncoding sequences from 699 vertebrate messenger RNAs." *Nucleic Acids Res.* 15: 8125–8132 (1987).

Kozak, M. "An analysis of vertebrate mRNA sequences: Intimations of translational control." *J. Cell Biol.* 115: 887–903 (1991).

Krull, C. E., Lansford, R., Gale, N. W., Collazo, A., Marcelle, C., Yancopoulos, G. D., Fraser, S. E., and Bronner–Fraser, M. "Interactions of Eph–related receptors and ligands confer rostrocaudal pattern to trunk neural crest migration." *Curr. Biol.* 7: 571–580 (1997).

Kurioka, K., Nakagawa, K., Denda, K., Miyazawa, K., and Kitamura, N. "Molecular cloning and characterization of a novel protein serine/threonine kinase highly expressed in mouse embryo." *Biochim. Biophys. Acta* 1443: 275–284 (1998).

Lai, C., Gore, M., and Lemke, G. "Structure, expression, and activity of Tyro 3, a neural adhesion–related receptor tyrosine kinase." *Oncogene* 9: 2567–2578 (1994).

Lambe, M., Hsieh, C.–C., Tricholpoulos, D., Ekbom, A., Pavia, M., and Adami, H.–O. "Transient increase in the risk of breast cancer after giving birth." *N. Engl. J. Med.* 331: 5–9 (1994).

Leder, A., Pattengale, P. K., Kuo, A., Stewart, T. A., and Leder, P. Consequences of widespread deregulation of the c–myc gene in transgenic mice: Multiple neoplasms and normal development. *Cell* 45: 485–495 (1986).

Le Guen, L., Thomas, M., Bianchi, M., Halford, N. G., and Kreis, M. "Structure and expression of a gene from *Arabidopsis thaliana* encoding a protein related to SNF1 protein kinase." *Gene* 120: 249–254 (1992).

Lee, K. S., Yuan, Y.–L. O., Kuriyama, R., and Erikson, R. L. "Plk is an M–phase–specific protein kinase and interacts with a kinesin–like protein, CHO1/MKLP–1." *Mol. Cell. Biol.* 15: 7143–7151 (1995).

Lehtola, L., Partanen, J., Sistonen, L., Korhonen, J., Warri, A., Harkonen, P., Clarke, R., and Alitalo, K. "Analysis of tyrosine kinase mRNAs including four FGF receptor mRNAs expressed in MCF–7 breast cancer cells." *Int. J. Cancer* 50: 598–603 (1992).

Levin, D. E., and Bishop, J. M. "A putative protein kinase gene (kin11) is important for growth polarity in *Schizosaccharomyces pombe.*" *Proc. Natl. Acad. Sci. USA* 87: 8272–8276 (1990).

Li, J., Simpson, L., Takahashi, M., Miliaresis, C., Myers, M. P., Tonks, N., and Parsons, R.. "The PTEN/MMACI tumor suppressor induces cell death that is rescued by the AKT/ protein kinase B oncogene." *Cancer Res.* 58: 5667–5672 (1998).

Li, J., Yen, C., Liaw, D., Podsypanina, K., Bose, S., Wang, S. I., Puc, J., Miliaresis, C., Rodgers, L., McCombie, R., Bigner, S. H., Giovanella, B. C., Ittmann, M., Tycko, B., Hibshoosh, H., Wigler, M. H., and Parsons, R. "PTEN, a putative protein tyrosine phosphatase gene mutated in human brain, breast, and prostate cancer [see comments]." *Science* 275: 1943–1947 (1997).

Liang, T. J., Reid, A. E., Xavier, R., Cardiff, R. D. and Wang, T. C. "Transgenic expression of tpr–met oncogene leads to development of mammary hyperplasia and tumors." *J. Clin. Invest.* 97: 2872–2877 (1996).

Liaw, D., Marsh, D. J., Li, J., Dahia, P. L., Wang, S. I., Zheng, Z., Bose, S., Call, K. M., Tsou, H. C., Peacocke, M., Eng, C., and Parsons, R. "Germline mutations of the PTEN gene in Cowden disease, an inherited breast and thyroid cancer syndrome." *Nat. Genet.* 16: 64–67 (1997).

Ligos, J. M., Gerwin, N., Fernandez, P., Gutierrez–Ramos, J. C., and Bernand, A. "Cloning, expression analysis, and functional characterization of PKL 12, a member of a new subfamily of Ser/Thr kinases." *Biochem. Biophys. Res. Commun.* 249: 380–384 (1998).

MacMahon, B., Cole, P., Lin, T. M., Lowe, C. R., Mirra, A. P., Ravnihar, B., Salber, E. J., Valaoras, V. G., and Yuasa, S. "Age at first birth and breast cancer risk." *Bull. WHO* 43: 209–211 (1970).

MacMahon, B., Trichopoulos, D., Brown, J., Andersen, A. P., Aoki, K., Cole, P., DeWaard, F., Kaureniemi, T., Morgan, R. W., Purde, M., Ravnihar, B., Stormby, N., Westlund, K., and Woo, N.–C. "Age at menarche, probability of ovulation and breast cancer risk." *Int. J. Cancer* 29: 13–16 (1982).

Maggiora, P., Marchio, S., Stella, M. C., Giai, M., Belfiore, A., DeBortoli, M., Di Renzo, M. F., Costantino, A., Sismondi, P., and Comoglio, P. M. "Overexpression of the RON gene in human breast carcinoma." *Oncogene* 16: 2927–2933 (1998).

Manfredini, R., Balestri, R., Tagliafico, E., Trevisan, F., Pizzanelli, M., Grande, A., Barbieri, D., Zucchini, P., Citro, G., Franceschi, C., and Ferrari, S. "Antisense inhibition of c–fes proto–oncogene blocks PMA–induced macrophage differentiation in HL60 and in FDC–P1/MAC–11 cells." *Blood* 89: 135–145 (1997).

Mano, H., Sato, K., Yazaki, Y., and Hirai, H. "Tec protein–tyrosine kinase directly associates with Lyn protein–tyrosine kinase through its N–terminal unique domain." *Oncogene* 9: 3205–3211 (1994).

Mano, H., Yamashita, Y., Miyazato, A., Miura, Y., and Ozawa, K. "Tec protein–tyrosine kinase is an effector molecular of Lyn protein–tyrosine kinase." *FASEB J.* 10: 637–642 (1996).

Marquis, S. T., Rajan, J. V., Wynshaw–Boris, A., Xu, J., Yin, G.–Y., Abel, K. J., Weber, B. L., and Chodosh, L. A. "The developmental pattern of Brca1 expression implies a role in differentiation of the breast and other tissues." *Nat. Genet.* 11: 17–26 (1995).

Mischak, H., Kolch, W., Goodnight, J., Davidson, J., Davidson, W. F., Rapp, U., Rose–John, S., and Mushinski, J. F. "Expression of protein kinase C genes in hemopoietic cells is cell–type– and B cell–differentiation stage specific." *J. Immunol.* 147: 3981–3987 (1991).

Moore, F., Weekes, J., and Hardie, D. G. "Evidence that AMP triggers phosphorylation as well as direct allosteric activation of rat liver AMP–activated protein kinase. A sensitive mechanism to protect the cell against ATP depletion." *Eur. J. Biochem.* 199: 691–697 (1991).

Morrison, B. W., and Leder, P. "neu and ras initiate murine mammary tumors that share genetic markers generally absent in c–myc and int–2–initialed tumors." *Oncogene* 9: 3417–3426 (1994).

Muller, W. J., Lee, F. S., Dickson, C., Peters, G. Pattengale, P., and Leder, P. "The int–2 gene product acts as an epithelial growth factor in transgenic mice." *EMBO J.* 9: 907–913 (1990).

Muller, W. J., Sinn, E., Pattengale, P. K., Wallace, R., and Leder, P. "Single–step induction of mammary adenocarcinoma in transgenic mice bearing the activated c–neu oncogene." *Cell* 54: 105–115 (1988).

Munn, R., Webster, M., Muller, W., and Cardiff, R. "Histopathology of transgenic mouse mammary tumors (a short atlas)." *Semin. Cancer Biol.* 6: 153–158 (1995).

Muranaka, T., Banno, H., and Machida, Y. "Characterization of tobacco protein kinase NPK5, a homolog of *Saccharomyces cerevisiae* SNF1 that constitutively activates expression of the glucose–repressible SUC2 gene for a secreted invertase of *S. cerevisiae.*" *Mol. Cell. Biol.* 14: 2958–2965 (1994).

Myohanen, S., Kauppinen, L., Wahlfors, J., Alhonen, L., and Janne, J. "Human spermidine synthase gene: Structure and chromosomal localization." *DNA Cell Biol.* 10: 467–474 (1991).

Myohanen, S., Wahlors, J., Alhonen, L., and Janne, J. "Nucleotide sequence of mouse spermidine synthase cDNA." *DNA Seq.* 4: 343–346 (1994).

Newcomb, P., Storer, B., Longnecker, M., Mittendorf, R., Greenberg, E., Clapp, R. Burke, K., Willett, W., and MacMahon, B. "Lactation and a reduced risk of premeno–pausal breast cancer." *N. Engl. J. Med.* 330: 81–87 (1994).

Niemann, C., Brinkmann, V., Spitzer, E., Hartmann, G., Sachs, M., Naundorf, H., and Birchmeier, W. "Reconstitution of mammary gland development in vitro: requirement of c–met and c–erbB2 signaling for branching and alveolar morphogenesis." *J. Cell Biol.* 143: 533–545 (1998).

Parsa, I. "Loss of a Mr 78,000 marker in chemically induced transplantable carcinomas and primary carcinoma of human pancreas." *Cancer Res.* 48: 2265–2272 (1988).

Partanen, J., Armstrong, E., Makela, T. P., Korhonen, J., Sandberg, M., Renkonen, R., Knuutila, S., Huebner, K., and Alitalo, K. "A novel endothelial cell surface receptor tyrosine kinase with extracellular epidermal growth factor homology domains." *Mol. Cell Biol.* 12: 1698–1707 (1992).

Parthasarathy, L., Parthasarathy, R., and Vadnal, R. "Molecular characterization of coding and untranslated regions of rat cortex lithium–sensitive myoinositol monophosphatase cDNA." *Gene* 191: 81–87 (1997).

Peng, C. Y., Graves, P. R., Ogg, S., Thoma, R. S., Byrnes, M. J., 3rd, Wu, Z., Stephenson, M. T., and Piwnica–Worms, H. "C–TAK1 protein kinase phosphorylates human Cdc25C on serine 216 and promotes 14–3–3 protein binding." *Cell Growth Differ.* 9: 197–208 (1998).

Peng, C. Y., Graves, P. R., Thoma, R. S., Wu, Z., Shaw, A. S., and Piwnica–Worms, H. "Mitotic and G2 checkpoint control: Regulation of 14–3–3 protein binding by phosphorylation of Cdc25C on serine–216." *Science* 277: 1501–1505 (1997).

Pike, M. C., Spicer, D. V., Dahmoush, L. and Press, M. F. "Estrogens, progestogens, normal breast cell proliferation, and breast cancer risk." *Epidemiol. Rev.* 15: 17–35 (1993).

Ponticos, M., Lu, Q. L., Morgan, J. E., Hardie, D. G., Partridge, T. A., and Carling, D. (1998). Dual regulation of the AMP–activated protein kinase provides a novel mechanism for the control of creatine kinase in skeletal muscle. EMBO J. 17: 1688–1699 (1998).

Quintrell, N., Lebo, R., Varmus, H., Bishop, J. M., Pettenati, M. J., LeBeau, M. M., Diaz, M. O., and Rowley, J. D. "Identification of a human gene (HCK) that encodes a protein–tyrosine kinase and is expressed in hemopoietic cells." *Mol. Cell. Biol.* 7: 2267–2275 (1987).

Rahmani, Z., Blouin, J. L., Creau–Goldberg, N., Watkins, P. C., Mattei, J. F., Poissonnier, M., Prieur, M., Chettouh, Z., Nicole, A., Aurias, A., et al., "Critical role of the D21S55 region on chromosome 21 in the pathogenesis of Down syndrome." *Proc. Natl. Acad. Sci. USA* 86: 5958–5962 (1989).

Rajan, J. V., Marquis, S. T., Gardner, H. P., and Chodosh, L. A. "Developmental expression of Brca2 colocalizes with Brca1 and is associated with differentiation in multiple tissues." *Dev. Biol.* 184: 385–401 (1997).

Rawlings, D. J., and Witte, O. N. "Bruton's tyrosine kinase is a key regulator in B–cell development." *Immunol. Rev.* 138: 105–119 (1994).

Robinson, G. W., McKnight, R. A., Smith, G. H., and Hennighausen, L. "Mammary epithelial cells undergo secretory differentiation in cycling virgins but require pregnancy for the establishment of terminal differentiation." *Development* 121: 2079–2090 (1995).

Ruiz, J., Conlon, F., and Robertson, E. "Identification of novel protein kinases expressed in the myocardium of the developing mouse heart." *Mech. Dev.* 48: 153–164 (1994).

Russo, I. H., and Russo, J. "Developmental stage of the rat mammary gland as determinant of its susceptibility to 7,12–dimethylben(a)anthracene." *J. Natl. Cancer Inst.* 61: 1439–1449 (1978).

Russo, J., and Russo, I. H. "Biological and molecular bases of mammary carcinogensis." *Lab. Invest.* 57: 112–137 (1987).

Sano, H., and Youssefian, S. "Light and nutritional regulation of transcripts encoding a wheat protein kinase homolog is mediated by cytokinins." *Proc. Natl. Acad. Sci. USA* 91: 2582–2586.

Santoro, M. M., Collesi, C., Grisendi, S., Gaudino, S., and Comoglio, P. M. "Constitutive activation of the RON gene promotes invasive growth but not transformation." *Mol. Cell. Biol.* 16: 7072–7083 (1996).

Sato, K., Mano, H., Ariyama, T., Inazawa, J., Yazaki, Y., and Hirai, H. "Molecular cloning and analysis of the human Tec protein–tyrosine kinase." *Leukemia* 8: 1663–1672 (1994).

Sato, T. N., Qin, Y., Kozak, C. A., and Andus, K. L. "Tie–1 and tie–2 define another class of putative receptor tyrosine kinase genes expressed in early embryonic vascular system." *Proc. Natl. Acad. Sci. USA* 90: 9355–9358 (1993). [Published erratum appears in *Proc. Natl. Acad. Sci. USA*, 1993, 15, 12056].

Sato, T. N., Tozawa, Y., Deutsch, U., Wolburg–Buchholz, K., Fujiwara, Y., Gendron–Maguire, M., Gridley, T., Wolburg, H., Risau, W., and Qin, Y. "Distinct roles of the receptor tyrosine kinases Tie–1 and Tie–2 in blood vessel formation," *Nature* 376: 70–74 (1995).

Schnurch, H., and Risau, W. "Expression of tie–2, a member of a novel family of receptor tyrosine kinases, in the endothelial cell lineage." *Development* 119: 957–968 (1993).

Shulman, J. M., Benton, R. and St Johnston, D. "The Drosophila homolog of *C. elegans* PAR–1 organizes the oocyte cytoskeleton and directs oskar mRNA localization to the posterior pole." *Cell* 101: 377–388 (2000).

Siliciano, J. D., Morrow, T. A., and Desiderio, S. V. "itk, a T–cell–specific tyrosine kinase gene inducible by interleukin 2." *Proc. Natl. Acad. Sci. USA* 89: 11194–11198 (1992).

Sinn, E., Muller, W., Pattengale, P., Tepler, I., Wallace, R., and Leder, P. "Coexpression of MMTV/v–Ha–ras and MMTV/c–myc genes in transgenic mice: Synergistic action of oncogenes in vivo." *Cell* 49: 465–475 (1987).

Slamon, D. J., Clark, G. M., and Wong, S. G. "Human breast cancer: Correlation of relapse and survival with amplification of the HER–2/neu oncogene." *Science* 235: 177–182 (1987).

Slamon, D. J., Godolphin, W., Jones, L. A., Holt, J. A., Wong, S. G., Keith, D. E., Levin, W. J., Stuart, S. G., Udove, J., Ullrich, A., et al. "Studies of the HER–2/neu proto–oncogene in human breast and ovarian cancer." *Science* 244: 707–712 (1989).

Stairs, D. B., Gardner, H. P., Ha, S. I., Copeland, N. G., Gilbert, D. J., Jenkins, N. A., and Chodosh, L. A. "Cloning and characterization of Krct, a member of a novel subfamily of serine/threonine kinases." *Hum. Mol. Genet.* 7: 2157–2166 (1998).

Stambolic, V., Suzuki, A., de la Pompa, J. L., Brothers, G. M., Mirtsos, C., Sasaki, T., Ruland, J., Penninger, J. M., Siderovski, D. P., and Mak, T. W. "Negative regulation of PKB/Akt–dependent cell survival by the tumor suppressor PTEN." *Cell* 95: 29–39 (1998).

Steck, P. A., Pershouse, M. A., Jasser, S. A., Yung, W. K., Lin, H., Ligon, A. H., Langford, L. A., Baumgard, M. L., Hattier, T., Davis, T., Frye, C., Hu, R., Swedlund, B., Teng, D. H., and Tavtigian, S. V. "Identification of a candidate tumour suppressor gene, MMACI, at chromosome 10q23.3 that is mutated in multiple advanced cancers." *Nat. Genet.* 15: 356–362 (1997).

Sternlicht, M. D., Lochter, A., Sympson, C. J., Huey, B., Rougier, J., Gray, J. W., Pinkel, D., Bissell, M. J. and Werb, Z. "The stromal proteinase MP3/ stromelysin–1 promotes mammary carcinogenesis." *Cell* 98: 137–146 (1999).

Stitt, T. N., Conn, G., Gore, M., Lai, C., Bruno, J., Radziejewski, C., Mattsson, K., Fisher, Gies, D. R., Jones, P. F., et al. "The anticoagulation factor protein S and its relative, Gas6, are ligands for the Tyro 3/Ax1 family of receptor tyrosine kinases." *Cell* 80: 661–670 (1995).

Tamagnone, L., and Comoglio, P. M. "Control of invasive growth by hepatocyte growth factor (HGF) and related scatter factors." *Cytokine Growth Factor Rev.* 8: 129–142 (1997).

ten Dijke, P., Franzen, P., Yamashita, H., Ichijo, H., Heldin, C., and Miyazono, K. "Serine–threonine kinase receptors." *Progr.Growth Factor Res.* 5: 55–72 (1994).

Teng, C. "Mouse lactoferrin gene: a marker for estrogen and epidermal growth factor." *Environ. Health Perspect.* 103: 17–20 (1995).

Thompson–Jaeger, S., Francois, J., Gaughran, J. P., and Tatchell, K. "Deletion of SNF1 affects the nutrient response of yeast and resembles mutations which activate the adenylate cyclase path–way." *Genetics* 129:697–706 (1991).

Tokishita, S., Shiga, Y., Kimura, S., Ohta, T., Kobayashi, M., Hanazato, T., and Yamagata, H. "Cloning and analysis of a cDNA encoding a two–domain hemoglobin chain from the water flea *Daphnia magna.*" *Gene* 189: 73–78 (1997).

Topper, Y. J. and Freeman, C. S. "Multiple hormone interactions in the developmental biology of the mammary gland." *Physiol. Rev.* 60: 1049–1106 (1980).

Tsarfaty, I., Resau, J. H., Rulong, S., Keydar, I., Faletto, D. L., and Vande Woude, G. F. "The met proto–oncogene receptor and lumen formation." *Science* 257: 1258–1261 (1992).

Tsukada, S., Saffran, D. C., Rawlings, D. J., Parolini, O., Allen, R. C., Klisak, I., Sparkes, R. S., Kubagawa, H., Mohandas, T., Quan, S., et al. "Deficient expression of a B cell cytoplasmic tyrosine kinase in human X–linked agammaglobulinemia." *Cell* 72: 279–290 (1993).

Ugolini, F., Adelaide, J., Charafe–Jauffret, E., Nguyen, C., Jacquemier, J., Jordan, B., Birnbaum, D., and Pebusque, M. J. "Differential expression assay of chromosome arm 8p genes identifies Frizzled–related (FRP1/FRZB)and fibroblast growth factor receptor 1 (FGFR1) as candidate breast cancer genes." *Oncogene* 18: 1903–1910 (1999).

Umemori, H., Wanaka, A., Kato, H., Takeuchi, M., Tohyama, M., and Yamamoto, T. "Specific expressions of Fyn and Lyn, lymphocyte antigen receptor–associated tyrosine kinases, in the central nervous system." *Brain Res. Mol. Brain Res.* 16:303–310 (1992).

Valenzuela, D. M., Rojas, E., Griffiths, J. A., Compton, D. L., Gisser, M., Ip, N. Y., Goldfarb, M., and Yancopoulos, G. D. "Identification of full–length and truncated forms of Ehk–3, a novel member of the Eph receptor tyrosine kinase family." *Oncogene* 10: 1573–1580 (1995a).

Valenzuela, D. M., Stitt, T. N., DiStefano, P. S., Rojas, E., Mattsson, K., Compton, D. L., Nunez, L., Park, J. S., Stark, J. L., Gies, D. R., et al. "Receptor tyrosine kinase specific for the skeletal muscle lineage: Expression in embryonic muscle, at the neuromuscular junction, and after injury." *Neuron* 15: 573–584 (1995b).

Wang, M. H., Dlugosz, A. A., Sun, Y., Suda, T., Skeel, A., and Leonard, E. J. "Macrophage–stimulating protein induces proliferation and migration of murine keratinocytes." *Exp. Cell Res.* 226: 39–46 (1996).

Webster, N. J., Resnik, J. L., Reichart, D. B., Strauss, B., Haas, M., and Seely, B. L. "Repression of the insulin receptor promoter by the tumor suppressor gene product p53: A possible mechanism for receptor overexpression in breast cancer." *Cancer Res.* 56: 2781–2788 (1996).

Wilks, A. F. "Cloning members of protein–tyrosine kinase family using polymerase chain reaction." *Methods Enzymol.* 200: 533–546 (1991).

Wilks, A. F. "Two putative protein–tyrosine kinases identified by application of the polymerase chain reaction." *Proc. Natl. Acad. Sci. USA* 86: 1603–1607 (1989).

Wilks, A. F., Kurban, R. R., Hovens, C. M., and Ralph, S. J. "The application of the polymerase chain reaction to cloning members of the protein tyrosine kinase family." *Gene* 85: 67–74 (1989).

Wilson, W., Hawley, S., and Hardie, D. "Glucose repression/derepression in budding yeast: SNF1 protein kinase is activated by phosphorylation under derepressing conditions, and this correlates with a high AMP:ATP ratio." *Curr. Biol.* 6: 1426–1434 (1996).

Woods, A., Cheung, P. C., Smith, F. C., Davison, M. D., Scott, J., Beri, R. K., and Carling, D. "Characterization of AMP–activated protein kinase beta and gamma subunits. Assembly of the hetero–trimeric complex in vitro". *J. Biol. Chem.* 271: 10282–10290 (1996).

Wyllie, A. H., Arends, M. J., Morris, R. G., Walker, S. W., and Evan, G. "The apoptosis endonuclease and its regulation." *Semin. Immunol.* 4: 389–397 (1992).

Yang, X., Hubbard, E. J., and Carlson, M. "A protein kinase substrate identified by the two–hybrid system." *Science* 257: 680–682 (1992).

Yang, X., Jiang, R., and Carlson, M. "A family of proteins containing a conserved domain that mediates interaction with the yeast SNF1 protein kinase complex." *EMBO J.* 13: 5878–5886 (1994).

Yi, T. L., Bolen, J. B., and Ihle, J. N. "Hematopoietic cells express two forms of lyn kinase differing by 21 amino acids in the amino terminus." *Mol. Cell. Biol.* 11: 2391–2398 (1991).

Yokokura, H., Picciotto, M. R., Nairn, A. C., and Hidaka, H. "The regulatory region of calcium/calmodulin–dependent protein kinase I contains closely associated autoinhibitory and calmodulin–binding domains." *J. Biol. Chem.* 270: 23851–23859 (1995).

Yokokura, H., Terada, O., Naito, Y., and Hidaka, H. "Isolation and comparison of rat cDNAs encoding Ca21/calmodulin–dependent protein kinase I isoforms." *Biochim. Biophys. Acta* 1338: 8–12 (1997).

Yu, G., Smithgall, T. E., and Glazer, R. I. "K562 leukemia cell transfected with the human c–fes gene acquire the ability to undergo myeloid differentiation." *J. Biol. Chem.* 264: 10276–10281 (1989).

Ziegler, S. F., Marth, J. D., Lewis, D. B., and Perlmutter, R. M. "Novel protein–tyrosine kinase gene (hck) preferentially expressed in cells of hematopoietic origin." *Mol. Cell. Biol.* 7: 2276–2285 (1987).

Zimmermann, F., Kaufmann, I., Rasenberger, H., and Haussman, P. "Genetics of carbon catabolite repression in *Saccharomyces cerevisiae:* Genes involved in the derepression process." *Mol. Gen. Genet.* 154: 95–103 (1977).

* cited by examiner

FIG. 1

App     ■ □   □ ■   □ ■   □ ■
Hunk    ■ □   ■ □   □ ■   □ ■
Tiam1   ■ □   ■ □   ■ □   □ ■
Erg     ■ □   ■ □   ■ □   ■ □
        60 37   3 1   0 0   1 2

FIG. 3A

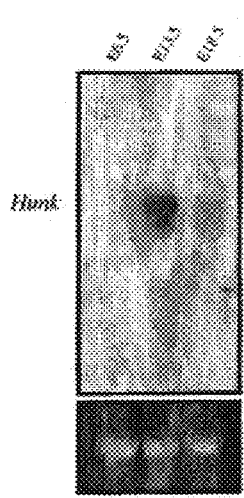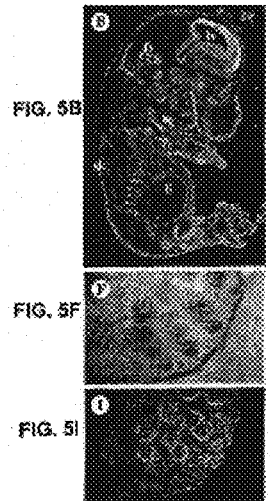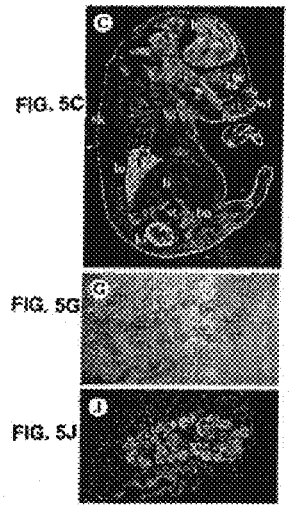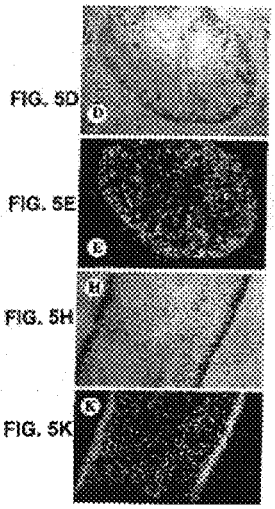
FIG. 5A – FIG. 5K

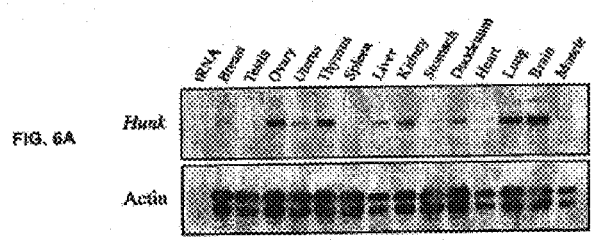
FIG. 6A
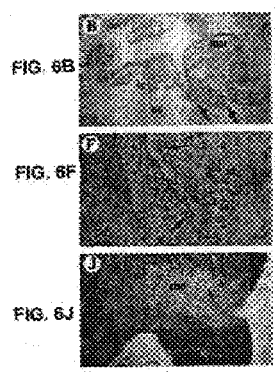 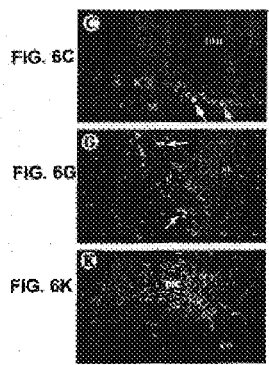 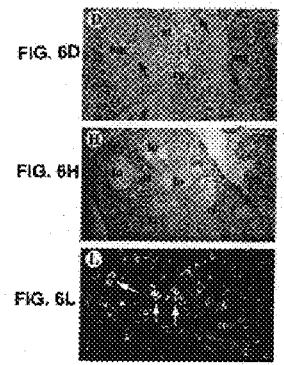 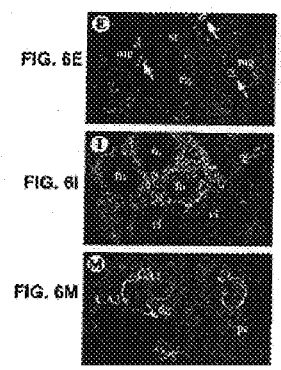
FIG. 6B  FIG. 6C  FIG. 6D  FIG. 6E
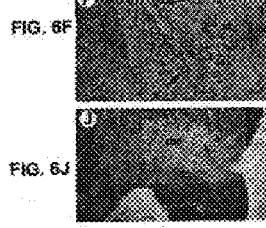 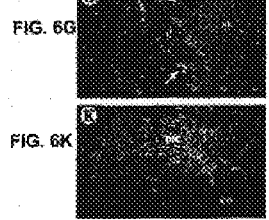 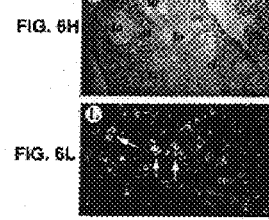 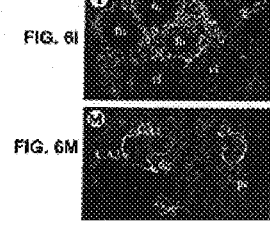
FIG. 6F  FIG. 6G  FIG. 6H  FIG. 6I
  
FIG. 6J  FIG. 6K  FIG. 6L  FIG. 6M FIG. 11A
FIG. 11B
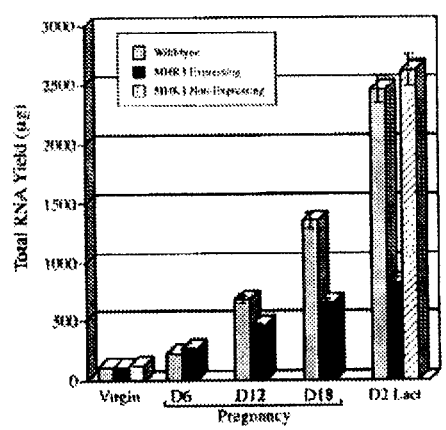
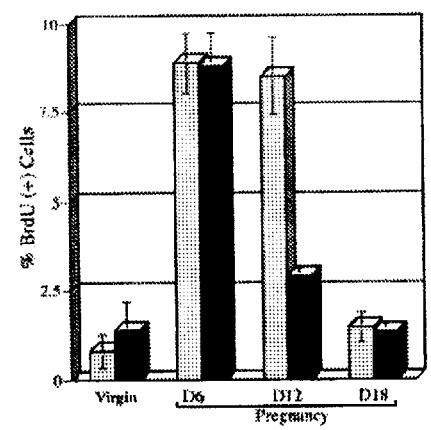

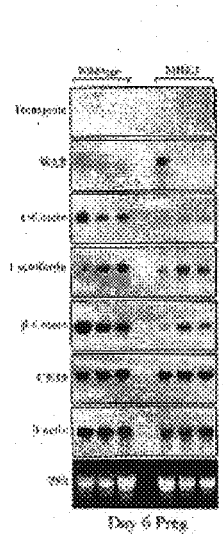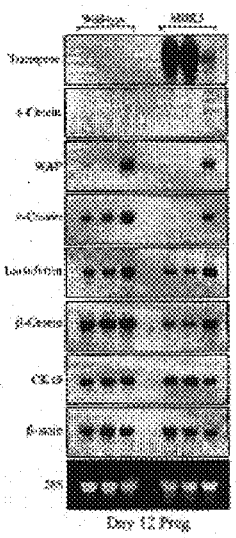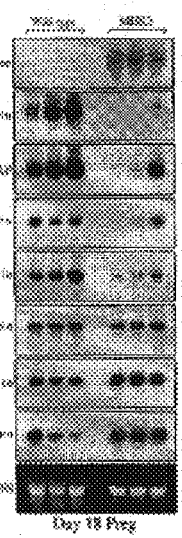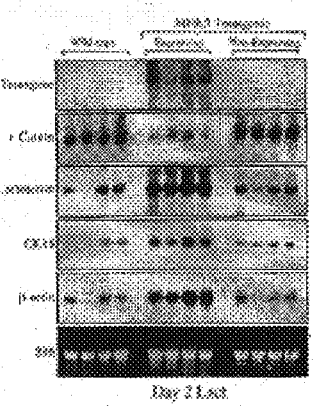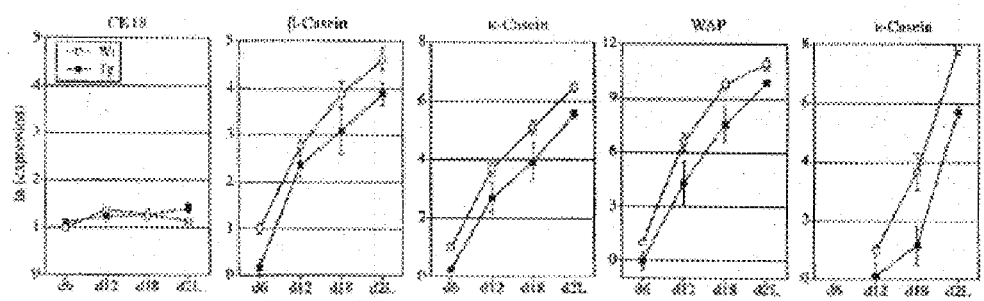
FIG. 13A, FIG. 13B, FIG. 13C, FIG. 13D, FIG. 13E, FIG. 13F

SEQUENCE LISTING

<160> NUMBER OF SEQ ID NOS: 18

<210> SEQ ID NO 1
<211> LENGTH: 5024
<212> TYPE: DNA
<213> ORGANISM: Murinae gen. sp.

<400> SEQUENCE: 1

```
gcaggaggag ccagggcagc cccgggagcc ggaggaggag cggctgcgag cgcgggagcc      60
gagcgagcgc gatgccggca gcggcggggg acgggctctt gggcgagccg gcggcaccgg     120
ggggcgatgg aggcgcggag gacacgacca ggccggcggc ggcctgcgag ggaagtttcc     180
tgcccgcctg ggtgagcggc gtgtcccgcg agcggctccg ggacttccag caccacaagc     240
gcgtgggcaa ctacctcatc ggcagcagga agctgggaga gggctccttc gccaaggtgc     300
gcgaggggct gcacgtgctg acgggagaaa aggtagctat caaggtcatc gataagaaaa     360
gagccaagaa agacacctac gtcaccaaaa acctgcgtcg agagggcag atccagcaga     420 tgatccgaca ccccaacatc acacagctcc tggacatctt ggagacagag aacagctact     480
acctggtcat ggagctgtgt cctggtggca acctcatgca caagatctac gaaaagaaac     540
ggttggatga agccgaggcc cgcagataca tccggcaact catctctgcg gtggaacacc     600
tgcaccgtgc ggggtggtt cacagagact tgaagataga gaatttgcta ctagatgaag     660
acaataatat caagctgatt gactttggct tgagcaactg tgcagggatc ctaggttact     720
cggatccatt cagcacacag tgtggcagcc ctgcctatgc tgcgccagaa ctgcttgcca     780
ggaagaaata tggccccaaa attgatgtct ggtcaatagg cgtgaacatg tatgccatgc     840
tgacggggac cctacctttc actgtggagc ctttcagcct gagggctctg tatcagaaga     900
tggtggacaa agcaatgaat cccctgccga cccagctctc cacaggggcc gtcaactttc     960
tgcgctccct cctggaacca gaccctgtga agaggccgaa tatccagcaa gcgctggcga    1020
atcgctggtt gaatgagaat tacactgaa aggtgccctg caatgtcacc tatcccaaca    1080
ggatttcttt ggaagacctg agtcccagcg tggtgctgca catgactgaa aagctgggct    1140
ataagaacag tgacgtcatc aacacggtgc tctccaaccg cgcctgccac atcctggcca    1200
```

-continued

```
tctacttcct gttgaacaag aaacttgagc gctatttgtc agggaaatca gatatccaag    1260
atagcatctg ctacaagacc cagctctacc agatagagaa gtgcagagcc accaaggagc    1320
cctatgaggc ctccctggat acctggacga gggactttga attccatgct gtgcaggata    1380
aaaagcccaa agaacaagaa aaagaggtg attttctcca ccgtccgttt tccaagaagt    1440
tggacaagaa cctgccttct cacaaacagc catcgccctc gctgatcaca cagctccaga    1500
gtaccaaagc cctgctcaaa gacaggaagg cctccaagtc aggcttcccc gacaaagatt    1560
ccttcgtctg ccgcaatctt ttccgaaaaa cctctgattc caattgtgtg gcttcttctt    1620
ccatggaatt catccctgtc ccacctccca ggacaccaag gattgtaaag aaactagagc    1680
cacaccaacc agggccggga agtgccagca tcctccccaa ggaagagccc ctgctgctgg    1740
atatggtacg ctcctttgag tctgtggatc gagaggacca catagaactg ctgtccccett    1800 ctcaccatta taggatcctg agctcgcctg tgagcctggc tcgtaggaat tctagtgaga    1860
ggacactctc ccaggggctg ctgtccggaa gtacctcacc tctccaaact ccactgcatt    1920
ccacgctggt ctcttttgcc cacgaagaaa agaacagccc cccgaaagag gagggtgtgt    1980
gttcaccgcc tcccgttccc agtaatggcc tcctgcagcc tctggggagc cccaactgtg    2040
tgaagagcag gggacggttc cccatgatgg gcatcggaca gatgctgagg aagcggcacc    2100
agagcctgca gccttcctca gagaggtccc tggacgccag catgtcccct ctgcagccca    2160
tagccccctc cagcctctcc tttgacatgc ccgacggtgt caagggccag tgttaacctg    2220
ggatggcaag attctgggtc tctgtgagga cagccacgga acagagctcc acacaggcag    2280
gcaccagggc atgggtgaac aacctcacgg gagcatcctt tattcttta tacctgccac    2340 acaaagtccc acgcttgtat cagctgaagt ccacactcaa agtccacgca cttacttagg    2400
gaccctctga gacgctgcca ctaggggggag ggagagggg cagactgtgg aatcacacc    2460 ttccagcctg agattttctt tgctatcacc aatcactgag ccctctccag gatcccctca    2520
gtgggctcag agctaaaaac cacacctcca tctgctgggc caatcagatt tccagactgg    2580
taccaggttg tccctccct cctctctgtg tgtctctcac agttctgtaa ctgaccgtca    2640
gtggtcagtt acagtctcac gcggacgtgc cactcgctgg taaggacgtt cacccaacct    2700
agggatccct ctacagaggg aagcaaccct cctttcccta acagtgagtc cccacagagt    2760
gctgagtcac agtgctggac cgggaggaag atgggatggc gcctcagaca gagatggaac    2820
ccagcagcga gaaccagga ggaagacgaa gactcaaacg ctcattcctg tgcaacgttt    2880
tgacagattt ttctttcctc tctttctttt tcccctgacc ttttcttctt tttgggttga    2940
aacttgctga ggattgaacg aacttgtcca aagagatctt tctttatatg aagtcattaa    3000 ttaaatttt ttttaaaga cagggtctca ttaagtagcc caagctggct tcaaactcat    3060
gatcctcctg cctcagcctc caaagtgctg agattacaag tatataccg tgtctggctc    3120 aaaatagcaa ttcaaaaaca aaaactagtt ggccagatga aaagtagttt taccaaattc    3180
acgtgttttt gttttctga gaggctgcag ctcagatggc caaaaagctg caacaggag    3240 gaccacagtg gcctgcctgc ctaagggata gtagcctagc catcctgtgt ttataccgtg    3300
gcagcagcag aaggcataga acttagctcc agatggctct ggagagagag aaaggattct    3360
taaagcagag ttgagacagc aagaagcagg gaattcgctg tgtcatgctg ttctgccgtg    3420
gttagaactt agctgttctg ctgggagcta ggagcaggct tgccgccccc tgggaacacg    3480
ctcacaagac ggttcgtccc caaggaaac agtgcccccc aaacaggctt tcagtccact    3540
```

-continued

```
ctgtaatctg caccttcccc tccaggattg aaccaaagat gcatttccgg ttttgtgact    3600
gtgccactct gtgtgtctct tgtggaacct ggtgttgtct gatcctgtcc ggctggcgct    3660
ggatggagga ctgtctctgt gtgcatcgtg ggccctggta cttagcagag acaaagggt    3720 actgttgtca ggaggggaag acttggcacg ggctggacca cagttagttt agaagttatg    3780
gaacagctca gaatcttctg gtctttgact atttcagatg gggtcagaga ccagagctgt    3840
agccaggaag ccaggttcat catcttggtc catcgattct aaagtgggca aatttctgtg    3900
acgtcacaaa gccggccttt gccagtgagg gctgagacac agtacaactg cctctcattt    3960
actggtggca ggcggcttcc tttggcctct cagagctctg actgaactag aagagaacac    4020
ggatttggct gaccctggaa gaaagctgct ctagtcctgg ctgaatttgg taagacctgg    4080
actacttaaa ccttagggag ggactgactc cctcccgagg acccattaca ggaggaggcc    4140
aggcttttct cccagagctg atggtgttct tcattcagca tggcttccgt tcagctccca    4200
ggacttgaca ctgaaaatag aactctttaa gcagagagaa gaggagaacc atccacagac    4260
gctccccgta tttgatgtga cgtgtttgag ctttgacggg tgaagagtcc ttttaaaaga    4320
taactgccag ctgcaggcat ctggctctgc aaagctggta ggatgtgtac ctgtgtactg    4380
tgcccgcccc ctttctccta gcccttatg tcttttttctg actgtttgct tttctcgtat    4440
gtatgtgtgc ctgtgttggt gcgagcctgt ggagaaagag tctcccatcc ttcaaatgct    4500
tcgagaacag cgtcagatgt acaactagtt tgcctgcgtt gctactggta ccttggactc    4560
tgaactcagg ttaccacct gagtcctcag taggcagtgg acccattgag aggcaaatga    4620
gaacaggagg gagacaagct gtgttctggg gcgcacataa acacctgaca gacgagtcta    4680
ggaaaccgcg tgaaagaaga aatgttaaat tctttattgt tttattatat ttatatggaa    4740
aatgtggcta tccttttgtt aagtgcagag tgtattgtct gtttgaccca tgactgtcct    4800
tcatgaatga gtcttttgcct gtgattctag tcagcctgtg gctactgatg ggaacggccg    4860
atctgtcatc atgtgaagtc caggaggaag aatctatttt agtcatacga tttggtcatg    4920
agtaaggact atatttatgt caccactatt gaatatatgt acttttataa tggctgtgaa    4980
atacactttt tcctcacaaa aaaaaaaaaa aaaaaaaaa aaaa                     5024
```

<210> SEQ ID NO 2
<211> LENGTH: 714
<212> TYPE: PRT
<213> ORGANISM: Murinae gen. sp.

<400> SEQUENCE: 2

```
Met Pro Ala Ala Ala Gly Asp Gly Leu Leu Gly Glu Pro Ala Ala Pro
 1               5                  10                  15

Gly Gly Asp Gly Gly Ala Glu Asp Thr Thr Arg Pro Ala Ala Ala Cys
            20                  25                  30

Glu Gly Ser Phe Leu Pro Ala Trp Val Ser Gly Val Ser Arg Glu Arg
        35                  40                  45

Leu Arg Asp Phe Gln His His Lys Arg Val Gly Asn Tyr Leu Ile Gly
    50                  55                  60

Ser Arg Lys Leu Gly Glu Gly Ser Phe Ala Lys Val Arg Glu Gly Leu
65                  70                  75                  80

His Val Leu Thr Gly Glu Lys Val Ala Ile Lys Val Ile Asp Lys Lys
                85                  90                  95

Arg Ala Lys Lys Asp Thr Tyr Val Thr Lys Asn Leu Arg Arg Glu Gly
            100                 105                 110
```

```
Gln Ile Gln Gln Met Ile Arg His Pro Asn Ile Thr Gln Leu Leu Asp
        115                 120                 125
Ile Leu Glu Thr Glu Asn Ser Tyr Tyr Leu Val Met Glu Leu Cys Pro
130                 135                 140
Gly Gly Asn Leu Met His Lys Ile Tyr Glu Lys Lys Arg Leu Asp Glu
145                 150                 155                 160
Ala Glu Ala Arg Arg Tyr Ile Arg Gln Leu Ile Ser Ala Val Glu His
                165                 170                 175
Leu His Arg Ala Gly Val Val His Arg Asp Leu Lys Ile Glu Asn Leu
            180                 185                 190
Leu Leu Asp Glu Asp Asn Asn Ile Lys Leu Ile Asp Phe Gly Leu Ser
        195                 200                 205
Asn Cys Ala Gly Ile Leu Gly Tyr Ser Asp Pro Phe Ser Thr Gln Cys
210                 215                 220
Gly Ser Pro Ala Tyr Ala Ala Pro Glu Leu Leu Ala Arg Lys Lys Tyr
225                 230                 235                 240
Gly Pro Lys Ile Asp Val Trp Ser Ile Gly Val Asn Met Tyr Ala Met
                245                 250                 255
Leu Thr Gly Thr Leu Pro Phe Thr Val Glu Pro Phe Ser Leu Arg Ala
            260                 265                 270
Leu Tyr Gln Lys Met Val Asp Lys Ala Met Asn Pro Leu Pro Thr Gln
        275                 280                 285
Leu Ser Thr Gly Ala Val Asn Phe Leu Arg Ser Leu Leu Glu Pro Asp
        290                 295                 300
Pro Val Lys Arg Pro Asn Ile Gln Gln Ala Leu Ala Asn Arg Trp Leu
305                 310                 315                 320
Asn Glu Asn Tyr Thr Gly Lys Val Pro Cys Asn Val Thr Tyr Pro Asn
                325                 330                 335
Arg Ile Ser Leu Glu Asp Leu Ser Pro Ser Val Val Leu His Met Thr
            340                 345                 350
Glu Lys Leu Gly Tyr Lys Asn Ser Asp Val Ile Asn Thr Val Leu Ser
        355                 360                 365
Asn Arg Ala Cys His Ile Leu Ala Ile Tyr Phe Leu Leu Asn Lys Lys
370                 375                 380
Leu Glu Arg Tyr Leu Ser Gly Lys Ser Asp Ile Gln Asp Ser Ile Cys
385                 390                 395                 400
Tyr Lys Thr Gln Leu Tyr Gln Ile Glu Lys Cys Arg Ala Thr Lys Glu
                405                 410                 415
Pro Tyr Glu Ala Ser Leu Asp Thr Trp Thr Arg Asp Phe Glu Phe His
            420                 425                 430
Ala Val Gln Asp Lys Lys Pro Lys Glu Gln Glu Lys Arg Gly Asp Phe
        435                 440                 445
Leu His Arg Pro Phe Ser Lys Lys Leu Asp Lys Asn Leu Pro Ser His
450                 455                 460
Lys Gln Pro Ser Pro Ser Leu Ile Thr Gln Leu Gln Ser Thr Lys Ala
465                 470                 475                 480
Leu Leu Lys Asp Arg Lys Ala Ser Lys Ser Gly Phe Pro Asp Lys Asp
                485                 490                 495
Ser Phe Val Cys Arg Asn Leu Phe Arg Lys Thr Ser Asp Ser Asn Cys
            500                 505                 510
Val Ala Ser Ser Ser Met Glu Phe Ile Pro Val Pro Pro Arg Thr
        515                 520                 525

Pro Arg Ile Val Lys Lys Leu Glu Pro His Gln Pro Gly Pro Gly Ser
```

```
                        530                 535                 540
Ala Ser Ile Leu Pro Lys Glu Glu Pro Leu Leu Leu Asp Met Val Arg
545                 550                 555                 560

Ser Phe Glu Ser Val Asp Arg Glu Asp His Ile Glu Leu Leu Ser Pro
                565                 570                 575

Ser His His Tyr Arg Ile Leu Ser Ser Pro Val Ser Leu Ala Arg Arg
            580                 585                 590

Asn Ser Ser Glu Arg Thr Leu Ser Gln Gly Leu Leu Ser Gly Ser Thr
        595                 600                 605

Ser Pro Leu Gln Thr Pro Leu His Ser Thr Leu Val Ser Phe Ala His
    610                 615                 620

Glu Glu Lys Asn Ser Pro Pro Lys Glu Glu Gly Val Cys Ser Pro Pro
625                 630                 635                 640

Pro Val Pro Ser Asn Gly Leu Leu Gln Pro Leu Gly Ser Pro Asn Cys
                645                 650                 655

Val Lys Ser Arg Gly Arg Phe Pro Met Met Gly Ile Gly Gln Met Leu
                660                 665                 670

Arg Lys Arg His Gln Ser Leu Gln Pro Ser Ser Glu Arg Ser Leu Asp
            675                 680                 685

Ala Ser Met Ser Pro Leu Gln Pro Ile Ala Pro Ser Ser Leu Ser Phe
        690                 695                 700

Asp Met Ala Asp Gly Val Lys Gly Gln Cys
705                 710

<210> SEQ ID NO 3
<211> LENGTH: 10
<212> TYPE: RNA
<213> ORGANISM: Unknown Organism
<220> FEATURE:
<223> OTHER INFORMATION: Description of Unknown Organism:Kozak consensus
      sequence

<400> SEQUENCE: 3 gccrccaugg                                                          10

<210> SEQ ID NO 4
<211> LENGTH: 6
<212> TYPE: DNA
<213> ORGANISM: Unknown Organism
<220> FEATURE:
<223> OTHER INFORMATION: Description of Unknown Organism:polyadenylation
      signal

<400> SEQUENCE: 4 aataaa                                                               6

<210> SEQ ID NO 5
<211> LENGTH: 6
<212> TYPE: DNA
<213> ORGANISM: Murinae gen. sp.

<400> SEQUENCE: 5 aataca                                                               6

<210> SEQ ID NO 6
<211> LENGTH: 6
<212> TYPE: PRT
<213> ORGANISM: murine Hunk;fragment

<400> SEQUENCE: 6
```

Asp Leu Lys Pro Glu Asn
 1               5

<210> SEQ ID NO 7
<211> LENGTH: 21
<212> TYPE: DNA
<213> ORGANISM: Artificial Sequence
<220> FEATURE:
<221> NAME/KEY: misc_feature
<222> LOCATION: (17)
<223> OTHER INFORMATION: n is a, c, g, or t
<220> FEATURE:
<223> OTHER INFORMATION: Description of Artificial Sequence:degenerate
      oligonucleotide primer PTKIa

<400> SEQUENCE: 7
gggcccggat ccacmgngay y                                     21

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence:degenerate
      oligonucleotide primer PTKIIa

<400> SEQUENCE: 8
cccggggaat tccawaggac casacrtc                              28

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:degenerate
      oligonucleotide primer BSTKIa

<400> SEQUENCE: 9
gggcccggat ccrtcacmg vgacy                                  25

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence:degenerate
      oligonucleotide primer BSTKIIa

<400> SEQUENCE: 10
cccggggaat tccrwarctc casacatc                              28

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer Gapdh F

<400> SEQUENCE: 11
ctcactcaag attgtcagca atgc                                  24

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:

-continued oligonucleotide primer Gapdh B

<400> SEQUENCE: 12
agggtttctt actccttgga ggc                                             23

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:
    oligonucleotide primer SV40 F

<400> SEQUENCE: 13
ccttaaacgc ctggtgctac gc                                              22

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:
    oligonucleotide primer SV40 B

<400> SEQUENCE: 14
gcagtagcct catcatcact agatgg                                          26

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:
    oligonucleotide primer Hunk F

<400> SEQUENCE: 15
ctttcttttt ccccctgacc                                                 19

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:
    oligonucleotide primer poly(A) B

<400> SEQUENCE: 16
acggtgagta gcgtcacg                                                   18

<210> SEQ ID NO 17
<211> LENGTH: 714
<212> TYPE: PRT
<213> ORGANISM: Homo sapiens

<400> SEQUENCE: 17

Met Pro Ala Ala Ala Gly Asp Gly Leu Leu Gly Glu Pro Ala Ala Pro
 1               5                  10                  15

Gly Gly Gly Gly Gly Ala Glu Asp Ala Ala Arg Pro Ala Ala Ala Cys
            20                  25                  30

Glu Gly Ser Phe Leu Pro Ala Trp Val Ser Gly Val Pro Arg Glu Arg
        35                  40                  45

Leu Arg Asp Phe Gln His His Lys Arg Val Gly Asn Tyr Leu Ile Gly
    50                  55                  60

Ser Arg Lys Leu Gly Glu Gly Ser Phe Ala Lys Val Arg Glu Gly Leu

-continued

```
             65                  70                  75                  80
His Val Leu Thr Gly Glu Lys Val Ala Ile Lys Val Ile Asp Lys Lys
                     85                  90                  95
Arg Ala Lys Lys Asp Thr Tyr Val Thr Lys Asn Leu Arg Arg Glu Gly
                100                 105                 110
Gln Ile Gln Gln Met Ile Arg His Pro Asn Ile Thr Gln Leu Leu Asp
            115                 120                 125
Ile Leu Glu Thr Glu Asn Ser Tyr Leu Val Met Glu Leu Cys Pro
        130                 135                 140
Gly Gly Asn Leu Met His Lys Ile Tyr Glu Lys Lys Arg Leu Glu Glu
145                 150                 155                 160
Ser Glu Ala Arg Arg Tyr Ile Arg Gln Leu Ile Ser Ala Val Glu His
                165                 170                 175
Leu His Arg Ala Gly Val Val His Arg Asp Leu Lys Ile Glu Asn Leu
                180                 185                 190
Leu Leu Asp Glu Asp Asn Asn Ile Lys Leu Ile Asp Phe Gly Leu Ser
            195                 200                 205
Asn Cys Ala Gly Ile Leu Gly Tyr Ser Asp Pro Phe Ser Thr Gln Cys
210                 215                 220
Gly Ser Pro Ala Tyr Ala Ala Pro Glu Leu Leu Ala Arg Lys Lys Tyr
225                 230                 235                 240
Gly Pro Lys Ile Asp Val Trp Ser Ile Gly Val Asn Met Tyr Ala Met
                245                 250                 255
Leu Thr Gly Thr Leu Pro Phe Thr Val Glu Pro Phe Ser Leu Arg Ala
                260                 265                 270
Leu Tyr Gln Lys Met Val Asp Lys Glu Met Asn Pro Leu Pro Thr Gln
            275                 280                 285
Leu Ser Thr Gly Ala Ile Ser Phe Leu Arg Ser Leu Leu Glu Pro Asp
        290                 295                 300
Pro Val Lys Arg Pro Asn Ile Gln Gln Ala Leu Ala Asn Arg Trp Leu
305                 310                 315                 320
Asn Glu Asn Tyr Thr Gly Lys Val Pro Cys Asn Val Thr Tyr Pro Asn
                325                 330                 335
Arg Ile Ser Leu Glu Asp Leu Ser Pro Ser Val Val Leu His Met Thr
                340                 345                 350
Glu Lys Leu Gly Tyr Lys Asn Ser Asp Val Ile Asn Thr Val Leu Ser
            355                 360                 365
Asn Arg Ala Cys His Ile Leu Ala Ile Tyr Phe Leu Leu Asn Lys Lys
        370                 375                 380
Leu Glu Arg Tyr Leu Ser Gly Lys Ser Asp Ile Gln Asp Ser Leu Cys
385                 390                 395                 400
Tyr Lys Thr Arg Leu Tyr Gln Ile Glu Lys Tyr Arg Ala Pro Lys Glu
                405                 410                 415
Ser Tyr Glu Ala Ser Leu Asp Thr Trp Thr Arg Asp Leu Glu Phe His
                420                 425                 430
Ala Val Gln Asp Lys Lys Pro Lys Glu Gln Glu Lys Arg Gly Asp Phe
            435                 440                 445
Leu His Arg Pro Phe Ser Lys Lys Leu Asp Lys Asn Leu Pro Ser His
        450                 455                 460
Lys Gln Pro Ser Gly Ser Leu Met Thr Gln Ile Gln Asn Thr Lys Ala
465                 470                 475                 480
Leu Leu Lys Asp Arg Lys Ala Ser Lys Ser Ser Phe Pro Asp Lys Asp
                485                 490                 495
```

Ser Phe Gly Cys Arg Asn Ile Phe Arg Lys Thr Ser Asp Ser Asn Cys
            500                 505                 510

Val Ala Ser Ser Ser Met Glu Phe Ile Pro Val Pro Pro Arg Thr
        515                 520                 525

Pro Arg Ile Val Lys Lys Pro Glu Pro His Gln Pro Gly Pro Ser
    530                 535                 540

Thr Gly Ile Pro His Lys Glu Asp Pro Leu Met Leu Asp Met Val Arg
545                 550                 555                 560

Ser Phe Glu Ser Val Asp Arg Asp His Val Glu Val Leu Ser Pro
                565                 570                 575

Ser His His Tyr Arg Ile Leu Asn Ser Pro Val Ser Leu Ala Arg Arg
            580                 585                 590

Asn Ser Ser Glu Arg Thr Leu Ser Pro Gly Leu Pro Ser Gly Ser Met
        595                 600                 605

Ser Pro Leu His Thr Pro Leu His Pro Thr Leu Val Ser Phe Ala His
    610                 615                 620

Glu Asp Lys Asn Ser Pro Pro Lys Glu Glu Gly Leu Cys Cys Pro Pro
625                 630                 635                 640

Pro Val Pro Ser Asn Gly Pro Met Gln Pro Leu Gly Ser Pro Asn Cys
                645                 650                 655

Val Lys Ser Arg Gly Arg Phe Pro Met Met Gly Ile Gly Gln Met Leu
            660                 665                 670

Arg Lys Arg His Gln Ser Leu Gln Pro Ser Ala Asp Arg Pro Leu Glu
        675                 680                 685

Ala Ser Leu Pro Pro Leu Gln Pro Leu Ala Pro Val Asn Leu Ala Phe
    690                 695                 700

Asp Met Ala Asp Gly Val Lys Thr Gln Cys
705                 710

<210> SEQ ID NO 18
<211> LENGTH: 2826
<212> TYPE: DNA
<213> ORGANISM: Homo sapiens

<400> SEQUENCE: 18
tactccagag ttgttgtgta gctttgccat tgaaccgatc aatttttaaa ctcagggcgg     60
cggcgggaga agccggggaa gccgaagagc ctggggagga ggagctgcga gcgcgggaga    120
cgagcaggag ccgcgcgggc cgcgggcgag cgcgatgccg gcggcggcgg gggacgggct    180
cctgggggag ccggcggcgc ctgggggcgg cggcggcgcg gaggacgcgg ccaggcccgc    240
ggcggcctgc gagggaagtt tcctgcctgc ctgggtgagc ggcgtgcccc gcgagcggct    300
ccgcgacttc cagcaccaca agcgcgtggg caactacctc atcggcagca ggaagctggg    360
cgagggctcc tttgccaagg tgcgcgaggg gctgcacgtg ctgaccgggg agaaggtggc    420
cataaaagtc attgataaga agagagccaa aaaggacacc tatgtcacca aaaacctgcg    480
gcgagagggt cagatccagc agatgatccg ccacccccaat atcactcagc tccttgatat    540
tttagaaacg gaaacagct actacctggt catggagctg tgccctgggg gcaacctgat    600
gcacaagatc tatgaagaaa gcggctggaa ggagtccgaa gcccgcagat acatccgaca    660
gctcatctct gccgtagagc acctgcaccg ggccggggtg gtccacagag acttgaagat    720
agagaatttg ctactagatg aagacaataa tatcaagctg attgactttg gtttgagcaa    780
ctgcgcaggg atcctgggtt actcggatcc gttcagcaca cagtgtggca gccctgccta    840

-continued

```
cgctgcacct gaactgctcg ccaggaagaa atacggcccc aaaatcgatg tctggtccat    900
aggtgtgaac atgtatgcca tgttgaccgg gacgctgcct ttcacggtgg agcctttcag    960
cctgagggct ttgtaccaga agatggtaga caaagaaatg aaccccctcc ccactcagct   1020
ctccacaggt gccatcagtt tcctgcgctc tctcctggaa ccggatcctg tgaagaggcc   1080
aaatattcag caggcactgg cgaatcgctg gcttaatgag aattacacgg gcaaagtgcc   1140
ctgtaatgtc acctatccca acaggatttc tctggaagat ctgagcccga gcgtcgtgct   1200
gcacatgacc gagaagctgg gttacaagaa cagcgacgtg atcaacactg tgctctccaa   1260
ccgcgcctgc cacatcctgg ccatctactt cctcttaaac aagaaactgg agcgctattt   1320
gtcagggaaa tctgacatcc aggacagcct ctgctacaag acccggctct accagataga   1380
aaagtacagg gccccaagg agtcctatga ggcctctctg gacacctgga cacgagatct    1440
tgaattccat gccgtgcagg ataaaaagcc caaagaacaa gaaaaaagag gggattttct   1500
tcatcgacca ttctccaaga agttggacaa gaacctgccc tcgcacaaac agccctcagg   1560
ctcgcttatg acacagattc agaacaccaa agccctcctg aaggaccgga aggcctccaa   1620
gtccagcttc cccgacaaag attccttttgg ctgccgcaat attttccgca aaacctcaga   1680
ttccaattgt gtggcttctt cttccatgga gttcatcccc gtgccaccgc ccaggacccc   1740
gaggattgtg aagaaaccgg agccccatca gccagggccc ggaagcactg gcatccccca   1800
caaggaagac cccctgatgc tggacatggt gcgctccttc gagtctgtgg atcgcgacga   1860
ccacgtagaa gtgctgtctc cctctcatca ctacaggatt ctgaactccc cggtcagctt   1920
ggctcgcaga aattccagcg agaggacgct gtccccgggt ctgccatccg gaagcatgtc   1980
gcctctccat actcctttgc atccaactct ggtctctttt gctcacgaag ataagaacag   2040
cccccaaaa gaggagggcc tgtgttgccc acctccggtt cccagcaatg gccccatgca   2100
gcctctgggg agccccaatt gtgtgaaaag ccgaggccgg ttccctatga tgggcatcgg   2160
acagatgtta aggaagcgcc atcagagtct gcagccatct gcagataggc ccctggaggc   2220
cagcctgccc ccactgcagc ccctagcccc tgtgaacctt gcctttgaca tggccgatgg   2280
ggtcaagacc cagtgctaac ttgggccagc ggggtttggg gtatctctag aaaacagcaa   2340
ctgaacagag ctccacacat ctgtcagggt gtgagcactc caaggcctcg cgtggagcat   2400
ccttagtccc acctgtagct gaatccacag acccaaagcc tgcacaaccc aacctcgctt   2460
agggaccccc agagatgctg gaatcgctag gagggttggc tccagggca gccaattcct    2520
atcattcaga tcttccttcc tcccaagtac tcaccaaccc cttccacttc ccacttcccc   2580
caggcttggg gggaaaacag ggcatgagcc ttctggggca ctcagattat ggactgttac   2640
cagatctttc ttcacgctgt gctacatgtg tgcctctcac agcagttggc cacagttaca   2700
gggagagaac aatatcacag tcattcatcc aggccacgtt tcctctgcgg agtgtagcag   2760
ccctgccttt catagcaggg attacctgaa ggccagcagg agccgggggc aggcccagga   2820
tcctca                                                              2826
```

HORMONALLY UP-REGULATED, NEU-TUMOR-ASSOCIATED KINASE

REFERENCE TO RELATED APPLICATIONS

This application claims priority to U.S. Provisional Application 60/257,073 filed Dec. 21, 2000.

GOVERNMENT SUPPORT

This work was supported in part by grants from the Elsa U. Pardee Foundation, Grant RPG-99-259-01-DDC from the American Cancer Society, the National Institutes of Health Grants CA83849, CA71513, and CA78410 from the National Cancer Institute, and United States Army Breast Cancer Research Program Grants DAMD17-96-1-6112, DAMD17-98-1-8226, DAMD-99-1-9463, and DAMD-99-1-9349.

FIELD OF THE INVENTION

This invention relates generally to a novel serine/threonine protein kinase, specifically to hormonally up-regulated, neu-tumor-associated kinase (HUNK); and to an analysis of a correlation between carcinogenesis and postnatal mammary development, particularly associated with parity. It further provides insight into the regulation of pregnancy-induced changes in the mammary tissue that occur in response to estrogen and progesterone.

BACKGROUND

A wealth of epidemiological evidence indicates that ovarian hormones play a crucial role in the etiology of breast cancer (Kelsey et al., *Epidemiol. Rev.* 15:36–47 (1993)). Specifically, the observations that early menarche, late menopause and postmenopausal hormone replacement therapy are each associated with increased breast cancer risk, whereas early oophorectomy is associated with decreased breast cancer risk, have led to the hypothesis that breast cancer risk is proportional to cumulative estradiol and progesterone exposure (Henderson et al, *Cancer Res.* 48:246–253 (1988); Pike et al., *Epidemiol. Rev.* 15:17–35 (1993)). As such, elucidating the mechanisms by which hormones contribute to mammary carcinogenesis is a central goal of breast cancer research.

In addition to their roles in the pathogenesis of breast cancer, estradiol and progesterone are the principal steroid hormones responsible for regulating the development of the mammary gland during puberty, pregnancy and lactation (Topper et al., *Physiol. Rev.* 60:1049–1106 (1980)). For example, estradiol action is required for epithelial proliferation and ductal morphogenesis during puberty, whereas progesterone action is required for ductal arborization and alveolar differentiation during pregnancy (Bocchinfuso et al., *J. Mamm. Gland Biol. Neoplasia*, 2:323–334 (1997); Humphreys et al., *J. Mamm. Gland Biol. Neoplasia*, 2:343–354 (1997); Topper et al., 1980). The effects of estradiol and progesterone in a given tissue are ultimately determined by the activation and repression of their respective target genes.

Protein kinases represent the largest class of genes known to regulate differentiation, development, and carcinogenesis in eukaryotes. Many protein kinases function as intermediates in signal transduction pathways that control complex processes such as differentiation, development, and carcinogenesis (Birchmeier et al., *BioEssays*, 15:185–190 (1993); Bolen, *Oncogene*, 8:2025–2031 (1993); Rawlings et al., *Immunol. Rev.*, 138:105–119 (1994)). Accordingly, studies of protein kinases in a wide range of biological systems have led to a more comprehensive understanding of the regulation of cell growth and differentiation (Bolen, 1993; Fantl et al., *Annu. Rev. Biochem.*, 62:453–481(1993); Hardie, *Symp. Soc. Exp. Biol.*, 44:241–255 (1990)).

Not surprisingly, aberrant expression or mutations in several members of the protein kinase family have been reportedly involved in the pathogenesis of cancer both in humans and in rodent model systems (Cardiff et al., *Cancer Surv.*, 16:97–113 (1993); Cooper, *Oncogenes*, Publ., Jones & Bartlett, Boston, Mass., (1990); DiFiore et al., *Cell*, 51:1063–1070 (1987); Muller et al, *Cell*, 54:105–115 (1988)). Protein kinases function as molecular switches in signal transduction pathways that regulate cellular processes, such as proliferation and differentiation. In addition, some protein kinases are expressed in a lineage-specific manner, and are therefore useful markers for defining cellular subtypes (Dymecki et al., *Science*, 247:332–336 (1990); Mischak et al., *J. Immunol.*, 147:3981–3987 (1991); Rawlings et al, 1994; Schnurch et al., *Development.* 19:957–968 (1993); Siliciano et al., *Proc. Natl. Acad. Sci. USA*, 89:11194–11198 (1992); Valenzuela et al., *Neuron*, 15:573–584 (1995)).

A key role played by serine/threonine kinases in regulating diverse cellular processes is exemplified by studies of SNF1-related kinases. The SNF1 family of protein kinases is composed of at least two subfamilies. The first subfamily includes SNF1 and its plant homologues including NPK5, AKin10, BKIN12, and Rkin1, as well as the mammalian SNF1 functional homologue, AMPK (Alderson et al., *Proc. Natl. Acad. Sci. USA*, 88:8602–8605 (1991); Carling et al., *J. Biol. Chem.*, 269 11442–11448 (1994); LeGuen et al., *Gene*, 120:249–254 (1992); Muranaka et al., *Mol. Cell. Biol.*, 14:2958–2965 (1994)). More recently, additional mammalian SNF1-related kinases have been identified that define a second subfamily. These include C-TAK1/p78 (involved in cell cycle control), MARK1, MARK2/Emk, SNRK (involved in adipocyte differentiation), and Msk (involved in murine cardiac development), as well as the *C. elegans* kinase, PAR-1 (Becker et al., *Eur. J. Biochem.*, 235:736–743 (1996); Drewes et al., *Cell*, 89:297–308 (1997); Peng et al., *Science*, 277:1501–1505 (1997); Peng et al., *Cell Growth Differ.*, 9:197–208 (1998); Ruiz et al., *Mech. Dev.*, 48:153–164 (1994)). Less closely related to either subfamily are Wpk4, Melk, and KIN1, SNF1-related kinases found in wheat, mice, and *Schizosaccharomyces pombe*, respectively (Heyer et al., *Mol. Reprod. Dev.*, 47:148–156 (1997); Levin et al., *Proc. Natl. Acad. Sci. USA*, 87:8272–8276 (1990); Sano et al., *Proc. Natl. Acad. Sci. USA*, 91:2582–2586 (1994)).

SNF1 is composed of a heterotrimeric complex that is activated by glucose starvation and is required for the expression of genes in response to nutritional stress (Carlson et al., *Genetics*, 98:25–40 (1981); Celenza et al., *Mol. Cell. Biol.*, 9:5045–5054 (1989); Ciriacy, *Mol. Gen. Genet.*, 154:213–220 (1977); Fields et al., *Nature*, 340:245–246 (1989); Wilson et al., *Curr. Biol.*, 6:1426–1434 (1996); Yang et al., *Science*, 257:680–682 (1992); Yang et al., *EMBO J.*, 13:5878–5886 (1994); Zimmermann et al., *Mol. Gen. Genet.*, 154:95–103 (1977); Hardie et al., *Semin. Cell Biol.*, 5: 409–416 (1994)). In fact, SNF-1 itself has been found to mediate cell cycle arrest in response to starvation (Thompson-Jaeger et al., *Genetics*, 129:697–706 (1991)).

Like SNF1, the mammalian SNF1-related kinase, AMPK, is involved in the cellular response to environmental stresses, particularly those that elevate cellular AMP:ATP ratios. Once activated, AMPK functions to decrease energy-requiring anabolic pathways, such as sterol and fatty acid synthesis while up-regulating energy-producing catabolic pathways such as fatty acid oxidation (Moore et al., *Eur. J. Biochem.*, 199:691–697 (1991); Ponticos et al., *EMBO J.*, 17:1688–1699 (1998)). AMPK complements the snf1 mutation in yeast and phosphorylates some of the same targets as SNF1 (Hardie, *Biochem. Soc. Symp.*, 64:13–27 (1999); Hardie et al., *Biochem. Soc. Trans.*, 25:1229–1231 (1997); Hardie et al., *Biochem. J.*, 338:717–722 (1999); Woods et al., *J. Biol. Chem.*, 271:10282–10290 (1996)). Like SNF1, AMPK is a heterotrimer composed of a, b, and g subunits that are homologous to the subunits of SNF1 (Hardie, 1999). Thus, AMPK and SNF1 are closely related both functionally and structurally, demonstrating that the regulatory pathways in which they operate have been highly conserved during evolution.

For instance, C-TAK1/p78 appears to be involved in cell cycle regulation based on its ability to phosphorylate and inactivate Cdc25c (Peng et al., 1997; Peng et al., 1998). Since Cdc25c controls entry into mitosis by activating cdc2, inactivation of Cdc25c by C-TAK1 would be predicted to regulate proliferation negatively. Consistent with this model, C-TAK1/p78 is down-regulated in adenocarcinomas of the pancreas (Parsa, *Cancer Res.* 48: 2265–2272 (1988)).

Perhaps the most compelling evidence that SNF1 kinases are involved in development is the observation that mutations in the *C. elegans* SNF1-related kinase, PAR-1, result in an inability to establish polarity in the developing embryo (Guo et al., *Cell*, 81:611–620 (1995)). Specifically, par-1 mutations disrupt P granule localization, asymmetric cell divisions, blastomere fates, and mitotic spindle orientation during early embryogenesis.

In an analogous manner, the mammalian PAR-1 homologue, MARK2/Emk, is asymmetrically localized in epithelial cells in vertebrates, and expression of a dominant negative form of MARK2 disrupts both cell polarity and epithelial cell—cell contacts (Bohm et al., *Curr. Biol.*, 7:603–606 (1997)). In addition, overexpression of either MARK2 or its close family member MARK1 results in hyperphosphorylation of microtubule-associated proteins, disruption of the microtubule array, and cell death (Drewes et al 997). Thus, members of the SNF1 kinase family have been demonstrated to regulate a variety of important cellular processes.

In light of these findings, it is clear that prior to the present invention, there was a need to identify and study the role of protein kinases in mammary development and carcinogenesis, as well as provide insight into the regulation of pregnancy-induced changes in the mammary tissue that occur in response to estrogen and progesterone.

SUMMARY

The present invention was the product of a systematic study of the role of protein kinases in mammary gland development and carcinogenesis. Based upon examination of defined stages in postnatal mammary development and in a panel of mammary epithelial cell lines derived from distinct transgenic models of breast cancer, the inventors discovered a novel SNF1-related serine/threonine kinase, Hunk (Hormonally Up-regulated, Neu-Tumor-Associated Kinase). The isolation of Hunk resulted from the examination of 1500 cDNA clones generated using a RT-PCR-based screening strategy, which identified 41 protein kinases, including 33 tyrosine kinases and 8 serine/threonine kinases, 3 of which were novel.

The present invention provides an isolated a 5.0-kb full-length cDNA clone for Hunk that contains the 714-amino-acid open reading frame encoding Hunk. Analysis of this cDNA reveals that Hunk is most closely related to the SNF1 family of serine/threonine kinases and contains a newly described SNF1 homology domain. Accordingly, antisera specific for Hunk detect an 80-kDa polypeptide with associated phosphotransferase activity.

Hunk is located on distal mouse chromosome 16 in a region of conserved synteny with human chromosome 21 q22. During fetal development and in the adult mouse, Hunk mRNA expression is developmentally regulated and tissue-specific. Moreover, in situ hybridization analysis reveals that Hunk expression is restricted to subsets of cells within a variety of organs in the adult mouse, indicating a role for Hunk in murine development.

During postnatal mammary development, Hunk mRNA expression is restricted to a subset of mammary epithelial cells and is temporally regulated with highest levels of expression occurring during early pregnancy. In addition, treatment of mice with 17b-estradiol and progesterone resulted in the rapid and synergistic up-regulation of Hunk expression in a subset of mammary epithelial cells, correlating expression of this kinase with regulation by ovarian hormones. Consistent with the tightly regulated pattern of Hunk expression during pregnancy, mammary glands from transgenic mice engineered to mis-express Hunk in the mammary epithelium manifest temporally distinct defects in epithelial proliferation and differentiation during pregnancy, and fail to undergo normal lobuloalveolar development, suggesting a role for Hunk in affecting the changes in the mammary gland that occur during pregnancy in response to ovarian hormones.

Hunk is expressed in a heterogeneous, epithelial-specific manner throughout postnatal mammary development. This heterogeneous expression pattern is particularly striking in the terminal end bud during puberty and throughout the mammary epithelium during pregnancy. Thus, it is an object of the present invention to provide Hunk as a marker for a particular cellular state or a previously undescribed subtype of mammary epithelial cell.

The steroid hormones 17β-estradiol and progesterone play a central role in the pathogenesis of breast cancer and regulate key phases of mammary gland development. Thus, it is an object of this invention to provide developmental regulatory molecules whose activity is influenced by ovarian hormones, which may also contribute to mammary carcinogenesis.

The HUNK kinase has been shown to be markedly down-regulated in the great majority of human breast cancers compared to benign breast tissue. Expression of HUNK is decreased in both moderately and poorly-differentiated breast cancers, and in both ductal carcinomas and lobular carcinomas. In addition, expression of the HUNK kinase has been shown to be elevated in human ovarian carcinomas when compared to benign tissue, and to be positively correlated with tumor grade. In other words, the higher the tumor grade, the higher the expression of the HUNK kinase. Similarly, expression of the HUNK kinase has been shown to be increased in a subset of human colon carcinomas compared to benign tissue, and to be positively associated with tumor grade. Such a correlation between the genes of the present invention and various cancers has not been previously reported, although it is unclear at this point whether the altered expression of the kinase is a coincidental marker of tumor behavior, or whether the altered expression of the kinase is causally related to the cancer.

The present invention provides a method of delivering Hunk to a target cell, wherein the method comprises delivering to the target cell an effective amount of the kinase, or of the nucleotide sequence encoding the kinase. In preferred embodiments of the invention the amount of the kinase or the gene encoding the kinase delivered to the patient is a therapeutically effective amount. In addition, the kinase can act as a marker of target cell activity.

The present invention also provides a method of delivering an effective amount of an inhibitor of the Hunk kinase to block the activation of, or decrease the activity of, the kinase in the target cell. In particular, the delivered inhibitor comprises an antisense or anti-Hunk molecule. In at least one embodiment, the kinase is overexpressed in the target cell, as compared with a comparable normal cell of the same type. In the alternative, a method is provided for delivering an effective amount of a composition to activate or increase the activity of the Hunk or the nucleotide sequence encoding the kinase in the target cell. In at least one embodiment, the kinase is underexpressed in the target cell, as compared with a comparable normal cell of the same type.

In addition, the invention provides a method of treating cancer, hyperproliferative disease or oncogene expression in a patient, wherein the method comprises delivering to a target cell in the patient a therapeutically effective amount of Hunk or of the nucleotide sequence encoding Hunk. As in the previously described method of delivery, the method of treatment comprises delivering an effective amount of an inhibitor of the Hunk kinase to block the activation of, or decrease the activity of, the kinase in the target cell. In particular, the delivered inhibitor comprises an antisense or anti-Hunk molecule. In at least one embodiment, the kinase is overexpressed in the target cell, as compared with a comparable normal cell of the same type. In the alternative, a method is provided for treating cancer, hyperproliferative disease or oncogene expression in a patient comprising delivering an effective amount of a composition to activate or increase the activity of Hunk or the nucleotide sequence encoding the kinase in the target cell. In at least one embodiment, the kinase is underexpressed in the target cell, as compared with a comparable normal cell of the same type.

The present invention further provides a method of diagnosing a cancer, carcinoma, sarcoma, neoplasm, leukemia, lymphoma or hyperproliferative cell disease or oncogene expression in a patient, wherein the method comprises detecting the presence of and/or measuring Hunk activity or a change therein, as compared with a comparable normal cell of the same type. The method effectively detects and/or measures either the overexpression or under expression of Hunk.

Also provided is a method of rapid screening for a selected compound that modulates the activity of Hunk, comprising: (i) quantifying the expression of the kinase from a target cell; (ii) treating the target cell by administering thereto the selected compound, wherein all other conditions are constant with those in the quantifying step; (iii) quantifying the expression of the kinase from the treated target cell; and (iv) comparing the two quantification measurements to determine the modulation of kinase activity achieved by treatment with the selected compound. The method is applicable to screening for either the presence of kinase, or an underexpression or a measurable decrease in kinase activity, or an overexpression or a measurable increase in kinase activity. It further extends to transformation of the target cell.

Further provided is a method of using Hunk or the nucleotide sequence encoding Hunk as a prognostic tool in a patient to detect the presence of, and/or measure the activity or change of activity of the kinase, as a molecular marker in the patient to predict the behavior of a tumor, cancer, carcinoma, sarcoma, neoplasm, leukemia, lymphoma or hyperproliferative cell disease or oncogene expression in the patient, and applying that detection to predict the appropriate therapy for the patient.

It is particularly preferred that the target cell of the methods of the present invention is human, and that the patient is human.

In addition, the present invention provides a recombinant cell comprising Hunk or HUNK, or a vector or recombinant cell comprising same. Also provided is an antibody specific for the Hunk or HUNK, and homologues, analogs, derivatives or fragments thereof having Hunk activity; as well as an isolated nucleic acid sequence comprising a sequence complementary to all or part of the Hunk or HUNK, and to mutants, derivatives, homologues or fragments thereof encoding a cell having Hunk activity. A preferred complementary sequence comprises antisense activity at a level sufficient to regulate, control, or modulate Hunk activity in a target cell expressing the kinase. Also included in the present invention is a transgenic cell and/or a transgenic animal comprising Hunk or HUNK, or the nucleic acid encoding same.

Additional objects, advantages and novel features of the invention will be set forth in part in the description, examples and figures which follow, and in part will become apparent to those skilled in the art on examination of the following, or may be learned by practice of the invention.

DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s), which are presently preferred. It should be understood, however, that the invention is not limited to the precise arrangements and instrumentalities shown.

FIG. 1 depicts the nucleotide and deduced amino acid sequence of Hunk. The composite nucleic acid sequence and conceptual translation of full-length Hunk cDNA are shown. Nucleotide coordinates are shown on the left. Amino acid coordinates are shown in boldface type on the right. A light shaded box indicates the kinase catalytic domain. Dark shaded boxes denote amino acid motifs characteristic of serine/threonine kinases. The SNF1 homology region, SNH, is denoted by a hatched box. The GC-rich region in the 5'-UTR and the putative polyadenylation sequence in the 3'-UTR are underlined by thin and thick lines, respectively. An asterisk denotes the stop codon. A bracket in the 3' UTR denotes the poly(T) tract, which differs in length between the two independent cDNA clones (clone E8 is shown).

FIG. 2A depicts a Northern hybridization analysis of poly(A)$^+$RNA from NAF mammary epithelial cells hybridized with a cDNA probe specific for Hunk. The relative migration of RNA size markers is indicated. FIG. 2B depicts the immunoprecipitation of Hunk. Antisera raised against the amino-terminus of Hunk (α-Hunk IP), or against polypeptides unrelated to Hunk (control IP) were used to immunoprecipitate protein from lysates prepared from cells that either express (+) or do not express (−) Hunk mRNA. Immunoprecipitated protein was immunoblotted with antisera raised against the carboxyl-terminus of Hunk. FIG. 2C depicts an immunoblotting analysis of Hunk protein using antisera raised against the carboxyl-terminus of Hunk. IVT reactions were performed in rabbit reticulocyte lysates in the presence of unlabeled methionine using either plasmid control (vector) or full-length Hunk cDNA (E8) as a template. IVT reaction products were resolved by SDS-PAGE along with lysates from Hunk-expressing (+) and non-expressing (−) cell lines. The relative migration of the closest molecular weight marker is indicated.

FIGS. 3A and 3B depict a segregation analysis of Hunk within the distal region of mouse chromosome 16 as determined by interspecific back-cross analysis. The segregation patterns of Hunk and flanking genes in backcross animals that were typed for all loci are shown at the top of the figure, although for individual pairs of loci, more than 104 animals were typed. FIG. 3A graphically shows that the segregation patterns of Hunk and flanking genes in the loci are shown at the top of the figure. Each column of FIG. 3A represents the chromosome identified in the backcross progeny that was inherited from the (C57BL/6J ×M. sprefus) $F_1$ parent The shaded boxes in FIG. 3A represent the presence of a C57BL/6J allele, and white boxes represent the presence of a M. spretus allele. The number of offspring inheriting each type of chromosome is listed at the bottom of each column in FIG. 3A. A partial chromosome 16 linkage map showing the location of Hunk in relation to linked genes is shown in FIG. 3B. Recombination distances between loci in centimorgans are shown to the left of the chromosome, and the positions of loci in human chromosomes, where known, are shown to the right. References for the human map positions of loci cited from GDB (Genome Data Base).

FIG. 4A depicts immunoblotting using amino-terminal anti-Hunk antisera to analyze Hunk protein expression. Protein extracts are from MMTV-Hunk transgenic (TG) or wildtype (WT) mice, or HC11 cells, a mammary epithelial cell line that does not express Hunk mRNA (−). The relative migration of the 78-kDa marker is indicated. FIG. 4B depicts an in vitro kinase assay of Hunk immunoprecipitates. An arrowhead indicates the relative migration of histone H⁺, used as an in vitro kinase substrate.

FIGS. 5A–5K depict expression of Hunk during murine embryogenesis. FIG. 5A depicts Northern hybridization analysis of poly(A)⁺ RNA from day E6.5, E13.5, and E18.5 embryos hybridized with a cDNA probe specific for Hunk The 28S ribosomal RNA band is shown as a loading control. FIGS. 5B–5K depict in situ hybridization analysis of Hunk mRNA expression. FIGS. 5D, 5F, 5G and 5H depict bright-field, and FIGS. 5B, 5C, 5E, 5I, 5J and 5K) depict dark field photomicrographs of E13.5 (FIG. 5B) and E18.5 (FIGS. 5C–5K) FVB embryo sections hybridized with a $^{35}$S-lableled Hunk antisense cDNA probe. Tissues shown are kidney (FIGS. 5D, 5E), whisker hair follicles (FIGS. 5F, 5I), submandibular gland (FIGS. 5G, 5J), and skin (FIGS. 5H, 5K). No signal over background was detected in serial sections hybridized with sense Hunk probes: bo, bowel; fv, fourth ventricle; ki, kidney; li, liver; lu, lung; lv, lateral ventricle; oe, olfactory epithelium; sg, submandibular gland; sk, skin; st, stomach; wf, whisker hair follicle. Magnification: 8× (FIGS. 5B, 5C); 20× (FIGS. 5D–5K). Exposure times were optimized for each panel.

FIGS. 6A–6M depict tissue-specific expression of Hunk in adult tissues. FIG. 6A depicts RNase protection analysis of Hunk mRNA expression in tissues of the adult mouse hybridized with antisense RNA probes specific for Hunk and for β-actin. FIGS. 6B–6M depict spatial localization of Hunk expression in tissues of the adult mouse. FIGS. 6B, 6D, 6F, 6H, and 6J depict bright field, and FIGS. 6C, 6E, 6G, 6I, 6K, 6L and 6M depict dark field photomicrographs of in situ hybridization analysis performed on sections of duodenum (FIGS. 6B, 6C), uterus (FIGS. 6D, 6E), prostate (FIGS. 6F, 6G), ovary (FIGS. 6H, 6I), thymus (FIGS. 6J–6L), and brain (FIG. 6M), hybridized with a $^{35}$S-labeled Hunk antisense probe. No signal over background was detected in serial sections hybridized with a sense Hunk probe. Arrows indicate cells expressing Hunk at high levels. CA1 and CA3, regions of the hippocampus; cl, corpus luteum; co, cortex; d, epithelial duct; dg, dentate gyrus; eg, endometrial gland; fo, follicle; ic, intestinal crypt; me, medulla; mg, mesometrial gland; mu, mucosa; pc, parietal cortex; se, serosa; st, stroma. Magnification: 10× (FIG. 6M), 90× (FIGS. 6H–6K), 180× (FIGS. 6B, 6C), 300× (FIGS. 6D, 6E) and 500× (FIGS. 6F, 6G, 6L, 6M).

FIG. 7A depicts RNase protection analysis of Hunk mRNA expression during postnatal developmental of the murine mammary gland. Total RNA isolated from mammary glands at the indicated time points was hybridized to a $^{32}$P-labeled antisense RNA probe specific for Hunk. A $^{32}$P-labeled antisense RNA probe specific for β-actin was included in the same hybridization reaction as an internal loading control. FIG. 7B depicts phosphorimager analysis of RNase protection analysis described in FIG. 7A. Expression levels are shown relative to adult virgin (15 wk). FIG. 7C depicts in situ hybridization analysis of Hunk expression during pregnancy and lactation. Bright-field (top panel) and dark-field (bottom panel) photomicrographs of mammary gland sections from day 7 pregnant, day 20 pregnant or day 9 lactating animals hybridized with an $^{35}$S-labeled Hunk-specific antisense probe. No signal over background was detected in serial sections hybridized with a sense Hunk probe. Exposure times were identical for all dark-field photomicrographs to illustrate changes in Hunk expression during pregnancy. al, alveoli; d, duct; lo, lobule; st, adipose stroma.

FIGS. 8A–8C) depict bright field and FIGS. 8D–8F depict dark field photomicrographs of in situ hybridization analysis performed on mammary gland sections from nulliparous females. A heterogeneous expression pattern of Hunk is seen is all cases, in both epithelial ducts (FIGS. 8A, 8C, 8D and 8F), and terminal end buds (FIGS. 8B, 8C, 8E and 8F). No signal over background was detected in serial sections hybridized with a sense Hunk probe. Exposure times were optimized for each dark-field panel. d, duct; eb, terminal end bud.

FIG. 9C depicts quantification of Hunk expression in mammary glands and uteri from intact FVB female mice after injection with PBS (control; light shaded boxes) or a combination of 5 mg progesterone in 5% gum arabic; and 20 μg of 17b-estradiol in PBS (+E$_2$+P; dark shaded boxes). RNase protection analysis was performed on either breast or uterus total RNA using $^{32}$P-labeled antisense RNA probes specific for Hunk and β-actin. Hunk expression was quantified by phosphorimager analysis and normalized to β-actin. Values are shown relative to control animals. Each bar represents the average of 4 animals ±s.e.m. for each group. FIG. 9D depicts in situ hybridization analysis of Hunk expression in mammary gland sections from oophorectomized mice treated with hormones as described in FIG. 9A. Dark-field exposure times were identical in all cases. al, alveoli; d, duct; st, adipose stroma.

FIG. 10A depicts Northern hybridization analysis of MMTV-Hunk transgene expression in mammary glands from 7- to 9-week-old nulliparous wild type or MHK3 transgenic mice using a $^{32}$P-labeled probe specific for Hunk. The detected mRNA transcript corresponds to the expected size of the MMTV-Hunk transgene. FIG. 10B depicts an RNase protection analysis of MMTV-Hunk transgene expression in organs from a 7-week-old nulliparous MHK3 transgenic female mouse. A $^{32}$P-labeled antisense RNA probe spanning the junction of the 3' end of the Hunk cDNA and the 5' end of the SV40 polyadenylation signal was used to specifically detect transgene expression in 20 μg of total RNA. A $^{32}$P-labeled antisense RNA probe for β-actin was used in the same reaction to control for RNA loading and sample processing. FIG. 10C depicts the immunoprecipitation of Hunk protein from lactating MHK3 transgenic animals. Affinity-purified antisera raised against the C-terminus of Hunk (α-Hunk) was incubated with protein extract from mammary glands harvested from either MHK3 transgenic (Tg) or wild type (Wt) mice during lactation. A control reaction was performed without antisera (no Ab). Immunoprecipitated protein was analyzed by immunoblotting using C-terminal anti-Hunk antisera. The expected migration of Hunk is indicated. FIG. 10D depicts an in vitro kinase assay of anti-Hunk immunoprecipitates. Histone H1 was used as an in vitro kinase substrate for protein immunoprecipitated with (+) or without (–) anti-Hunk antisera from extracts containing equal amounts of protein as in FIG. 10C. The relative migration of histone H1 is indicated. FIG. 10E depicts an immunohistochemical analysis of Hunk protein expression in MHK3 transgenic mice. Anti-Hunk antisera from FIG. 10C and FIG. 10D were used to detect Hunk protein in sections from paraffin-embedded mammary glands harvested from 14-week-old nulliparous wild type or MHK3 transgenic females. A control assay was performed by omitting primary antisera from the protocol. Detection reaction times were identical in all cases.

FIGS. 11A and 11B depict the effects of Hunk overexpression on RNA content and mammary epithelial proliferation. FIG. 11A depicts the amount of total RNA isolated from either wild type (light-shaded boxes), expressing MHK3 transgenic (dark-shaded boxes), or non-expressing MHK3 transgenic (hatched boxes) female mice during mammary development. Total RNA was isolated from mammary glands harvested from female mice at the indicated developmental time points. The average total RNA yield for each group is represented as the mean ±s.e.m. At least 3 mice were analyzed from each group. There is a significant difference in RNA content between wild type and transgenic mammary glands at day 18.5 of pregnancy, and day 2 of lactation (t-test, P=0.047 and 0.0007, respectively). FIG. 11B depicts the relative percentage of BrdU-positive epithelial cells in the mammary glands of wild type and MHK3 transgenic mice during development (t-test, P=0.004).

FIG. 12A depicts a whole-mount analysis of transgenic and wild type mammary glands at the indicated time points. FIG. 12B depicts a Representative Hematoxylin and Eosin-stained sections of paraffin-embedded transgenic and wild type mammary glands. al, alveoli; lo, lobule; st, adipose stroma.

FIGS. 13A–13F depict differentiation defects in MHK3 transgenic mice during pregnancy and lactation. FIGS. 13A–13D depict Northern analysis of gene expression for epithelial differentiation markers (β-casein, κ-casein, lactoferrin, WAP, and ε-casein) in the mammary glands of wild type or MHK3 transgene-expressing animals at day 6.5 of pregnancy (FIG. 13A), day 12.5 of pregnancy (FIG. 13B), day 18.5 of pregnancy (FIG. 13C), or at day 2 of lactation (FIG. 13D). Differentiation marker expression in the mammary glands of non-expressing MHK3 transgenic animals is also shown in FIG. 13D. β-actin expression is shown as a control for dilutional effects, and the 28S ribosomal RNA band is shown as a loading control. FIG. 13E summarizes a multivariate regression analysis of expression products shown in FIGS. 13A–13D, demonstrating the effects of transgene expression and developmental stage on the natural logarithm of cytokeratin 18 and expression levels of milk protein genes. All expression levels were normalized to β-actin. The P value for the significance of the regression model was <0.01 for all differentiation markers shown. FIG. 13F graphically depicts phosphorimager quantification of Northern analyses of expression products shown in FIGS. 13A–13D. Expression levels of milk protein genes were normalized to β-actin expression and are shown on a logarithmic scale in arbitrary units relative to expression levels first detected in wild type animals. Values are shown as the mean ±s.e.m. for each point. The number of mice analyzed in each group is: 4 Wt, 5 Tg (d6.5); 3 Wt, 3 Tg (d12.5 and d18.5); and 4 Wt, 4 Tg, 4 non-expressing Tg (d2 Lact).

DESCRIPTION OF PREFERRED EMBODIMENTS OF THE INVENTION

Figure 2A:
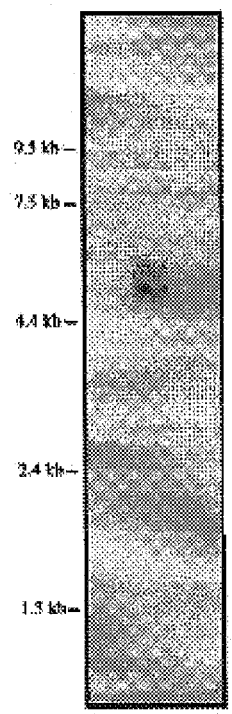
FIGS. 2A–2C depict the expression, identification, and coding potential of Hunk.

The present invention provides a novel SNF1-related serine/threonine kinase, Hunk, in the mammary gland, and methods of use therefor, particularly involving its role in mammary development or carcinogenesis. To better understand the relationship between development and carcinogenesis in the breast, a screen was designed to identify protein kinases that are expressed in the murine mammary gland during development and in mammary tumor cell lines (Chodosh et al., *Dev. Biol.*, 219:259–276 (2000); Gardner et al., *Genomics* 63:279–288 (2000A); Gardner et al., *Genomics* 63: 49–59 (2000B); Gardner et al. *Development* 127:4493–4509 (2000); Stairs et al., *Hum. Mol. Genet.* 7:2157–2166 (1998), each of which is incorporated herein in its entirety).

After kinases were clustered on the basis of similarities in their temporal expression profiles during mammary development, multiple distinct patterns of expression were observed. Analysis of these patterns revealed an ordered set of expression profiles in which successive waves of kinase expression occur during development. This resulted in the identification of a novel serine/threonine kinase of the present invention, the Hormonally Up-Regulated, Neu-Tumor-Associated Kinase (HUNK). Originally referred to as Bstk1 (before being renamed Hunk), the kinase was first identified as a 207-bp RT-PCR product isolated from a mammary epithelial cell line derived from an adenocarcinoma arising in an MMTV-neu transgenic mouse (Chodosh et al., *Cancer Res.* 59:S1765–S1771 (1999)).

The cDNA encoding Hunk expression in the mammary gland was subsequently found to be: (i) tightly regulated during mammary development with a transient peak during early pregnancy; (ii) rapidly and synergistically induced in response to steroid hormones (17b-estradiol and progesterone); (iii) spatially restricted within a subset of mammary epithelial cells throughout postnatal development; and (iv) preferentially expressed in mammary tumor cell lines derived from MMTV-neu, but not in MMTV-c-myc transgenic mice, leading to the choice of the name for the kinase. These data suggest a role for Hunk in mammary development, particularly with respect to pregnancy-induced changes in the mammary gland.

Consistent with this hypothesis, mis-expression of Hunk in the mammary gland disrupted normal lobuloalveolar development during pregnancy and lactation. Specifically, dysregulated Hunk expression resulted in decreased epithelial cell proliferation exclusively during mid-pregnancy, as well as impaired alveolar cell differentiation throughout pregnancy and lactation. Together, these data show that Hunk plays a role in pregnancy-induced changes in the mammary gland, and that Hunk may be involved in the response of the mammary epithelium to ovarian hormones.

Figure 1:
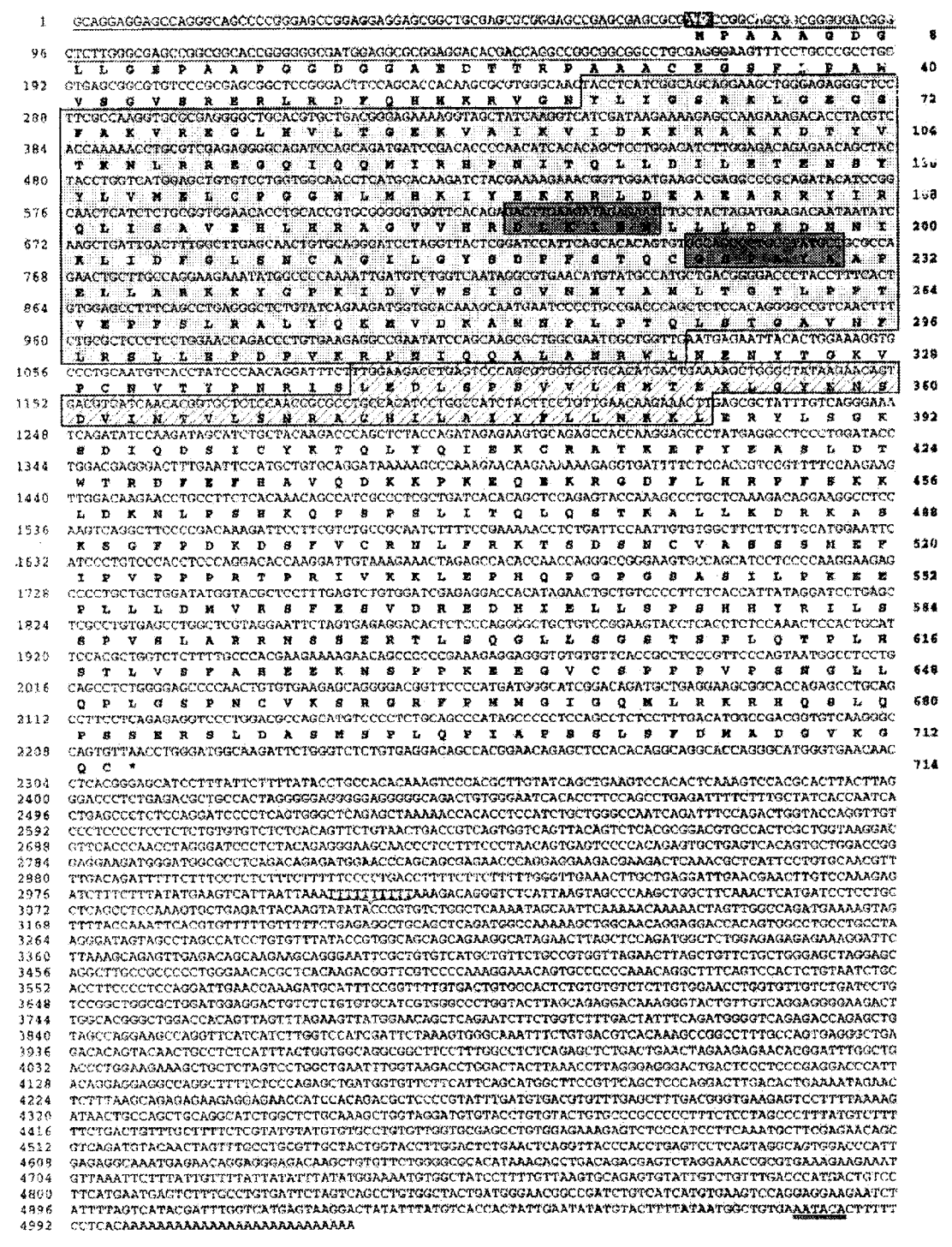

The invention provides the Hunk gene, which has been cloned and fully sequenced as described in the Examples below, and the full length coding sequence of 5026-nucleotides, derived from cDNA is set forth in FIG. 1 and SEQ ID NO:1. Sequence data have been deposited with the EMBL/GenBank Data Libraries under Accession No. AF167987.

Hunk possesses an open reading frame (ORF) 2142 nucleotides in length beginning with a putative initiation codon at nucleotide 72. Comparison of the nucleotide sequence surrounding this site with the Kozak consensus sequence (Kozak, *Nucleic Acids Res.* 15:8125–8132 (1987); Kozak, *Cell Biol.* 115:887–903 (1991)), GCC(A/G)CC AUGG (SEQ ID NO: 3), reveals matches at positions −4, −3, and −2. The nucleotide sequence of the 5'-UTR and the first 100 nucleotides of the Hunk ORF are extremely GC-rich (~80%). Other genes bearing such GC-rich sequences have been found to be subject to translational control (Kozak, 1991).

The 3'-UTR of Hunk is 2.8 kb in length, but lacks a canonical AATAAA polyadenylation signal (SEQ ID NO:4), containing instead the relatively uncommon signal, AATACA (SEQ ID NO:5), 18 nucleotides upstream from the poly(A)$^+$ tract (Bishop et al., Proc. Natl. Acad. Sci. USA, 83:4859–4863 (1986); Herve et al., *Brain Res. Mol. Brain Res.*, 32:125–134 (1995); Myohanen et al., *DNA Cell Biol.* 10:467–474 (1991); Myohanen et al., *DNA Seq.*, 4:343–346 (1994); Parthasarathy et al., *Gene*, 191:81–87 (1997); Tokishita et al., *Gene* 189:73–78 (1997)).

Several lines of evidence confirmed that the identified Hunk cDNA sequence represents the full-length Hunk ORF. First, Northern hybridization analysis of poly(A)$^+$ RNA isolated from mammary epithelial cell lines using a Hunk-specific cDNA probe identified a predominant mRNA species 5.1 kb in length, consistent with the 5025-nucleotide cDNA sequence obtained for clone E8. Secondly, in vitro transcription and translation of clone E8 yielded a polypeptide that is detected by anti-Hunk antisera, that co-migrates with endogenous Hunk, and whose size is consistent with that predicted for the Hunk ORF. Thirdly, comparison of the sequence of clone E8 with a recently isolated human HUNK cDNA clone revealed a high level of homology within the predicted ORF and a lower level of homology 5' of the predicted initiation codon and 3' of the predicted termination codon.

Although Hunk mRNA expression levels were found to be markedly up-regulated during early pregnancy, a developmental stage that is characterized by rapid alveolar cell proliferation, multiple lines of evidence suggest that Hunk expression is not simply a correlate of proliferation. For instance, the temporal profile of Hunk expression in the mammary gland during development is distinct from that of bona fide markers of proliferation, such as cyclin A, cyclin D1, PCNA and PLK (Chodosh et al., 2000). Specifically, the up-regulation of Hunk expression in the mammary gland was confined to early pregnancy, whereas it was found that selected proliferation markers were not only upregulated during early pregnancy, but also during mid-pregnancy, as well as puberty. Moreover, Hunk was not preferentially expressed in proliferative, as compared to non-proliferative, compartments in the mammary gland (i.e. terminal end buds versus ducts during puberty, or alveoli versus ducts during early pregnancy).

Finally, an analysis of actively growing versus confluent or serum-starved mammary epithelial cells revealed no difference in Hunk mRNA levels (Gardner, unpublished). Thus, Hunk expression does not simply reflect the proliferative state of the mammary epithelium, but rather may reflect other developmental pathways or events in the mammary gland.

Hunk up-regulation in the mammary gland during early pregnancy was transient. Thus, the tightly regulated pattern of Hunk expression during pregnancy may be required for normal lobuloalveolar development. This principle was tested by mis-expressing Hunk in the mammary glands of transgenic mice. Forced overexpression of an MMTV-Hunk transgene in the mammary epithelium throughout postnatal development resulted in a defect in lobuloalveolar development with molecular abnormalities first discernible during early pregnancy, cellular abnormalities discernible during mid-pregnancy and morphological abnormalities discernible late in pregnancy.

Specifically, Hunk overexpression resulted in a defect in epithelial proliferation that is restricted to mid-pregnancy and a defect in differentiation that was manifest throughout the developmental interval spanning day 6.5 of pregnancy to day 2 of lactation. In contrast, forced overexpression of Hunk in nulliparous animals had no obvious effect on patterns of proliferation or differentiation. Together, this indicated that the defects observed in lobuloalveolar development in MHK3 mice were due to the failure to down-regulate Hunk expression during mid-pregnancy, rather than to Hunk overexpression per se.

The fact that Hunk overexpression inhibited alveolar proliferation during mid-pregnancy was surprising, given the fact Hunk is normally up-regulated in the mammary gland during early pregnancy—the stage of pregnancy associated with maximum alveolar proliferation. Therefore, mechanistically either the normal role of Hunk is the negative regulation of mammary epithelial proliferation during pregnancy, or the inhibitory effect of Hunk on proliferation at day 12.5 of pregnancy is a consequence of overexpression during a developmental stage at which Hunk is normally down-regulated. Alternatively, the developmental profile of endogenous Hunk activity may be different from that of steady-state levels of Hunk mRNA.

While the present work was in progress, a 588-nucleotide portion of the catalytic domain of Hunk was independently isolated by another group and shown to recognize a mRNA approximately 4 kb in length (Korobko et al., *Dokl. Akad. Nauk.*, 354: 554–556 (1997)). However, the brief Russian paper offers no additional information to lead one to recognize the function or the utility, or the cloning, characterization, localization, function, or in vivo expression of this molecule. Thus, although a small portion of the full-length gene (<10%) appears to have been sequenced from cDNA, insufficient information is provided by the Russian paper to direct one of ordinary skill to the full-length sequence of Hunk, as provided by the present invention. The Russian gene was neither characterized, nor associated with a relevant utility. Therefore, notwithstanding the disclosure of a partial sequence by the Russians, their disclosure provides insufficient information to be considered an enabling reference with regard to the present invention. Nor would one have used the disclosed gene fragment as a probe to identify the full-length Hunk gene, since there was no reason to consider an association of the fragment with mammary development and carcinogenesis, or with the developmentally regulated and tissue-specific expression related thereto, particularly with regard to pregnancy.

Interestingly, sometime after the discovery of Hunk by the present inventors, Korobko et al., 1997 deposited a 5026-nucleotide sequence in GenBank (Accession No. AF055919) that is only 10 nucleotides shorter at the 5' end, and in general, 98% identical to Hunk. Even more interesting is the fact that although the present inventors originated the name Hunk, the Russians also referred to their subsequent deposit as Hunk; they did not identify it by the original Russian identifier for the gene. Therefore, the deposit by Korobko et al., 1997 effectively acknowledges the earlier discovery of Hunk by the present inventors or the Russians would not have had prior knowledge of the name Hunk. Consequently, there can be no question that the first inventors of Hunk were the present inventors, not the Russians, who did not produce a full-length clone for Hunk until after the present inventors had already named the gene.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGCG5' share 50% homology.

In the Examples that follow, two homologous genes were examined, and while not intended to be limited to the exemplified species, standard nomenclature is used. The murine gene is referred to as Hunk, whereas as the human homologue of the same gene is referred to as HUNK. Thus, the invention should be construed to include all Hunk kinase genes that meet the description herein provided, including the human homologue HUNK, as herein described. The nucleotide sequence for human HUNK is set forth as SEQID NO:18, and its corresponding protein expression product as SEQID NO:17. Thus, the invention should be construed to include all Hunk kinase genes that meet the description herein provided, including the human homologue HUNK, as herein described.

The gene encoding Hunk kinase may be isolated as described herein, or by other methods known to those skilled in the art in light of the present disclosure. Alternatively, since, according to the present invention, the gene encoding Hunk has been identified, isolated and characterized, any other Hunk gene which encodes the unique protein kinase described herein may be isolated using recombinant DNA technology, wherein probes derived from Hunk are generated which comprise conserved nucleotide sequences in kinase gene. These probes may be used to identify additional protein kinase genes in genomic DNA libraries obtained from other host strain using the polymerase chain reaction (PCR) or other recombinant DNA methodologies.

An "isolated nucleic acid," as used herein, refers to a nucleic acid sequence, segment, or fragment which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

Further provided in the present invention is the isolated polypeptide protein kinase product of the Hunk gene and its biological equivalents, which are useful in the methods of this invention. Preferably, the amino acid sequence of the isolated protein kinase is about 70% homologous, more preferably about 80% homologous, even more preferably about 90% homologous and most preferably about 95% homologous to the amino acid sequence Hunk, or its human homologue, HUNK.

Figure 3A:
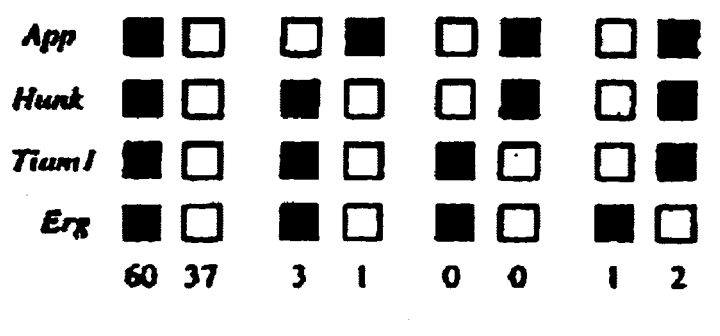
Figure 3B:
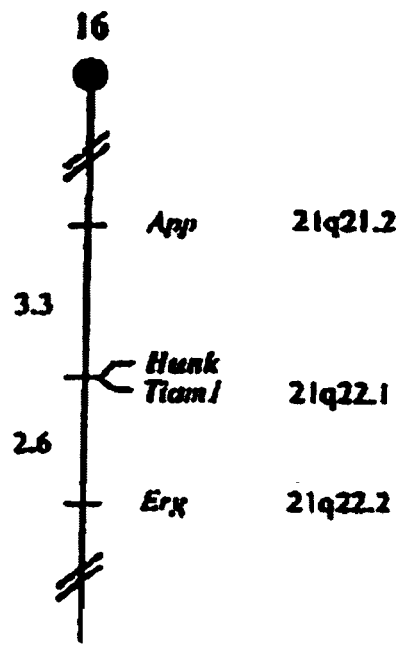

Hunk is located on distal mouse chromosome 16. The distal portion of mouse chromosome 16 shares a region of conserved synteny with human chromosome 21q (summarized in FIG. 3). In particular, Tiam1 has been mapped to 21q22.1. Mutations or segmental trisomy in this region of human chromosome 21 are associated with Alzheimer disease and Down syndrome, respectively. The close linkage between Tiam1 and Hunk in the mouse suggests that the human homologue, HUNK, will map to 21q22, as well. In fact, BLAST alignment of Hunk to sequences in GenBank reveals homology to human genomic DNA sequences cloned from 21q22.1 (gi4835629). This indicates that HUNK also lies within a region of chromosome 21q22, which is believed to contribute to several of the phenotypic features characteristic of Down syndrome (Delabar et al., Eur. J. Hum. Genet., 1:114–124 (1993); Korenberg et al., Proc. Natl. Acad. Sci. USA, 91:4997–5001 (1994); Rahmani et al., Proc. Natl. Acad. Sci. USA, 86:5958–5962 (1989)).

In this regard, it is interesting to note that Hunk is expressed at high levels throughout the brain during murine fetal development, as well as in the adult, with particularly high levels being found in the hippocampus, dentate gyrus, and cortex. However, whether increased Hunk expression in the brain is related to the pathophysiology of Alzheimer disease or Down syndrome is unknown.

Further provided in the present invention is the isolated polypeptide protein kinase product of the Hunk gene and its biological equivalents, which are useful in the methods of this invention. Preferably, the amino acid sequence of the isolated protein kinase is about 70% homologous, more preferably about 80% homologous, even more preferably about 90% homologous and most preferably about 95% homologous to the amino acid sequence Hunk, or its human homologue, HUNK.

Hunk can be purified from natural sources or produced recombinantly using the expression vectors described above in a host-vector system. The proteins also can be produced using the sequence provided in FIG. 1 and methods well known to those of skill in the art. The isolated preparation of Hunk kinase encoded by Hunk may be obtained by cloning and expressing the Hunk gene, and isolating the Hunk protein so expressed, using available technology in the art, and as described herein. The kinase may be purified by following known procedures for protein purification, wherein an immunological, enzymatic or other assay is used to monitor purification at each stage in the procedure.

The conceptual ORF of Hunk comprises 714 amino acids and encodes a polypeptide of predicted molecular mass 79.6 kDa, see FIG. 1 and SEQ ID NO:2. Frequently rounded herein to a size of ~80 kDa, this polypeptide is divisible into an amino-terminal domain of 60 amino acids, a 260-amino-acid kinase catalytic domain, and a 394-amino-acid carboxyl-terminal domain. The carboxyl-terminal domain of Hunk contains a 46-amino-acid conserved motif located 18 amino acids C-terminal to the catalytic domain that is homologous to the previously described SNF1 homology region, or SNH (Becker et al., 1996). The 330 amino acids that are carboxyl to the SNH, lack homology to other known proteins.

Consistent with this, antisera that specifically immuno-precipitate Hunk co-immunoprecipitate phosphotransferase activity, and overexpression of Hunk in mammary epithelial cells increased the level of this phosphotransferase activity. Hunk expression in the mouse is developmentally regulated and tissue-specific both during fetal development and in the adult. Interestingly, within multiple tissues Hunk expression is restricted to sub-sets of cells within specific cellular compartments, predicting a role for Hunk in developmental processes in multiple tissues.

The putative catalytic domain of Hunk contains each of the invariant amino acid motifs characteristic of all protein kinases, as well as sequences specific to serine/threonine kinases (Hanks et al., Methods Enzymol. 200:38–79 (1991); Hanks et al., Science 241:42–52 (1988)). In particular, the DLKPEN motif (SEQ ID NO:6) in subdomain VIB of the Hunk cDNA predicted serine/threonine kinase specificity (ten Dijke et al., Progr. Growth Factor Res. 5: 55–72 (1994)). Hunk also contains the serine/threonine consensus sequence in subdomain VIII N-terminal to the APE motif, which is conserved among all protein kinases. In addition, several amino acids in subdomains I, VII, VIII, IX, X, and XI that are conserved among tyrosine kinases are absent from the Hunk ORF. Thus, the primary sequence analysis further confirms that Hunk encodes a functional serine/threonine kinase, not a tyrosine kinase.

Moreover, the observation that anti-Hunk antisera appear to recognize a single polypeptide species in lysates from cells known to express both transcripts provides evidence that the present invention comprises the isolation of the entire ORF and contain the complete coding region. Taken together, these findings suggest that the cDNA clones isolated represent a full-length Hunk transcript, and that the 5.6-kb Hunk mRNA contains additional 5' or 3' untranslated sequence. The difficulties associated with identifying cDNA clones containing additional 5' sequence may be related to the GC-rich nature of the 5' UTR of Hunk, and the tendency of reverse transcriptase to terminate prematurely in such regions. Alternately, the difference in size between the 5.1- and the 5.6-kb transcripts may be due to utilization of an alternate downstream polyadenylation site during mRNA processing.

A "biological equivalent" is intended to mean any fragment of the nucleic acid or protein, or a mimetic (protein and non-protein mimetic) also having the ability to alter Hunk kinase activity using the assay systems described and exemplified herein. For example, purified Hunk polypeptide can be contacted with a suitable cell, as described above, and under such conditions that its kinase activity is inhibited, or in some cases, it may be enhanced. By "inhibited," is meant a change in kinase activity that is measurably less than the activity exhibited before contact with the subject cell; by "enhances," is meant a change in kinase activity that is measurably greater than the activity exhibited before contact with the subject cell.

The protein is used in substantially pure form. As used herein, the term "substantially pure," or "isolated preparation of a polypeptide" is meant that the protein is substantially free of other biochemical moieties with which it is normally associated in nature. Typically, a compound is isolated when at least 25%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis.

The present invention also provides for analogs of proteins or peptides encoded by Hunk or its human homologue, HUNK. Analogs can differ from naturally occurring proteins or peptides by conservative amino acid sequence differences or by modifications which do not affect sequence, or by both. It is understood that limited modifications can be made to the primary sequence of the Hunk sequence as shown in FIG. 1 and used in this invention without destroying its biological function, and that only the active portion of the entire primary structure may be required in order to effect biological activity. It is further understood that minor modifications of the primary amino acid sequence may result in proteins, which have substantially equivalent or enhanced function as compared to the molecule within the vector. These modifications may be deliberate, e.g., through site-directed mutagenesis, or may be accidental, e.g., through mutation in hosts. All of these modifications are included in the present invention, as long as the Hunk kinase activity is retained essentially as in its native form.

For example, conservative amino acid changes may be made, which although they alter the primary sequence of the protein or peptide, do not normally alter its function. Conservative amino acid substitutions typically include substitutions within the following groups: glycine and alanine; valine, isoleucine, and leucine; aspartic acid and glutamic acid; asparagine and glutamine; serine and threonine; lysine and arginine; or phenylalanine and tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation, e.g., mammalian glycosylating or deglycosylating enzymes. Also embraced are sequences that have phosphorylated amino acid residues, e.g., phosphotyrosine, phosphoserine, or phosphothreonine. Also included are polypeptides that have been modified using ordinary molecular biological techniques so as to improve their resistance to proteolytic degradation or to optimize solubility properties. Analogs of such polypeptides include those containing residues other than naturally-occurring L-amino acids, e.g., D-amino acids or non-naturally occurring synthetic amino acids. The peptides of the invention are not limited to products of any of the specific exemplary processes listed herein.

In addition to substantially full-length polypeptides, the present invention provides for enzymatically active fragments of the polypeptides. A Hunk-specific polypeptide is "enzymatically active" if it is characterized in substantially the same manner as the naturally encoded protein in the assays described below.

As used herein, the term "fragment," as applied to a polypeptide, will ordinarily be at least about 20 contiguous amino acids, typically at least about 50 contiguous amino acids, more typically at least about 70 continuous amino acids, usually at least about 100 contiguous amino acids, more preferably at least about 150 continuous amino acids in length.

Hunk is spatially and temporally regulated during murine mammary development Hunk is expressed at high levels in the embryo during mid-gestation as cells are rapidly proliferating and differentiating and is down-regulated in the embryo prior to parturition. During fetal development, Hunk mRNA is expressed in a tissue-specific manner and is restricted to particular compartments within expressing tissues. Similarly, Hunk is also expressed in a tissue-specific manner in the adult mouse, and its expression is restricted to subsets of cells within these tissues, with highest levels observed in ovary, lung and brain.

Functionally, the temporal and spatial regulation of Hunk has been characterized in various murine and human tissues, as summarized in Table 1.

TABLE 1

Hunk Expression

| | |
|---|---|
| Expression | Expressed in rapidly proliferating cells in vivo; Appears to negatively regulate proliferation in vivo. |
| Breast Cancer in Transgenic Mice | Overexpressed in cell lines from tumors induced by the Neu/ErbB2/Her2 and Ras oncogenes; Not expressed in cell lines from tumors induced by the c-Myc or Int-2 oncogenes. |
| Expression in Human Cancer Cell Lines | Expression is highly heterogeneous in cell lines from a wide variety of tumor types; expressed at high levels (or at undetectable levels) in a subset of breast, colon, ovarian, prostate, lung, CNS, cervical and renal cancer cell lines. |
| Human Breast Cancer | Underexpressed in primary breast cancers compared to benign tissue. |
| Human Colon Cancer | Overexpressed in moderately differentiated colon cancers compared to well differentiated colon cancers and compared to benign tissue. |
| Human Ovarian Cancer | Overexpressed in poorly differentiated and moderately differentiated ovarian cancers compared to well differentiated ovarian cancers and benign tissue. |
| Other Human Cancers | Overexpressed in a subset of endometrial and lung cancers compared to benign tissue. Highly expressed in a subset of carcinoid tumors. |

When compared with other previously isolated protein kinases, multiple sequence alignment showed that the kinase catalytic domain of Hunk displays highest homology to the *S. cerevisiae* SNF1 family of serine/threonine kinases. However, Hunk does not appear to belong to the most recognized SNF1 subfamily of protein kinases, rather Hunk appears to represent a new branch of the SNF1 family tree.

In addition to the conserved kinase catalytic domain, SNF 1 -related protein kinases contain the SNH region of homology, or SNF1 homology domain (Becker et al., 1996). Although amino acids in this motif are conserved in all SNF1 family members, the functional significance of the SNH domain is unknown. Multiple sequence alignment analysis revealed that the SNH is anchored approximately 20 amino acids carboxyl-terminal to the kinase domain, spans approximately 45 amino acids, and extends further toward the amino terminus than previously reported. The present consensus identified amino acids exhibiting greater than 70% conservation among the SNF1 family members shown, as well as residues that are specific for particular SNF1 kinase subfamilies.

Although most conserved residues are shared among all SNF1 family members, some residues are relatively specific for a particular subfamily. For example, the consensus amino acid at position 32 of the SNH is glutamine in subfamily I SNF1 kinases, and tyrosine in subfamily II kinases. Subclass-specific residues are also found at positions 37 (alanine versus valine) and 45 (lysine/arginine versus asparagine).

On the other hand, other than its kinase and SNH domains, Hunk displayed no detectable homology to other members of the SNF1 family or to other known molecules.

Since the distance between the catalytic domain and the SNH is conserved and since many kinases contain autoregulatory domains, it is plausible that the SNH domain functions to regulate kinase activity (Yokokura et al., 1995). Consistent with this speculation is the presence of weak homology between the SNH domain of SNF1 kinases and the autoinhibitory domain of the closely related family of calcium-calmodulin regulated kinases (data not shown). This homology does not extend into the adjacent calmodulin-binding region, consistent with the observation that SNF1 kinases are not regulated by calcium. Regardless, the presence of the SNH domain in all SNF1 kinases raises the possibility that members of this family of molecules may be regulated by a common mechanism.

After isolating the Hunk kinase (Example 1) and cloning and characterizing Hunk as a novel member of the family of SNF1-related protein kinases (Example 2), four founder mice were identified in Example 3 as harboring the MMTV-Hunk transgene in DNA that passed the transgene to offspring in a Mendelian fashion. When screened for transgene expression by Northern hybridization and RNase protection analysis. One founder line, MHK3, was identified that expressed the MMTV-Hunk transgene at high levels, and it became the focus of comparisons with endogenous Hunk expression during all stages of postnatal mammary development.

Defects have been demonstrated in both mammary epithelial proliferation and differentiation in MHK3 animals during pregnancy. For example, the lower total RNA yield obtained from transgenic glands as compared with wild type glands during late pregnancy and lactation probably reflects, in part, the reduced epithelial cell content of MHK3 transgenic glands, since the increase in total RNA present in the mammary gland during lobuloalveolar development is a result both of increases in epithelial cell number and increases in expression of milk protein genes on a per-cell basis (FIG. 11B). Consequently, there was the consideration that the decreased expression of markers for mammary epithelial differentiation observed in MHK3 animals during pregnancy and lactation was a consequence of the decreased alveolar proliferation evident in MHK3 mice at day 12.5 of pregnancy, and the resulting decrease in epithelial cell mass. However, several lines of evidence indicate that the abnormalities in mammary epithelial differentiation observed in MHK3 animals cannot be explained by a decrease in epithelial cell mass. First, the fact that defects in alveolar differentiation in MHK3 animals actually precede the reduction in epithelial proliferation that occurs at day 12.5 strongly argues that defects in differentiation cannot solely be a consequence of defects in proliferation. In addition, RNA extracted from a mammary gland composed of a smaller number of appropriately differentiated epithelial cells would be predicted to give rise to a normal distribution of milk protein gene expression (i.e., early versus late), and to normal levels of expression of milk protein genes when normalized to epithelial cell content.

In contrast, the present invention demonstrates that that both the level and the composition of milk protein RNA produced by the mammary glands of MHK3 animals during pregnancy and lactation is abnormal, even after controlling for differences in epithelial content between wild type and transgenic glands. Consistent with this conclusion, the morphology of the alveolar epithelial cells present in the mammary glands of MHK3 animals at day 18.5 of pregnancy is less differentiated compared with those present in their wild type counterparts. Thus, the reduced expression of differentiation markers in MHK3 transgenic glands reflects the less differentiated state of the mammary epithelial cells present, rather than a reduced number of appropriately differentiated mammary epithelial cells. As such, the data show that the defects in differentiation that occur in MHK3 animals as a consequence of Hunk overexpression are separable from and independent of the defects in proliferation that occur in these animals.

It is important to note that during pregnancy and lactation, a similar magnitude of reduction in the expression of differentiation markers was observed in the mammary glands of MHK3 animals compared with wild type animals, regardless of whether levels of expression of milk protein genes were normalized to β-actin or to the epithelial cell marker, cytokeratin 18 (FIG. 13, and data not shown). In other words, when normalized to β-actin expression, cytokeratin 18 expression levels do not differ between MHK3 transgenic animals and wild type animals at any stage of lobuloalveolar development, reflecting the fact that mammary epithelial cells contribute the vast majority of RNA to the total RNA pool during pregnancy and lactation. This observation explains why cyIokeratin 18 levels show little change during pregnancy when normalized to β-actin expression. Thus, normalizing mRNA expression levels to β-actin mRNA levels itself effectively controls for the decreases in epithelial cell content that occur in MHK3 animals.

The invention further provides a method of identifying a therapeutic compound having activity to affect Hunk by screening a test compound for its ability to modulate the expression or activity of Hunk. Such compounds may include antibiotics. In addition, these kinases will be useful diagnostically, as markers to assess a patient's illness, and/or prognostically, to determine how aggressively, or with what agent a diagnosed case of cancer should be treated.

Methods of the invention can be practiced in vitro, ex vivo or in vivo. When the method is practiced in vitro, the expression vector, protein or polypeptide can be added to the cells in culture or added to a pharmaceutically acceptable carrier as defined below. In addition, the expression vector or Hunk DNA can be inserted into the target cell using well known techniques, such as transfection, electroporation or microinjection. By "target cell" is meant any cell that is the focus of examination, delivery, therapy, modulation or the like by, or as a result of, activation, inactivation, expression or changed expression of Hunk or the nucleotide sequence encoding same, or any cell that effects such modulation, activation, inactivation or the like in the kinase or gene encoding it.

Compounds which are identified using the methods of the invention are candidate therapeutic compounds for treatment of disease states or carcinomas in patients caused by or associated with Hunk or by a cell type related to the activation of Hunk, such as an epithelial cell type as yet unidentified which activates or is activated by the a cancerous condition in the subject, particularly in a human patient. By "patient" is meant any human or animal subject in need or treatment and/or to whom the compositions or methods of the present invention are applied. It is preferred that in a preferred embodiment of the invention, the patient is a mammal, more preferred that it is a veterinary animal, most preferred that it is a human.

The use of the compositions and methods in vitro provides a powerful bioassay for screening for drugs which are agonists or antagonists of Hunk function in these cells. Thus, one can screen for drugs having similar or enhanced ability to prevent or inhibit Hunk kinase activity. It also is useful to assay for drugs having the ability to inhibit carcinogenesis, particularly in the breast. The in vitro method further provides an assay to determine if the method of this invention is useful to treat a subject's pathological condition or disease that has been linked to enhanced Hunk expression, to the developmental stages associated with up-regulation of Hunk, or to a cancerous condition, particularly in the breast or other tissues in which Hunk is highly expressed.

Generally the term "activity," as used herein, is intended to relate to Hunk kinase activity, and an "effective amount" of a compound with regard to Hunk kinase activity means a compound that modulates (inhibits or enhances) that Hunk activity. However, the term "activity" as used herein with regard to a compound, also means the capability of that compound, that in some way affects Hunk kinase activity, to also destroy or inhibit the uncontrolled growth of cells, particularly cancerous cells, particularly in a tumor, or which is capable of inhibiting the pathogenesis, i.e., the disease-causing capacity, of such cells. Similarly, an "effective amount" of such a compound is that amount of the compound that is sufficient to destroy or inhibit the uncontrolled growth of cells, particularly cancerous cells, particularly in a tumor, or which is capable of inhibiting the pathogenesis, i.e., the disease-causing capacity, of such cells. In the alternative, in the case of an enhancing effect, and "effective amount" is that amount of the compound that is sufficient to enhance or increase a desired effect as compared with a corresponding normal cell, or a benign cell.

When the assay methods of the present invention are practiced in vivo in a human patient, it is unnecessary to provide the inducing agent since it is provided by the patient's immune system. However, when practiced in an experimental animal model, it may be necessary to provide an effective amount of the inducing agent in a pharmaceutically acceptable carrier prior to administration of the Hunk product, to induce Hunk kinase activity. When the method is practiced in vivo, the carrying vector, Hunk polypeptide, polypeptide equivalent, or Hunk expression vector (as described below) can be added to a pharmaceutically acceptable carrier and systemically administered to the subject, such as a human patient or an animal, e.g., mouse, guinea pig, simian, rabbit or rat. Alternatively, antisense Hunk nucleic acid or a Hunk inhibitor or suspected Hunk inhibitor is administered. Also, it can be directly infused into the cell by microinjection. A fusion protein also can be constructed comprising the Hunk.

Acceptable "pharmaceutical carriers" are well known to those of skill in the art and can include, but are not limited to any of the standard pharmaceutical carriers, such as phosphate buffered saline, water and emulsions, such as oil/water emulsions and various types of wetting agents.

The assay method can also be practiced ex vivo. Generally, a sample of cells, such as those in the mammary gland, blood or other relevant tissue, can be removed from a subject or animal using methods well known to those of skill in the art. An effective amount of antisense Hunk nucleic acid or a Hunk inhibitor or suspected Hunk inhibitor is added to the cells and the cells are cultured under conditions that favor internalization of the nucleic acid by the cells. The transformed cells are then returned or reintroduced to the same subject or animal (autologous) or one of the same species (allogeneic) in an effective amount and in combination with appropriate pharmaceutical compositions and carriers.

As used herein, the term "administering" for in vivo and ex vivo purposes means providing the subject with an effective amount of the nucleic acid molecule or polypeptide effective to prevent or inhibit Hunk kinase activity in the target cell.

In each of the assays described, control experiments may include the use of mutant strains or cells types that do not encode Hunk. Such strains are generated by disruption of the Hunk gene, generally in vitro, followed by recombination of the disrupted gene into the genome of host cell using technology which is available in the art of recombinant DNA technology as applied to the generation of such mutants in light of the present disclosure. The host may include transgenic hosts.

In one aspect of the assay method of the invention, a compound is assessed for therapeutic activity by examining the effect of the compound on Hunk kinase activity. In this instance, the test compound is added to an assay mixture designed to measure protein kinase activity. The assay mixture may comprise a mixture of cells that express Hunk, a buffer solution suitable for optimal activity of the kinase, and the test compound. Controls may include the assay mixture without the test compound and the assay mixture having the test compound. The mixture is incubated for a selected length of time and temperature under conditions suitable for expression of the Hunk kinase as described herein, whereupon the reaction is stopped and the presence or absence of the kinase, or its overexpression is assessed, also as described herein.

Compounds that modulate the Hunk kinase activity, either by enhancing or inhibiting the activity, are easily identified in the assay by assessing the production of the expression product by the methods exemplified in the presence or absence of the test compound. A lower level, or minimal amounts of Hunk in the presence of the test compound compared with the absence of the test compound in the assay mixture is an indication that the test compound inhibits the selected kinase activity. Similarly, an increased, or significantly increased level, or higher amounts of Hunk in the presence of the test compound compared with the absence of the test compound in the assay mixture is an indication that the test compound enhances or increases the selected kinase activity.

The method of the invention is not limited by the type of test compound used in the assay. The test compound may thus be a synthetic or naturally-occurring molecule, which may comprise a peptide or peptide-like molecule, or it may be any other molecule, either small or large, which is suitable for testing in the assay. In another embodiment, the test compound is an antibody or anti sense molecule directed against Hunk kinase, or its human homologue, or other homologues thereof, or even directed against active fragments of Hunk kinase molecules.

Compounds which inhibit Hunk kinase activity in vitro are then tested for activity directed against HUNK kinase in vivo in humans. Essentially, the compound is administered to the human by any one of the routes described herein, and the effect of the compound is assessed by clinical and symptomatic evaluation. Such assessment is well known to the practitioner in the field of developmental biology or those studying the effect of cancer drugs. Compounds may also be assessed in an in vivo animal model, as herein described.

Precise formulations and dosages will depend on the nature of the test compound and may be determined using standard techniques, by a pharmacologist of ordinary skill in the art.

The compound may also be assessed in non-transgenic animals to determine whether it acts through inhibition of Hunk kinase activity in vivo, or whether it acts via another mechanism. To test this effect of the test compound on activity, the procedures described above are followed using non-transgenic animals instead of transgenic animals.

This invention also provides vector and protein compositions useful for the preparation of medicaments which can be used for preventing or inhibiting Hunk kinase activity, maintaining cellular function and viability in a suitable cell, or for the treatment of a disease characterized by the unwanted death of target cells or uncontrolled cell amplification, particularly as in a cancer.

The nucleic acid can be duplicated using a host-vector system and traditional cloning techniques with appropriate replication vectors. A "host-vector system" refers to host cells which have been transfected with appropriate vectors using recombinant DNA techniques. The vectors and methods disclosed herein are suitable for use in host cells over a wide range of eukaryotic organisms. This invention also encompasses the cells transformed with the novel replication and expression vectors described herein.

The Hunk gene, made and isolated using the above methods, can be directly inserted into an expression vector, e.g., as in the Examples that follow, and inserted into a suitable animal or mammalian cell, such as a mouse or mouse cell or that of a guinea pig, rabbit, simian cell, rat, or acceptable animal host cells, or into a human cell.

A variety of different gene transfer approaches are available to deliver the Hunk gene into a target cell, cells or tissues. Among these are several non-viral vectors, including DNA/liposome complexes, and targeted viral protein DNA complexes. In addition, the Hunk nucleic acid also can be incorporated into a "heterologous DNA" or "expression vector" for the practice of this invention. The term "heterologous DNA" is intended to encompass a DNA polymer, such as viral vector DNA, plasmid vector DNA, or cosmid vector DNA. Prior to insertion into the vector, it is in the form of a separate fragment, or as a component of a larger DNA construct, which has been derived from DNA isolated at least once in substantially pure form as described above, i.e., free of contaminating endogenous materials and in a quantity or concentration enabling identification, manipulation, and recovery of the segment and its component nucleotide sequences by standard biochemical methods, for example, using a cloning vector.

As used herein, "recombinant" is intended to mean that a particular DNA sequence is the product of various combination of cloning, restriction, and ligation steps resulting in a construct having a sequence distinguishable from homologous sequences found in natural systems. Recombinant sequences can be assembled from cloned fragments and short oligonucleotides linkers, or from a series of oligonucleotides.

As noted above, one means to introduce the nucleic acid into the cell of interest is by the use of a recombinant expression vector. "Recombinant expression vector" includes vectors which are capable of expressing DNA sequences contained therein, where such sequences are operatively linked to other sequences capable of effecting their expression. It is implied, although not always explicitly stated, that these expression vectors must be replicable in the host organisms either as episomes or as an integral part of the chromosomal DNA. In sum, "expression vector" is given a functional definition, and any DNA sequence which is capable of effecting expression of a specified DNA sequence disposed therein is included in this term as it is applied to the specified sequence.

Suitable expression vectors include viral vectors, including adenoviruses, adeno-associated viruses, retroviruses, cosmids and others. Adenoviral vectors are a particularly effective means for introducing genes into tissues in vivo because of their high level of expression and efficient transformation of cells both in vitro and in vivo. Thus, in a preferred embodiment of the invention, a disease state or cancer in a patient caused by or related to the expression of Hunk, may be effectively treated by gene transfer by administering to that patient an effective amount of Hunk or an acceptable species-specific homologue thereof, wherein the gene is delivered to the patient by an adenovirus vector using recognized delivery methods.

The invention also relates to eukaryotic host cells comprising a vector comprising Hunk or a homologue thereof, particularly the human homologue, according to the invention. Such a cell is advantageously a mammalian cell, and preferably a human cell, and can comprise said vector in integrated form in the genome, or preferably in non-integrated (episome) form. The subject of the invention is also the therapeutic or prophylactic use of such vector comprising Hunk or a homologue thereof, particularly the human homologue, or eukaryotic host cell.

In addition, the present invention relates to a pharmaceutical composition comprising as therapeutic or prophylactic agent a vector comprising Hunk or a homologue thereof, particularly the human homologue according to the invention, in combination with a vehicle, which is acceptable for pharmaceutical purposes. Alternately it comprises an antisense Hunk molecule, or a Hunk inhibitor molecule or suspected Hunk inhibitor molecule.

The composition according to the invention is intended especially for the preventive or curative treatment of disorders, such as hyperproliferative disorders and cancers, including those induced by carcinogens, viruses and/or dysregulation of oncogene expression; or by the activation of Hunk, or its homologue; or by expression or amplification of a presently unknown cell type, such as an epithelial cell, which is activated or transformed in the breast as a result of or related to Hunk expression, or for which Hunk expression is an indicator. The treatment of cancer (before or after the appearance of significant symptoms) is particularly preferred.

The phrase "therapeutically effective amount" is used herein to mean an amount sufficient to reduce by at least about 15%, preferably by at least 50%, more preferably by at least 90%, and most preferably complete remission of a hyperproliferative disease or cancer of the host. Alternatively, a "therapeutically effective amount" is sufficient to cause an improvement in a clinically significant condition in the host. In the context of the present invention, a therapeutically effective amount of the expression product of Hunk or a homologue thereof, particularly the human homologue, is that amount which is effective to treat a proliferative disease or tumor or other cancerous condition, in a patient or host, thereby effecting a reduction in size or virulence or the elimination of such disease or cancer. Preferably, administration or expression of an "effective" amount of the expression product of Hunk or a homologue thereof, particularly the human homologue resolves the underlying infection or cancer.

A pharmaceutical composition according to the invention may be manufactured in a conventional manner. In particular, a therapeutically effective amount of a therapeutic or prophylactic agent is combined with a vehicle such as a diluent. A composition according to the invention may be administered to a patient (human or animal) by aerosol or via any conventional route in use in the field of the art, especially via the oral, subcutaneous, intramuscular, intravenous, intraperitoneal, intrapulmonary, intratumoral, intratracheal route or a combination of routes. The administration may take place in a single dose or a dose repeated one or more times after a certain time interval.

The appropriate administration route and dosage vary in accordance with various parameters, for example with the individual being treated or the disorder to be treated, or alternatively with the gene(s) of interest to be transferred.

The particular formulation employed will be selected according to conventional knowledge depending on the properties of the tumor, or hyperproliferative target tissue and the desired site of action to ensure optimal activity of the active ingredients, i.e., the extent to which the protein kinase reaches its target tissue or a biological fluid from which the drug has access to its site of action. In addition, these viruses may be delivered using any vehicles useful for administration of the protein kinase, which would be known to those skilled in the art. It can be packaged into capsules, tablets, etc. using formulations known to those skilled in the art of pharmaceutical formulation.

Dosages for a given host can be determined using conventional considerations, e.g., by customary comparison of the differential activities of the subject preparations and a known appropriate, conventional pharmacological protocol. Generally, a pharmaceutical composition according to the invention comprises a dose of the protein kinase according to the invention of between $10^4$ and $10^{14}$, advantageously $10^5$ and $10^{13}$, and preferably $10^6$ and $10^{11}$.

A pharmaceutical composition, especially one used for prophylactic purposes, can comprise, in addition, a pharmaceutically acceptable adjuvant, carrier, fillers or the like. Suitable pharmaceutically acceptable carriers are well known in the art. Examples of typical carriers include saline, buffered saline and other salts, liposomes, and surfactants. The adenovirus may also be lyophilized and administered in the forms of a powder. Taking appropriate precautions not to denature the protein, the preparations can be sterilized and if desired mixed with auxiliary agents, e.g., lubricants, preservatives, stabilizers, wetting agents, emulsifiers, salts for influencing osmotic pressure, buffers, and the like that do not deleteriously react with the active virus. They also can be combined where desired with other biologically active agents, e.g., antisense DNA or mRNA.

The compositions and methods described herein can be useful for preventing or treating cancers of a number of types, including but not limited to breast cancer, sarcomas and other neoplasms, bladder cancer, colon cancer, lung cancer, pancreatic cancer, gastric cancer, cervical cancer, ovarian cancer, brain cancers, various leukemias and lymphomas. One would expect that any other human tumor cell, regardless of expression of functional p53, would be subject to treatment or prevention by the methods of the present invention, although the particular emphasis is on mammary cells and mammary tumors. The invention also encompasses a method of treatment, according to which a therapeutically effective amount of the protein kinase, or a vector comprising same according to the invention is administered to a patient requiring such treatment.

Also useful in conjunction with the methods provided in the present invention would be chemotherapy, phototherapy, anti-angiogenic or irradiation therapies, separately or combined, which maybe used before or during the enhanced treatments of the present invention, but will be most effectively used after the cells have been sensitized by the present methods. As used herein, the phrase "chemotherapeutic agent" means any chemical agent or drug used in chemotherapy treatment, which selectively affects tumor cells, including but not limited to, such agents as adriamycin, actinomycin D, camptothecin, colchicine, taxol, cisplatinum, vincristine, vinblastine, and methotrexate. Other such agents are well known in the art.

As described above, the agents encompassed by this invention are not limited to working by any one mechanism, and may for example be effective by direct poisoning, apoptosis or other mechanisms of cell death or killing, tumor inactivation, or other mechanisms known or unknown. The means for contacting tumor cells with these agents and for administering a chemotherapeutic agent to a subject are well known and readily available to those of skill in the art.

As also used herein, the term "irradiation" or "irradiating" is intended in its broadest sense to include any treatment of a tumor cell or subject by photons, electrons, neutrons or other ionizing radiations. These radiations include, but are not limited to, X-rays, gamma-radiation, or heavy ion particles, such as alpha or beta particles. Moreover, the irradiation may be radioactive, as is commonly used in cancer treatment and can include interstitial irradiation. The means for irradiating tumor cells and a subject are well known and readily available to those of skill in the art.

The protein kinase of the present invention can also be used to express immuno-stimulatory proteins that can increase the potential anti-tumor immune response, suicide genes, anti-angiogenic proteins, and/or other proteins that augment the efficacy of these treatments.

The present invention is further described in the following examples. These examples are provided for purposes of illustration only, and are not intended to be limiting unless otherwise specified. The various scenarios are relevant for many practical situations, and are intended to be merely exemplary to those skilled in the art. These examples are not to be construed as limiting the scope of the appended claims. Thus, the invention should in no way be construed as being limited to the following example, but rather, should be construed to encompass any and all variations which become evident in light of the teaching provided herein.

EXAMPLES

The screening, RNA analyses, in situ hybridization and constructions described below are carried out according to the general techniques of genetic engineering and molecular cloning detailed in, e.g., Maniatis et al., (*Laboratory Manual*, Cold Spring Harbor, Laboratory Press, Cold Spring Harbor, N.Y. (1989)). The steps of PCR amplification follow known protocols, as described in, e.g., *PCR Protocols—A Guide to Methods and Applications* (ed., Innis, Gelfand, Sninsky and White, Academic Press Inc. (1990)). Variations of such methods, so long as not substantial, are within the understanding of one of ordinary skill in the art.

EXAMPLE 1

Protein Kinases Expressed During Mammary Development

To study the role of protein kinases in regulating mammary proliferation and differentiation, the following screen was designed to identify protein kinases expressed in the mammary gland and in breast cancer cell lines. A reverse transcriptase (RT)-PCR cloning strategy was employed that relied on the use of degenerate oligonucleotide primers corresponding to conserved amino acid motifs present within the catalytic domain of protein tyrosine kinases (Wilks et al., *Gene*, 85:67–74 (1989); Wilks et al., *Proc. Natl. Acad. Sci. USA*, 86:1603–1607 (1989)).

Cell Culture. Mammary epithelial cell lines were derived from mammary tumors or hyperplastic lesions that arose in mouse mammary tumor virus (MMTV)-c-myc, MMTV-int-2, MMTV-neu/NT, or MMTV-H-ras transgenic mice and included: the neu transgene-initiated mammary tumor-derived cell lines SMF, NAF, NF639, NF11005, and NK-2; the c-myc transgene-initiated mammary tumor-derived cell lines 16MB9a, 8Ma1a, MBp6, M158, and M1011; the H-ras transgene-initiated mammary tumor-derived cell lines AC816, AC236, and AC711; the int-2 transgene-initiated hyperplastic cell line HBI2; and the int-2 transgene-initiated mammary tumor-derived cell line 1128 (Morrison et al., 1994). Additional cell lines were obtained from ATCC and included NIH3T3 cells and the nontransformed murine mammary epithelial cell lines NMuMG and CL-S1. All cells were cultured under identical conditions in DMEM medium supplemented with 10% bovine calf serum, 2 mM L-glutamine, 100 units/ml penicillin, and 100 mg/ml streptomycin.

Animals and Tissues. FVB mice were housed under barrier conditions with a 12-h light/dark cycle. The mammary glands from between 10 and 40 age-matched mice were pooled for each developmental point. Mice for pregnancy points were mated at 4–5 weeks of age. Mammary gland harvest consisted in all cases of the No. 3, 4, and 5 mammary glands. The lymph node embedded in the No. 4 mammary gland was removed prior to harvest. Tissues used for RNA preparation were snap frozen on dry ice. Tissues used for in situ hybridization analysis were embedded in O.C.T. embedding medium (10.24% polyvinyl alcohol; 4.26% polyethylene glycol) and frozen in a dry ice/isopentane bath. Developmental expression patterns for 13 kinases were confirmed using independent pools of RNA. Analysis of the developmental expression pattern for an additional kinase using these independent pooled samples revealed a similar pregnancy-up-regulated expression pattern that differed with respect to the day of pregnancy at which maximal up-regulation occurred.

Construction and Analysis of Kinase-Specific cDNA Libraries. RNA prepared from nine different sources was used as starting material for the generation of kinase-specific cDNA libraries. Kinase-specific cDNA libraries were constructed using mRNA prepared from the mammary glands of mice at specified stages of development and from a panel of mammary epithelial cell lines. Specifically, total RNA was prepared from the mammary glands of either 5-week-old nulliparous female mice or parous mice that had undergone a single pregnancy followed by 21 days of lactation and 2 days of postlactational regression. Total RNA was also prepared from the seven mammary epithelial cell lines NMuMG, CL-S1, HBI2, SMF, 16MB9a, AC816, and 1128, described above (Leder et al., Cell, 45:485–495 (1986); Muller et al., 1988; Muller et al., EMBO J., 9:907–913 (1990); Sinn et al., Cell, 49:465–475 (1987)). Mammary tumors arising in each of these transgenic strains have previously been demonstrated to possess distinct and characteristic histopathologies that have been described as a large basophilic cell adenocarcinoma associated with the myc transgene, a small eosinophilic cell papillary carcinoma associated with the H-ras transgene, a pale intermediate cell nodular carcinoma associated with the neu transgene, and a papillary adenocarcinoma associated with the int-2 transgene (Cardiff et al., 1993; Cardiff et al., Am. J. Pathol., 139:495–501 (1991); Munn et al., Semin. Cancer Biol., 6:153–158 (1995)).

First-strand cDNA was generated from each of these nine sources of RNA using the cDNA Cycle kit according to the manufacturer's directions (Invitrogen, San Diego, Calif.). These were amplified using degenerate oligonucleotide primers corresponding to conserved regions in kinase catalytic subdomains VIb and IX. The degenerate primers, PTKIa (5'-GGGCCCGGATCCAC(A/C)G(A/G/C/T)GA(C/T)(C/T)-3') SEQID NO:7, and PTKIIa (5'-CCCGGGGAATTCCA(A/T)AGGACCA(G/C)AC(G/A)TC-3') SEQID NO:8, have previously been shown to amplify a conserved 200-bp portion of the catalytic domain of a wide variety of tyrosine kinases (Hanks et al, 1991; Wilks, 1989; Wilks, Methods Enzymol., 200:533–546 (1991)). In an effort to isolate a broad array of protein kinases, two additional degenerate oligonucleotide primers, BSTKIa (5'-GGGCCCGGATCC(G/A)T(A/G)CAC (A/C)G(A/G/C)GAC(C/T)T-3') SEQID NO:9, and BSTKIIa (5'-CCCGGGGAATTCC(A/G)(A/T) A(A/G)CTCCA(G/C) ACATC-3') SEQID NO: 10, were designed for use in this screen. These primers are also directed against subdomains VIb and IX, however, they differ in nucleotide sequence. Restriction sites, underlined in the primer sequences, were generated at the 5' (ApaI and BamHI) and 3' (XmaI and EcoRI) ends of the primer sequences.

Each cDNA source was amplified in three separate PCR reactions using three pairwise combinations of the PTKIa/PTKIIa, BSTKIa/BSTKIIa, and BSTKIa/PTKIIa degenerate primers to amplify first-strand cDNA from each of the nine sources. Following 5-minutes denaturation at 95° C., samples were annealed at 37° C. for 1 min, polymerized at 63° C. for 2 min, and denatured at 95° C. for 30 s for 40 cycles. The resulting ~200-bp PCR products were purified from low-melting agarose (Boehringer Mannheim Biochemicals, Indianapolis, Ind.), ligated into a T-vector (Invitrogen), and transformed in Escherichia coli. Following blue/white color selection, approximately 50 transformants were picked from each of the 27 PCR reactions (3 reactions for each of nine cDNA sources) and were subsequently transferred to gridded plates and replica plated. In total, 1450 transformants were analyzed. Dideoxy sequencing of 100 independent transformants was performed, resulting in the identification of 14 previously described tyrosine kinases.

In order to identify and eliminate additional isolates of these kinases from further consideration, filter lifts representing the 1350 remaining transformants were hybridized individually to radiolabeled DNA probes prepared from each of the 14 initially isolated kinases. Hybridization and washing were performed as described under final washing conditions of 0.13 SSC/0.1% SDS at 70° C. that were demonstrated to prevent cross-hybridization between kinase cDNA inserts (Marquis et al., Nat. Genet., 11:17–26 (1995). In this manner, 887 transformants (70% of the transformants) were identified that contained cDNA inserts from the 14 tyrosine kinases that had initially been isolated. Identifications made by colony hybridization were consistent with those made directly by DNA sequencing.

The remaining 463 transformants were screened by PCR using T7 and SP6 primers to identify those containing cDNA inserts of a length expected for protein kinases. One hundred seventy-two transformants were found to have cDNA inserts between 150 and 300 bp in length. These were subcloned into a plasmid vector and approximately 50 bacterial transformants from each of the 27 PCR reactions were replica plated and screened by a combination of DNA sequencing and colony lift hybridization in order to identify the protein kinase from which each subcloned catalytic domain fragment was derived.

Individual clones were sequenced using the Sequenase version 2 dideoxy chain termination kit (U.S. Biochemical Corp., Cleveland, Ohio). Putative protein kinases were identified by the DFG (aspartate-phenylalanine-glycine) consensus located in catalytic subdomain VI. DNA sequence analysis was performed using MacVector 3.5 (Oxford Molecular Group, Oxford, UK) and the NCBI BLAST server (Atschul et al., J. Mol. Biol., 215:403–410 (1990)).

RNA Preparation and Analysis. RNA was prepared by homogenization of snap-frozen tissue samples or tissue culture cells in guanidinium isothiocyanate supplemented with 7 ml/ml 2-mercaptoethanol, followed by ultra-centrifugation through cesium chloride as previously described (Marquis et al., 1995; Rajan et al., Dev. Biol. 184, 385–401 (1997)). Poly(A)+ RNA was selected using oligo (dT) cellulose (Pharmacia, Piscataway, N.J.), separated on a 1.0% agarose gel (Seakem L E, BioWhittaker Molecular Applications, Rockland, Me.), and passively transferred to a Gene Screen membrane (New England Nuclear, Boston, Mass.). Northern hybridization was performed as described using $^{32}$P-labeled cDNA probes corresponding to catalytic subdomains VI–IX of each protein kinase that were generated by PCR amplification of cloned catalytic domain fragments (Marquis et al., 1995). In all cases calculated transcript sizes were consistent with values reported in the literature.

In Situ Hybridization. In situ hybridization was performed as described (Marquis et al., 1995). Antisense and sense probes were synthesized with the Promega (Madison, Wis.) in vitro transcription system using $^{35}$S-UTP and $^{35}$S-CTP from the T7 and SP6 RNA polymerase promoters of a PCR template containing the sequences used for Northern hybridization analysis.

Discussion of Results. Analysis of the clones resulted in the identification of 33 tyrosine kinases and 8 serine/threonine kinases (Table 1). The 19 receptor tyrosine kinases and 14 cytoplasmic tyrosine kinases that were isolated accounted for all but 33 of the 1056 kinase-containing clones. The remaining clones were derived from 8 serine/threonine kinases, 7 of which were represented by a single clone each, including each of the novel kinases isolated in this screen. Approximately half of the 41 kinases were isolated more than once, and most of these were isolated from more than one tissue or cell line (Table 2 and data not shown). Eight (8) tyrosine kinases, including Jak2, Fgfr1, EphA2, Met, Igflr, Hck, Jak1, and Neu, accounted for 830 (79%) of all clones analyzed (Table 2). Conversely, 18 kinases (44%) were represented by a single clone each, suggesting that further screening of cDNA libraries derived from these tissues and cell lines may yield additional kinases.

TABLE 2

Protein Kinases Isolated from Mammary Glands and Mammary Epithelial Cell Lines.

| Receptor tyrosine kinases | | Nonreceptor tyrosine kinases | | Serine/threonine kinases | |
|---|---|---|---|---|---|
| Axl/Ufo | 6 | c-Abl | 5 | c-Akt1 | 1 |
| EphA2 | 121 | Csk | 46 | Mlkl 1 | 1 |
| EphA7 | 1 | Ctk | 1 | Plk | 26 |
| EphB3 | 2 | c-Fes | 24 | A-Raf | 1 |
| Egfr | 1 | Fyn | 7 | SLK | 1 |
| Fgfr1 | 126 | Hck | 88 | | |
| Flt3 | 1 | Jak1 | 74 | | |
| gflr | 89 | Jak2 | 150 | | |
| InsR | 1 | Lyn | 21 | | |
| c-Kit | 2 | Prkmk3 | 3 | | |
| Met | 120 | c-Src | 23 | Novel kinases | |
| MuSK | 1 | Srm | 1 | Bstk1 | 1 |
| Neu | 62 | Tec | 1 | Bstk2 | 1 |
| Ron | 10 | Tyk2 | 4 | Bstk3 | 1 |
| Ryk | 1 | | | | |
| Tie1 | 1 | | | | |
| Tie2 | 27 | | | | |
| Tyro10 | 2 | | | | |
| Tyro3 | 1 | | | | |

Note. Kinases are arranged by family and class. The number of clones isolated for each kinase is shown on the right.

Three novel protein kinases were identified in this screen, designated Bstk1, 2, and 3. Each of these kinases contains the amino acid motifs characteristic of serine/threonine kinases. Bstk2 and Bstk3 were each isolated from the mammary glands of mice undergoing early postlactational regression. Bstk1 was isolated from a mammary epithelial cell line derived from a tumor that arose in an MMTV-neu transgenic mouse, and is most closely related to the SNF1 family of serine/threonine kinases. A full-length cDNA encoding Bstk1 has subsequently been isolated and identified (Gardner et al., Genomics, 63:46–59 (2000)). Characteristics and expression patterns for the remaining 43 protein kinases isolated by this screen are reported by Chodosh et al., 2000.

EXAMPLE 2

Cloning and Characterization of Hunk

Recognizing the unique temporal and spatial expression pattern of Bstk1, it was renamed Hunk, for hormonally-upregulated, neu-tumor-associated kinase. To isolate the full-length mRNA transcript from which Hunk (Bstk1) was derived, the initial 207-bp RT-PCR product was used to screen a murine brain cDNA library.

Isolation of cDNA Clones Encoding Hunk

Cloning of a Full-Length Hunk cDNA. Poly(A)+ RNA isolated from the MMTV-H-ras transgenic mammary epithelial tumor cell line, AC816 (Morrison, B., et al., Oncogene 9: 3417–3426 (1994)), or from FVB mouse embryos harvested at day 14 of gestation, was used to generate independent cDNA libraries using either the Uni-ZAP (AC816) or the Zap Express (day 14 embryo) lambda phage vector (Stratagene, La Jolla, Calif.) according to the manufacturer's instructions. Hybridization was performed at a concentration of $10^6$ cpm/ml in 48% formamide, 10% dextran sulfate, 4.8× SSC, 20 mM Tris (pH 7.5), 1× Denhardt's solution, 20 µg/ml salmon sperm DNA, and 0.1% SDS at 42° C. overnight. Following hybridization, blots were washed in 2× SSC/0.1% SDS at room temperature (RT) for 30 minutes (×2), followed by 0.2× SSC/0.1% SDS at 50° C. for 20 minutes (×2), and subjected to autoradiography. Positive phage clones were plaque-purified, and plasmids were liberated by in vivo excision according to the manufacturer's instructions (Stratagene,).

Using standard methods and a [α-$^{32}$P]dCTP-labeled random-primed cDNA probe (Random Prime Kit, Boehringer Mannheim Biochemicals), a total of $5 \times 10^5$ plaques were screened from each library. The murine library was screened by a cDNA probe derived from the catalytic domain fragment of Hunk, specifically from the 5' end of the longest clone isolated, G3 (corresponding to nucleotides 618 to 824 of Hunk). The mouse embryo cDNA library was screened using cDNA fragments corresponding to nucleotides 132 to 500 and 276 to 793 of Hunk.

Six (6) additional nonchimeric cDNA clones ranging in length from 4.4 to 5.0 kb were isolated from the mouse embryo library. Each of the clones possessed a poly(A)$^+$ tail and a restriction pattern similar to that of G3 (data not shown).

Sequence analysis. Dideoxy sequencing of the 5' and 3' termini of selected clones, in addition to restriction mapping revealed that all seven cDNA clones were contiguous.

Technically, sequence analyses, including predicted open reading frames and calculation of predicted molecular weights, were performed on an ABI Prism 377 DNA sequencer using MacVector (Oxford Molecular Group, Oxford, UK). Pairwise and multiple sequence alignments of kinase catalytic domains were performed using the ClustalW alignment program (Thompson et al., *Nucleic Acids Research*, 22:4673–4680, 1994) and calculations were made using theBLOSUM series (Henikoff et al., *Proc Natl Acad Sci USA* 89:10915–9, 1992) with an open gap penalty of 10, an extend gap penalty of 0.05, and a delay divergent of 40%. Multiple sequence alignment and phylogenetic calculations were performed using the ClustalX multisequence alignment program (Thompson et al., *Nucleic Acids Research*, 24:4876–4882, 1997) with the same parameters as above.

The longest cDNA clones isolated from each library, G3 and E8, were completely sequenced on both strands. Comparison of the 5024-nucleotide sequence of clone E8 with that of clone G3, revealed that clone E8 contains an additional 40 nucleofides at its 5'-end, and that the length of a poly(T) tract in the 3'-untranslated region (UTR) of the two clones differs by a single nucleotide. There were no additional differences between these two clones.

It was thus determined that clone E8 contained the entire 207-bp RT-PCR fragment, from positions 618 to 824 of Hunk (FIG. 1). The full-length Hunk cDNA sequence (FIG. 1), set forth as SEQID NO:1 (nucleic acid) and SEQID NO:2 (amino acid), respectively, have been deposited with the GenBank data-base (Accession No. AF167987).

The finding that all six cDNA clones (isolated from a cDNA library generated from mRNA containing both 5.1- and 5.6-kb Hunk mRNA species) contained poly(A)$^+$ tails and are co-linear suggested that the 5.6-kb transcript may contain additional 5' or 3' sequence relative to the longest cDNA clone, G3. Consistent with this understanding was the observation that insertions or deletions relative to the Hunk cDNA sequence were not detected using multiple PCR primer pairs to perform RT-PCR on first-strand cDNA prepared from RNA containing both transcripts (data not shown).

Northern Analysis of Hunk mRNA Expression

To determine whether the length of the cDNA clone encoding Hunk is consistent with the size of the Hunk mRNA message, Northern hybridization was performed on poly(A)$^+$ RNA isolated from a Hunk-expressing mammary epithelial cell line (FIG. 2A). FVB mouse embryos were harvested at specified time points following timed matings. Day 0.5 postcoitus was, as above, defined as noon of the day on which a vaginal plug was observed. Tissues used for RNA preparation and protein extracts were harvested from 15- to 16-week-old virgin mice, and snap frozen on dry ice.

RNA was prepared by homogenization of snap-frozen tissue samples or tissue culture cells in guanidinium isothiocyanate supplemented with 7 μl/ml of 2-mercaptoethanol followed by ultracentrifugation through cesium chloride as reported in Example 1. 1 μg poly(A)$^+$ RNA from NAF mammary epithelial cells was selected using oligo(dT) cellulose (Pharmacia), separated on a 0.7% LE agarose gel, and passively transferred to a GeneScreen membrane (NEN), again as in Example 1. Northern hybridization was performed as described using a $^{32}$P-labeled cDNA probe encompassing nucleotides 1149 to 3849 of Hunk generated by random-primed labeling (Boehringer Mannheim Biochemicals) (Marquis et al., 1995). Hybridization was carried out as detailed above for cDNA library screening and the results are shown in FIG. 2A.

This analysis revealed a predominant mRNA transcript 5.1 kb in length in the adult tissue, as well as a less abundant transcript approximately 5.6 kb in length, suggesting that clone E8 may correspond to the shorter Hunk mRNA transcript.

To analyze the spatial and temporal pattern of Hunk mRNA expression during fetal development, as compared with that in adult tissues, Northern hybridization analysis was performed as above, using a the generated Hunk cDNA probe on RNA isolated from FVB mice at embryonic days E6.5, E13.5, and E18.5 (2 μg poly(A)$^+$ RNA samples). Hunk expression was not detected at E6.5, was dramatically up-regulated at E13.5, and was subsequently down-regulated at E18.5 (FIG. 5A).

Similar to the preceding Northern analysis results obtained in adult mammary epithelial cells, analysis of embryonic mRNA revealed Hunk mRNA transcripts approximately 5.1 and 5.6 kb in length. Unlike expression in the mammary epithelial cell line, however, the 5.6-kb Hunk mRNA transcript was more abundant than the 5.1-kb transcript at E13.5, whereas the abundance of the two transcripts was equivalent at E18.5, indicating regulation of the Hunk transcripts in both a developmental stage-specific and a tissue-specific manner.

Detection of Hunk in Mammalian Cells

Figures 4A, 4B:
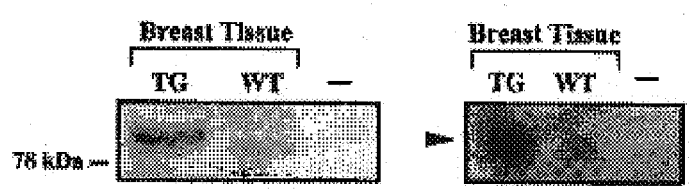
FIGS. 4A and 4B depict the kinase activity associated with the Hunk gene product.

Generation of anti-Hunk antisera. To detect the polypeptide encoded by the Hunk locus, anti-Hunk antisera were raised against recombinant proteins encoding amino-terminal (amino acids 32–213) and carboxyl-terminal (amino acids 556–714) regions of Hunk. 50 μg of protein extract prepared from mammary glands harvested from either MMTV-Hunk transgenic (TG) or wild type (WT) mice, or 100 μg of protein extract prepared from HC11 cells, a mammary epithelial cell line that does not express Hunk mRNA (−), was analyzed by immunoblotting using amino-terminal anti-Hunk antisera (FIG. 4A). FIG. 4B depicts in vitro kinase assay of Hunk immunoprecipitates. Histone H$^+$was used as an in vitro kinase substrate for Hunk protein immunoprecipitated from extracts containing 205 μg of protein, as in FIG. 2B.

GST-Hunk recombinant fusion proteins containing amino-terminal (amino acids 32–213) or carboxyl-terminal (amino acids 556–714) regions of Hunk were expressed in BL21 bacterial cells and purified using glutathione-Sepharose beads according to the manufacturer's instructions (Pharmacia). Following removal of the GST (glutathione-S-transferase) portion by cleavage with Prescission Protease (Pharmacia, Piscataway, N.J.), the liberated carboxyl-terminal Hunk polypeptide was further purified by isolation on a 15% SDS-PAGE gel.

The purified Hunk polypeptides were injected into rabbits (Cocalico Biologicals, Reamstown, Pa.) in cleavage buffer (amino-terminal) or embedded in acrylamide gel slices (carboxyl-terminal). Antisera were affinity-purified on cyanogen bromide-coupled Sepharose columns crosslinked with their respective antigens according to the manufacturer's instructions (Pharmacia). Bound antibodies were then eluted sequentially with 100 mM glycine, pH 2.5, and 100 mM triethyl-amine, pH 11.5, and neutralized with $\frac{1}{10}$ vol of 1.0 M Tris (pH 7.5) (Harlow) et al., *Using Antibodies: A*

Laboratory Manual, Cold Spring Harbor Laboratory Press, Cold Spring Harbor, N.Y. (1999)).

Immunoprecipitation of Hunk/Immunoblotting analysis. To demonstrate that the identified 80-kDa polypeptide corresponded to Hunk, protein extracts prepared from two mammary epithelial cell lines that express Hunk mRNA and from two mammary epithelial cell lines that do not express Hunk mRNA were subjected to immunoprecipitation/immunoblotting protocols (FIG. 2B).

Protein was extracted from tissue culture cells by lysis in EBC buffer for 15 minutes at 4° C. From each extract, 500 µg of protein in 250 µl of EBC was precleared with 40 µl of 1:1 Protein A-Sepharose:PBS (Pharmacia, Piscataway, N.J.) for 3 hours at 4° C. Precleared lysates, prepared from cells that either express (+) or do not express (−) Hunk mRNA, were incubated overnight at 4° C. with affinity-purified antisera raised against the amino-terminus of Hunk (3 µg) (shown in FIG. 2B as α-Hunk IP), the carboxyl-terminus of Hunk (0.1 µg), or polypeptides unrelated to Hunk (0.1 or 3 µg) (shown in FIG. 2B as control IP). Immune complexes were precipitated by incubating with 40 µl of 1:1 Protein A-Sepharose:PBS for 3 hours at 4° C. Complexes were washed twice with PBS, washed once with EBC, and electrophoresed on a 10% SDS-PAGE gel.

Following transfer onto nitrocellulose membranes, immunoblotting was performed. Protein extracts were generated by lysing tissue culture cells or homogenizing murine mammary glands in EBC buffer composed of 50 mM Tris (pH 7.9), 120 mM NaCl, and 0.5% NP-40, supplemented with 1 mM β-glycerol phosphate, 50 mM NaF, 20 µg/ml aprotinin, 100 µg/ml Pefabloc (Boehringer Mannheim Biochemicals), and 10 µg/ml leupeptin. Equivalent amounts of each extract were electrophoresed on 10% SDS-PAGE gels and transferred overnight onto nitrocellulose membranes. Following visualization by Ponceau staining to verify equal protein loading and even transfer, membranes were incubated with blocking solution consisting of 4% dry milk, 0.05% Tween 20, and 1X phosphate-buffered saline (PBS) at RT. Primary antibody incubation with affinity-purified antisera was performed at RT for 1 hour at a final concentration of approximately 2 µg/ml in blocking solution. Following three RT washes in blocking solution, blots were incubated with a 1:10,000 dilution of a horseradish peroxidase-conjugated goat anti-rabbit secondary antibody (Jackson ImmunoResearch, West Grove, Pa.) for 30 minutes at RT. Following three washes in blocking solution and two washes in 1X PBS, blots were developed using the ECL Plus system according to the manufacturer's instructions (Amersham Pharmacia, Piscataway, N.J.) followed by exposure to film.

Figure 2B:
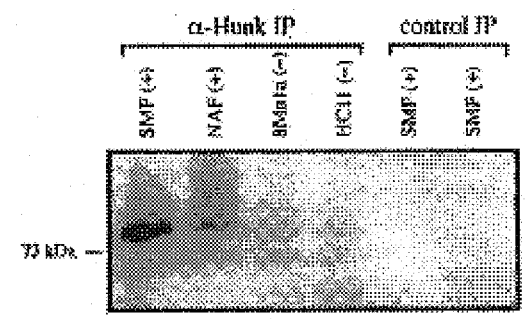

As a result, after immunoprecipitation of Hunk using antisera raised against the amino-terminus of Hunk, followed by immunoblotting with antisera raised against the carboxyl-terminus of Hunk, an 80-kDa polypeptide was identified only in extracts prepared from cells that express Hunk mRNA (FIG. 2B). Similarly, immunoprecipitation of Hunk using antisera raised against the carboxyl-terminus of Hunk, followed by immunoblotting with antisera raised against the amino-terminus of Hunk, also identified an 80-kDa polypeptide only in extracts prepared from cells that express Hunk mRNA, but not in extracts from mammary epithelial cells that do not (FIG. 2C; and data not shown).

The 80-kDa polypeptide was not detected when immunoblotting was performed on immunoprecipitates prepared from Hunk-expressing cells when immunoprecipitation was carried out using either of two control affinity-purified antisera (FIG. 2B; and data not shown). This confirmed that this 80-kDa polypeptide represented the endogenous Hunk gene product in these mammary epithelial cell lines.

In vitro transcription/translation. To confirm that clone E8 encodes the predominant form of Hunk found in mammary epithelial cells, in vitro transcription and translation (IVT) of clone E8 were performed on 1 µg of plasmid DNA using rabbit reticulocyte lysates in the presence of either [$^{35}$S]Met or unlabeled methionine, using either plasmid control (vector) or full-length Hunk cDNA (E8) as a template, according to the manufacturer's instructions (TNT kit, Promega). Completed reactions were electrophoresed on a 10% SDS-PAGE gel along with lysates from Hunk-expressing (+) and non-expressing (−) cell lines, and were subjected either to autoradiography or to immunoblotting using antisera raised against the carboxyl-terminus of Hunk, as described below. This yielded an ~80-kDa labeled polypeptide species, consistent with the 79.6-kDa predicted size of Hunk (data not shown), indicating that the predicted initiation codon at nucleotide 72 is capable of functioning as a translation initiation site.

Figure 2C:
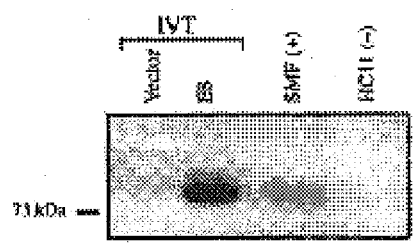

Immunoblotting of protein extracts prepared from the Hunk mRNA-expressing mammary epithelial cell line SMF and from rabbit reticulocyte lysates programmed with sense RNA prepared by in vitro transcription of clone E8 identified a co-migrating 80-kDa polypeptide with the endogenous form of Hunk protein (FIG. 2C). No band was detected in reticulocyte lysates programmed with an empty vector or in whole-cell lysates from a cell line that did not express Hunk mRNA. The observation that the ~80-kDa polypeptide identified by anti-Hunk antisera co-migrated with the polypeptide obtained following in vitro transcription and translation of clone E8 showed that it contains the entire ORF encoding the predominant form of Hunk found in mammary epithelial cells. Nevertheless, due to the absence of in-frame stop codons upstream of the putative translation initiation codon, the possibility that additional 5' coding sequence exists cannot be excluded.

Hunk Encodes a Functional Protein Kinase

Kinase assays. To demonstrate that Hunk protein levels are correlated with kinase activity, in vitro kinase assays were performed. Affinity-purified anti-Hunk antisera were used to immunoprecipitate Hunk from protein extracts prepared from the mammary glands of wild type mice, transgenic mice overexpressing Hunk, or a mammary epithelial cell line that does not express Hunk mRNA.

Transgenic mice were engineered to overexpress Hunk in the mammary gland using the mouse mammary tumor virus LTR to direct Hunk expression. Protein was extracted from snap-frozen lactating murine mammary glands and from 8Ma1a cells (Morrison et al., 1994) by dounce homogenization in EBC buffer containing protease inhibitors, as above. Extracts containing 820 µg protein in 1 ml EBC were precleared with 40 µl 1:1 Protein A-Sepharose:PBS (Pharmacia) for 1 hour at 4° C. One-quarter of the precleared lysate was incubated at 4° C. overnight with 1.2 µg/ml of affinity-purified anti-sera raised against the amino-terminus and carboxyl-terminal of Hunk were used in immunoblotting experiments to detect Hunk in protein extracts prepared from the mammary glands of wildtype mice or MMTV-Hunk transgenic mice harvested at day 9 of lactation (FIG. 4A).

Immune complexes were precipitated with 40 µl of 1:1 Protein A-Sepharose:PBS. In vitro kinase activity of the resulting immunoprecipitates was assayed by incubated with [γ-$^{32}$P]ATP and either histone H1 or myelin basic protein as substrates (FIG. 4B; and data not shown). The final reaction conditions consisted of 20 mM Tris (pH 7.5), 5 mM MgC12, 100 µM dATP, 0.5 µCi/ml [γ-$^{32}$P]ATP, and 0.15 µg/µl histone H1 for 45 minutes at 37° C. Reactions were electrophoresed on a 15% SDS-PAGE gel, and were subjected to autoradiography.

Hunk immunoprecipitates were able to phosphorylate both histone H1 and MBP in vitro. As predicted based on the relative quantities of Hunk immunoprecipitated from transgenic and wild type mammary glands (data not shown), Hunk-associated phosphotransferase activity was substantially greater in immunoprecipitates prepared from transgenic compared to wildtype mammary glands. No activity was observed in immunoprecipitates prepared from a cell line known not to express Hunk mRNA. Thus, these findings demonstrate that anti-Hunk antisera co-immunoprecipitate Hunk and a phosphotransferase, further confirming that Hunk encodes a functional protein kinase.

RNase protection analysis. FIG. 5A depicts an RNase protection analysis of Hunk mRNA spacial expression in tissues of the adult mouse. 30 μg of RNA isolated from the indicated murine tissues was hybridized with antisense RNA probes specific for Hunk and for β-actin. Ribonuclease protection analysis was performed as described (Marquis et al., 1995). Body-labeled anti-sense riboprobes were generated using linearized plasmids containing nucleotides 276 to 500 of the Hunk cDNA and 1142 to 1241 of β-actin (GenBank Accession No. X03672) using [$\alpha$-$^{32}$P]UTP and the Promega in vitro transcription system with T7 polymerase. The β-actin antisense riboprobe was added to each reaction as an internal control. Probes were hybridized with RNA samples at 58° C. overnight in 50% formamide/100 mM Pipes [define] (pH 6.7). Hybridized samples were digested with RNase A and T1, purified, electrophoresed on a 6% denaturing polyacrylamide gel, and subjected to autoradiography.

The spacial distribution of Hunk is summarized in adult tissue in FIG. 6A. High levels of Hunk expression were detected in ovary, thymus, lung, and brain, with modest levels of expression in breast, uterus, liver, kidney, and duodenum. Hunk mRNA expression was very low or undetectable in heart, skeletal muscle, testis, spleen, and stomach.

In situ hybridization. To determine the spatial localization of Hunk mRNA expression during fetal development, $^{35}$S-labeled anti-sense probes were used to perform in situ hybridization on E13.5 and E18.5 embryos (FIGS. 5B–5K). In situ hybridization was performed on FVB embryo tissue sections 15- to 16-week-old virgin mice embedded in OCT compound (as described by Marquis et al., 1995), hybridized with a $^{35}$S-labeled Hunk antisense cDNA probe, see Northern analysis above. Antisense and sense probes were synthesized with the Promega in vitro transcription system using $^{35}$S-UTP and $^{35}$S-CTP from the T7 and SP6 RNA polymerase promoters of a PCR template containing sequences corresponding to nucleotides 276 to 793 of Hunk, a region demonstrated to recognize both mRNA transcripts. Exposure times were 6 weeks in all cases. No signal over background was detected in serial sections hybridized with sense Hunk probes to bowel, fourth ventricle, kidney, liver, lung, lateral ventricle, olfactory epithelium, submandibular gland, skin, stomach, and whisker hair follicle.

Interestingly, Hunk was shown to be expressed in only a subset of cells within each expressing organ. In the duodenum, Hunk is expressed in a subset of epithelial cells located in duodenal crypts, whereas little or no expression is observed in more differentiated epithelial cells of the duodenum or in the mesenchymal compartment of this tissue (FIGS. 6B and 6C). Heterogeneity was also observed among the crypt cells themselves, whereby cells expressing Hunk mRNA at high levels are located adjacent to cells expressing Hunk at substantially lower levels.

Heterogeneous expression patterns were also observed in other tissues. For instance, Hunk mRNA expression in the uterus is restricted to isolated epithelial cells located in mesometrial glands (FIGS. 6D and 6E). Similarly, Hunk expression in the prostate is found within only a subset of ductal epithelial cells (FIGS. 6F and 6G). Hunk expression in the ovary is found principally in the stroma, with little or no expression detected in developing follicles or corpora lutea (FIGS. 6H and 6I). Hunk expression in the thymus is limited primarily to the thymic medulla with lower levels of expression in the thymic capsule (FIGS. 6J and 6K).

Hunk is expressed throughout the brain, with particularly high levels at E13.5 in the cortex, dentate gyrus, and CA1 and CA3 regions of the hippocampus (FIG. 6M), skin, and developing bone, as well as more diffuse expression throughout the embryo. High-power examination also revealed marked heterogeneity in Hunk expression among different cell types in the cerebral cortex (data not shown). As in other tissues, expression in the thymic medulla was markedly heterogeneous (FIG. 5L). Expression of Hunk was more restricted at E18.5, with particularly prominent hybridization in the brain, lung, salivary gland, olfactory epithelium, skin, whisker hair follicles, and kidney. Thus, Hunk is expressed in a variety of tissues of the adult mouse, and expression within these tissues is generally restricted to a subset of cells within a particular compartment or compartments.

Chromosomal Localization; Interspecific mouse backcross mapping. The mouse chromosomal location of Hunk was determined by interspecific backcross analysis using progeny derived from matings of [(C57BL/6J x*M. spretus*) F$_1$ female xC57BL/6J male] mice, as described (Copeland et al., *Trends Genet.* 7:113–118 (1991)). A total of 205 N$_2$ mice were used to map the Hunk locus (see details below).

DNA isolation, restriction enzyme digestion, agarose gel electrophoresis, Southern transfer, and hybridization were performed essentially as described (Jenkins et al., *J. Virol.* 43:26 (1982)). A 520-bp EcoR1 fragment corresponding to nucleotides 276 to 793 of the Hunk cDNA was labeled with [$\alpha$-$^{32}$P]dCTP using a nick-translation labeling kit (Boehringer Mannheim Biochemicals). Washing was performed at a final stringency of 1.0 SSCP/0.1% SDS at 65° C. All blots were prepared with Hybond-N$^+$ nylon membrane (Amersham, Arlington Heights, Ill.).

A major fragment of 6.9 kb was detected in SacI-digested C57BL/6J DNA, and a major fragment of 5.8 kb was detected in SacI-digested *M. spretus* DNA. The presence or absence of the 5.8-kb SacI *M. spretus*-specific fragment was followed in backcross mice. A description of the probes and RFLPs for the loci linked to Hunk, including App, Tiam1, and Erg has been reported previously (Fan et al., *Mol. Cell. Neurosci.*, 7:519 (1996)). Recombination distances were calculated using Map Manager, version 2.6.5 (Manly et al., *Mammalian Genome*, 4:303–313 (1993). Gene order was determined by minimizing the number of recombination events required to explain the allele distribution patterns.

This interspecific backcross mapping panel has been typed for over 2800 loci that are well distributed among all the autosomes as well as the X chromosome (Copeland et al., *Trends Genet.*, 7:113–118 (1991)). C57BL/6J and *M. spretus* DNA samples were digested with several enzymes and analyzed by Southern blot hybridization for informative restriction fragment length polymorphisms (RFLPs) using a mouse Hunk cDNA probe.

The 5.8-kb SacI *M. spretus* RFLP was used to follow the segregation of the Hunk locus in backcross mice. The mapping results indicated that Hunk is located in the distal region of mouse chromosome 16 linked to App, TiamI, and Erg. Although 104 mice were analyzed for every marker and were evaluated by a segregation analysis (not shown), up to 152 mice were typed for some pairs of markers. Each locus was analyzed in pair-wise combinations for recombination frequencies using the additional data. The ratios of the total number of mice exhibiting recombinant chromosomes to the total number of mice analyzed for each pair of loci and the most likely gene order are: centromere-App-4/123-Hunk-0/130-Tiam1-4/152-Erg. The recombination frequencies (expressed as genetic distances in centimorgans (cM) ± the standard error) are -App-3.3±1.6 (Hunk, Tiam1)-2.6±1.3-Erg.

No recombinants were detected between Hunk and Tiam1 in 130 animals typed in common, suggesting that the two loci are within 2.3 cM of each other (upper 95% confidence limit). When the interspecific map of chromosome 16 was compared with a composite mouse linkage map that reports the map location of many uncloned mouse mutations (at http://www.informatics.jax.org/), Hunk mapped in a region of the composite map that lacks mouse mutations (data not shown).

EXAMPLE 3

Developmental Role of Hunk Kinase in Pregnancy-Induced Changes in the Mammary Gland Animal and tissue preparation FVB mice were housed under barrier conditions with a 12-hour light/dark cycle. Mammary glands from pregnant females were harvested at specified time points after timed matings. Day 0.5 was defined as noon of the day on which a vaginal plug was observed. Gestational stage was confirmed by analysis of embryos. Transgenic mothers were housed with wild type mothers immediately after parturition to ensure pup survival and equivalent suckling stimuli. Both transgenic and wild type females were observed to nurse pups.

For experiments involving chronic hormone treatment, adult female FVB mice were subject to bilateral oophorectomy and allowed to recover for two weeks prior to hormonal injections that were administered as previously described (Marquis et al., 1995). For short-term hormone administration experiments, four-month-old virgin female FVB mice were injected subcutaneously with either phosphate buffered saline (PBS) or a combination of 5 mg progesterone in 5% gum arabic and 20 µg of 17b-estradiol in PBS. Four animals from each treatment group were sacrificed 24±1 hours after injection.

Tissues used for RNA analysis were snap frozen on dry ice. Tissues used for in situ hybridization analysis were embedded in OCT compound. For whole mount analysis, number four mammary glands were spread on glass slides and fixed for 24 hours in 10% neutral buffered formalin. Glands were subsequently immersed in 70% ethanol for 15 minutes followed by 15 minutes in deionized water prior to staining in 0.05% Carmine/0.12% aluminum potassium sulfate for 24–48 hours. Glands were dehydrated sequentially in 70%, 90% and 100% ethanol for 10 minutes each, and then cleared in toluene or methyl salicylate overnight.

For histological analysis, mammary glands were fixed as above, and transferred to 70% ethanol prior to paraffin embedding. Sections 5 µm thick were cut and stained with Hematoxylin and Eosin. For BrdU (5-bromodeoxyuridine) analysis of cellular proliferation (Cells: A Laboratory Manual. D. Spector, R. Goldman and L. Leinwand eds. Cold Spring Harbor Laboratory Press, 1998)., animals were injected with 50 µg BrdU per g total bodyweight two hours before sacrifice followed by fixation and paraffin embedding as above.

Generation of MMTV-Hunk transgenic mice.

A full-length cDNA clone, G3, encoding Hunk, was digested with SmaI and SpeI to liberate a 3.2 kb fragment containing the complete coding sequence for Hunk (GenBank Accession number AF167987). This fragment was cloned downstream of the mouse mammary tumor virus long terminal repeat (MMTV LTR) into the multiple cloning site of pBS-MMTV-pA (Gunther, unpublished), which consists of the MMTV LTR upstream of the H-ras leader sequence (Huang et al., Cell, 27:245–255 (1981)) and SV40 splicing and polyadenylation signals. Linearized plasmid DNA was injected into fertilized oocytes harvested from superovulated FVB mice.

Tail-derived DNA was prepared as described (Hogan et al., Cold Spring Harbor, N.Y.: Cold Spring Harbor Laboratory Press (1994)). Mice were genotyped by Southern hybridization analysis and by two independent PCR reactions designed to amplify a region within the SV40 portion of the transgene, and a region spanning the junction between Hunk and SV40 sequences. A portion of the Gapdh (glycelaldehyde-3-phosphate dehydrogenase) locus (GenBank accession No. M32599) was amplified as a positive control for PCR reactions. Oligonucleotide primer sequences were Gapdh F: CTCACTCAAGATTGTCAG-CAATGC (SEQID NO:11); Gapdh B: AGGGTTTCT-TACTCCTTGGAGGC (SEQID NO:12); SV40F: CCT-TAAACGCCTGGTGCTACGC (SEQID NO:13); SV40 B: GCAGTAGCCTCATCATCACTAGATGG (SEQID NO: 14); Hunk F: CTTTCTTTTTCCCCTGACC (SEQID NO:15); PolyA$^+$ B: ACGGTGAGTAGCGTCACG (SEQID NO: 16). Southern hybridization analysis of tail-derived genomic DNA digested with SpeI was performed according to standard methods using a probe specific to the SV40 portion of the transgene.

Four founder mice were identified harboring the MMTV-Hunk transgene in tail-derived DNA that passed the transgene to offspring in a Mendelian fashion. These were screened for transgene expression by Northern hybridization and RNase protection analysis. One founder line, MHK3, was identified that expressed the MMTV-Hunk transgene at high levels. Of note, a subset of transgene-positive MHK3 animals was found not to express the MMTV-Hunk transgene. All MHK3 non-expressing animals were analyzed by Southern hybridization analysis to confirm transgene presence and the expected MHK3-specific integration site.

The tightly regulated expression of Hunk observed in the mammary gland during pregnancy and in response to ovarian hormones indicates that Hunk may play a role in mediating pregnancy-induced changes in the mammary gland. To test this hypothesis, transgenic mice overexpressing Hunk in a mammary-specific fashion were generated using the MMTV LTR. Activity of the MMTV LTR was up-regulated in mammary epithelial cells during pregnancy and lactation in response to rising levels of prolactin, progesterone and glucocorticoids.

Since endogenous Hunk expression is heterogeneous and transiently up-regulated during early pregnancy, MMTV-driven expression of Hunk in transgenic mice was predicted to alter the temporal and spatial profile of Hunk expression in the mammary gland. Accordingly, a cDNA encoding the full-length Hunk protein was cloned downstream of the MMTV LTR and injected into superovulated FVB mice.

Figure 10A:
FIGS. 10A–10E depict MMTV-Hunk transgene expression in MHK3 transgenic mice.
Figure 10B:
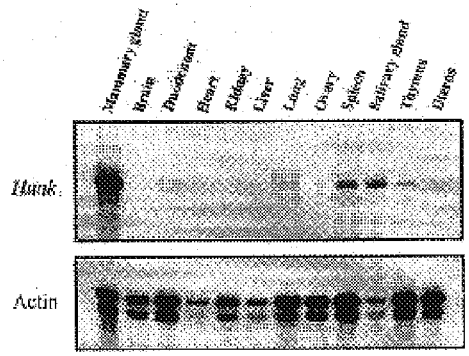

One of the four founder lines, MHK3, was found to express the Hunk transgene at high levels in the mammary gland and was, therefore, studied further (FIG. 10A). The tissue specificity of transgene expression in the MHK3 line was determined by RNase protection analysis, as described in greater detail below, using a transgene-specific probe (FIG. 10B). This analysis confirmed that nulliparous MHK3 transgenic females express high levels of the MMTV-Hunk transgene in the mammary gland and lower but detectable levels of transgene expression in the spleen, salivary gland, lung and thymus, as has been observed for other MMTV transgenic mouse models.

The hormonally responsive nature of the MMTV LTR often results in low levels of expression in the mammary glands of nulliparous transgenic animals and high levels of transgene expression during pregnancy that peak during lactation. In contrast, MHK3 animals express high levels of the MMTV-Hunk transgene in the nulliparous state. In addition, MMTV-Hunk transgene expression levels in mammary glands from pregnant or lactating MHK3 animals were found to vary less than 3-fold relative to nulliparous MHK3 animals, a range of expression that is far less than that typically found in MMTV-based transgenic mouse models (data not shown). Together, these data indicate that MMTV-Hunk transgene expression is high relative to endogenous Hunk expression during all stages of postnatal mammary development.

Figure 10C:
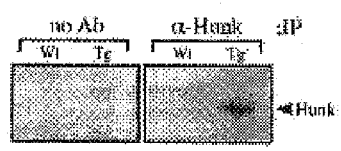

To determine if Hunk mRNA levels in transgenic mice resulted in changes in Hunk protein levels, antisera specific to Hunk were used to analyze Hunk expression levels in extracts prepared from lactating mammary glands of MHK3 transgenic and wild type mice (FIG. 10C).

Protein analysis. Generation of anti-Hunk antisera, immunoblotting and immunoprecipitation were performed, as described in the previous examples. Protein was extracted from mammary glands by dounce homogenization in EBC buffer, also as described in the previous examples. For immunoprecipitation, 500 µg of protein (3 mg/ml) was precleared with 1/10 vol of 1:1 protein A-Sepharose in PBS overnight at 4° C. Precleared lysates were incubated overnight at 4° C. in EBC (50 mM Tris-HCl, pH 7.9; 120 mM NaCl; 0.5% NP40), plus 5% Tween 20 (Bio-Rad, Hercules, Calif.) with or without affinity-purified antisera raised against the C-terminus of Hunk (0.4 µg/ml). Immune complexes were precipitated by incubating with 40 µl of 1:1 protein A-Sepharose in PBS for 1 hour at 4° C. Complexes were washed sequentially with EBC plus 5% Tween 20, EBC (2×), and PBS (2×).

One-fifth of the precipitated complexes were used in an in vitro kinase reaction as previously described in the preceding examples, with 5 µM ATP and 0.5 µg/ml histone H1. The remaining precipitate was electrophoresed on a 10% SDS-PAGE gel, transferred onto a PVDF membrane, and immunoblotted with an antibody against the C-terminus of Hunk, also as described in the preceding examples.

Western analysis of immunoprecipitated Hunk using Hunk-specific antisera revealed increased amounts of Hunk protein in extracts prepared from transgenic when compared with wild type mammary glands (FIG. 10C). The inability to detect Hunk protein in extracts from wild type lactating glands was consistent with the barely detectable levels of endogenous Hunk mRNA expression during this developmental stage (FIG. 7). Conversely, MMTV-Hunk transgene expression was very high during lactation (data not shown).

Figure 10D:
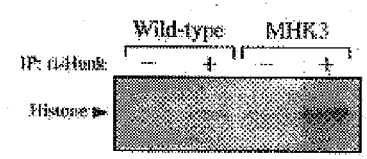

Hunk-associated kinase activity. To demonstrate that Hunk-associated kinase activity is also elevated in MHK3 transgenic animals, in vitro kinase assays were performed. Hunk was immunoprecipitated from protein extracts prepared from the lactating mammary glands of wild type or transgenic mice as above (FIG. 10D). Control immunoprecipitation reactions were carried out in the absence of anti-Hunk antisera. The resulting immunoprecipitates were incubated with $\gamma$-$^{32}$P-ATP and histone H1.

As predicted, based on the relative quantities of Hunk in these extracts, Hunk-associated kinase activity was substantially greater in immunoprecipitates prepared from transgenic when compared with wild type mammary glands, confirming that MHK3 transgenic animals manifest increased levels of both Hunk protein and Hunk-associated kinase activity.

Figure 10E:
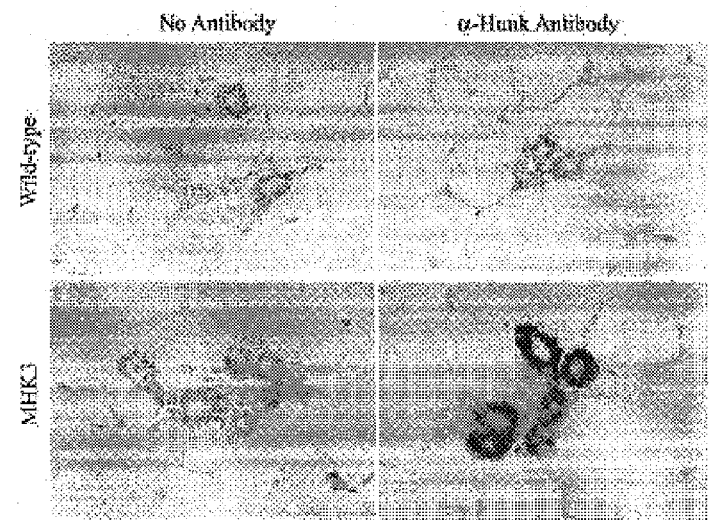

Immunohistochemistry. To investigate the spatial pattern of Hunk protein expression in MHK3 transgenic animals, immunohistochemistry was performed on mammary glands harvested from 14-week old nulliparous transgenic and wild type female mice (FIG. 10E). Mammary glands from nulliparous wild type and MHK3 transgenic females were fixed in 4% paraformaldehyde overnight and transferred to 70% ethanol prior to paraffin embedding. 5 µm sections were dewaxed in xylene and sequentially rehydrated in 100%, 95% and 70% ethanol, followed by PBS. Sections were incubated in Antigen Unmasking Solution (Vector Laboratories, Burlingame, Calif.) for 30 minutes at 100° C., and then transferred to PBS at room temperature (RT). Sections were incubated for 2 hours at RT with antibody raised against the C-terminus of Hunk, washed in PBS (×3), then incubated with 1:500 biotinylated goat anti-rabbit antibody (Vector Laboratories) in 1% BSA/PBS for 30 minutes at RT. After washing in PBS (×3), slides were incubated in a 1:250 dilution of Avidin (Vector Laboratories) for 15 minutes at RT and washed in PBS (3×). NBT and BCIP substrate addition was performed in alkaline phosphate buffer for 3 minutes according to manufacturer instructions (Boehringer Mannheim Biochemicals). Sections were counter-stained for 10 minutes in 0.5% (w/v) Methyl Green in 1.0 M NaOAc (sodium acetate), pH 4.0.

Consistent with high levels of MMTV-Hunk mRNA expression in MHK3 mice, this analysis revealed high levels of Hunk protein expression in transgenic, as compared with wild type mammary glands. As described for other MMTV transgenic models, exogenously expressed Hunk was restricted to the epithelium of MHK3 mice. In addition, Hunk expression in the mammary epithelium of MHK3 animals was found to be relatively homogeneous, unlike the heterogeneous patterns of transgene expression observed in other MMTV transgenic models or the heterogeneous expression of endogenous Hunk mRNA. These data indicate that as compared with wild type animals, MHK3 transgenic animals overexpress Hunk in a mammary epithelial-specific and relatively homogenous manner.

Notably, some MHK3 transgenic animals did not express the MMTV-Hunk transgene. The presence of the MHK3-specific transgene integration site was confirmed by Southern hybridization analysis for all non-expressing MHK3 transgenic mice. A similar type of transgene silencing has been observed in other MMTV transgenic models (Betzl et al., *Biol. Chem.*, 377:711–719 (1996); Stemlicht et al., *Cell*, 98:137–146 (1999)).

Hunk expression is developmentally regulated in the mammary gland

RNase protection analysis. RNase protection analysis was used to determine the temporal pattern of Hunk expression during the postnatal development of the murine mammary gland (FIG. 7A), and to distinguish transgenic from endogenous Hunk expression in MHK3 animals. Mammary glands were harvested from male FVB mice, virgin mice at developmental time points prior to puberty (2 weeks), during puberty (5 weeks) and after puberty (10 weeks and 15 weeks), as well as from mice during early, mid and late pregnancy (day 7, 14 and 20), lactation (day 9), and during postlactational regression (days 2, 7 and 28).

Figure 7A:
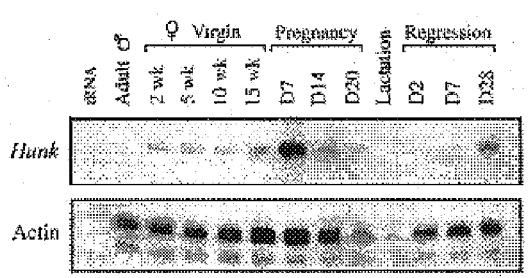
FIGS. 7A–7C depict temporal regulation of Hunk expression during mammary gland development.

Ribonuclease protection analysis was performed, as described in Example 2, using 40 µg samples of total RNA isolated from mammary glands at the indicated time points in FIG. 7A, hybridized to a $^{32}$P-labeled antisense RNA riboprobe spanning the 3'-end of the Hunk cDNA, specific to nucleotides 276–500 of Hunk, the 5'-end of the SV40 polyadenylation signal sequence, and nucleotides 1142–1241 of β-actin added to each reaction as an internal control (GenBank Accession number X03672). RNA preparation, Northern hybridization and labeling of cDNA probes were performed (as described in the previous Examples; Marquis et al., 1995). The $^{32}$P-labeled cDNA probe for Hunk encompassed nucleotides 275 to 793 (GenBank Accession number AF167987). Signal intensities were quantified by phosphorimager analysis (Molecular Dynamics, Sunnyvale, Calif.).

Figure 7B:
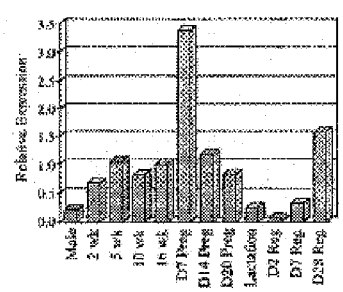

Steady-state levels of Hunk mRNA were shown to be low, and remained relatively constant throughout virgin development. During early pregnancy (day 7), when alveolar buds begin to proliferate rapidly and differentiate, Hunk mRNA levels underwent a dramatic increase and then returned to baseline by mid-pregnancy (FIG. 7A, 7B). The apparent decline in β-actin expression seen by RNase protection analysis during late pregnancy, lactation and early postlactational regression results from a dilutional effect that is due to large-scale expression of genes for milk proteins during late pregnancy and lactation (Buhler et al., Dev. Biol., 155:87–96 (1993); Gavin et al., Mol. Cell. Biol., 12:2418–2423 (1992); Marquis et al., 1995). Quantification and normalized of Hunk expression to β-actin to control for this dilutional effect confirmed that Hunk expression returned to baseline levels by mid-pregnancy, and decreased further during lactation and early postlactational regression (FIG. 7B).

An essentially identical expression profile was observed during pregnancy when Hunk mRNA levels were normalized to cytokeratin 18, an epithelial-specific marker, indicating that developmental changes in Hunk expression are not the result of changes in epithelial cell content in the gland during pregnancy (data not shown).

This conclusion was supported by the finding that Hunk mRNA expression levels decreased from day 7 to day 14 of pregnancy, despite ongoing increases in epithelial cell content that occur during this stage of development. Furthermore, changes in Hunk expression did not appear to be the result of increased cellular proliferation, since the pattern of Hunk expression observed during pregnancy did not correlate with levels of epithelial proliferation that, unlike Hunk expression, remained elevated during mid-pregnancy as graphically shown in FIG. 11B.

In situ hybridization. In order to determine whether the observed pregnancy-induced changes in Hunk mRNA expression levels represent global changes in expression throughout the mammary gland, or changes in expressing subpopulations of cells, in situ hybridization was performed (FIG. 7C, and data not shown), as described in Example 2, using a PCR template containing nucleotides 276 to 793 of Hunk at the time points shown in FIG. 7C. Exposure times were 6 weeks in all cases.

Consistent with the results from RNase protection analysis, in situ hybridization confirmed that Hunk expression in the mammary gland was highest at day 7 of pregnancy and decreased progressively throughout the remainder of pregnancy and lactation. This analysis also revealed that Hunk was expressed exclusively in the epithelium throughout mammary gland development, and that Hunk up-regulation during pregnancy appeared to result from both the up-regulation of Hunk in a subset of cells and an increase in the proportion of Hunk-expressing epithelial cells (FIG. 7C, and data not shown).

Figure 7C:
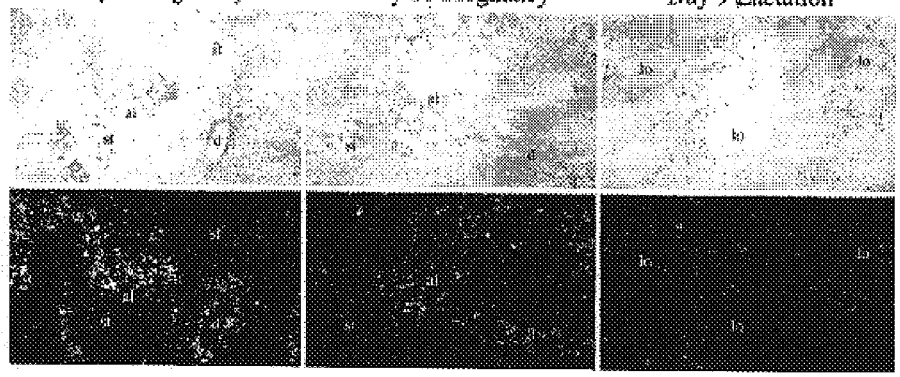
Figure 8A:
FIGS. 8A–8F depict the heterogeneous expression of Hunk in the mammary epithelium as demonstrated by in situ hybridization analysis of Hunk expression in the virgin mammary gland using a $^{35}$S-labeled Hunk-specific antisense probe.
Figure 8B:
Figure 8C:
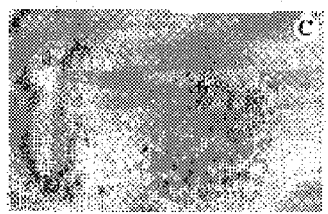
Figure 8D:
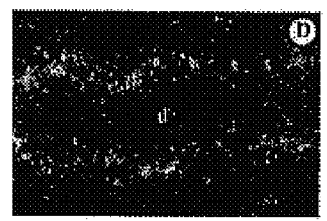
Figure 8E:
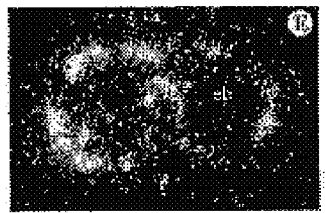
Figure 8F:

The observation that cells that express Hunk at a high level, are found adjacent to non-expressing cells, indicates that, as in other organs of the adult mouse, Hunk expression in the mammary gland is spatially restricted (FIGS. 7C and FIG. 8). This heterogeneous expression pattern is particularly striking in terminal end buds and epithelial ducts of the adolescent gland (FIG. 8), indicating that the murine mammary epithelium is composed of Hunk-expressing and Hunk non-expressing cell types.

Hunk expression is regulated by ovarian hormones

The observation that Hunk mRNA levels increase in the mammary gland during pregnancy, led to an analysis of whether expression of Hunk is modulated by estrogen and progesterone. Oophorectomized FVB 5-week-old nulliparous female mice were treated for fourteen (14) days with 17β-estradiol alone, progesterone alone, or a combination of both hormones. Intact (sham) and oophorectomized, non-hormone treated (OVX) animals were used for comparison.

Figure 9A:
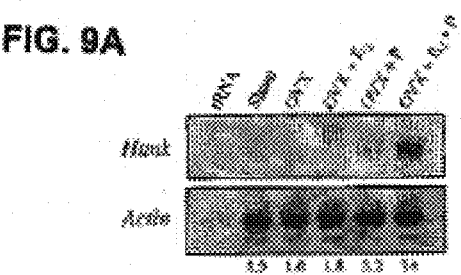
FIGS. 9A–9D show that ovarian hormones alter Hunk mRNA expression in vivo in mammary glands and uteri of mice. Northern blots depict total RNA expression of tissues (mammary glands, FIG. 9A; or uteri, FIG. 9B), harvested from either intact females (sham) or oophorectomized females that received daily subcutaneous injections of either PBS carrier alone (OVX), 17b-estradiol (OVX+$E_2$), progesterone (OVX+P), or both 17b-estradiol and progesterone (OVX+$E_2$+P). Each sample represents a pool of samples hybridized overnight with $^{32}$P-labeled antisense RNA probes specific for Hunk and β-actin. Signal intensities were quantified by phosphorimager analysis and Hunk expression was normalized to β-actin expression levels. Hunk expression relative to expression in oophorectomized (OVX) controls is shown below each lane.

Hunk mRNA levels were quantified by RNase protection analysis, as described above, of samples of total RNA prepared from mammary glands (20 µg) (FIG. 9A) or uteri (40 µg) (FIG. 9B) pooled from at least 10 animals in each experimental group. Hybridization was performed overnight with $^{32}$P-labeled antisense RNA probes specific for Hunk and β-actin. Signal intensities were quantified by phosphorimager analysis, and Hunk expression was normalized to β-actin expression levels. Steady-state Hunk mRNA levels were found to be approximately 4-fold lower in the mammary glands of oophorectomized mice when compared with intact mice, indicating that maintenance of basal levels of Hunk expression in the mammary glands of nulliparous mice requires ovarian hormones (FIG. 9A).

Treatment of oophorectomized animals with 17β-estradiol alone, increased Hunk mRNA expression. But the increase was only to levels below those observed in intact animals. By comparison, treatment with progesterone alone, increased Hunk mRNA expression to levels comparable with those observed in intact animals. In contrast, treatment of oophorectomized animals with both 17β-estradiol and progesterone resulted in a 14-fold increase in the level of Hunk mRNA relative to control oophorectomized animals, and a 3-fold increase relative to intact animals, similar to increases in Hunk expression observed during early pregnancy. These observations indicated that the increase in Hunk mRNA expression observed in the mammary gland during early pregnancy results, either directly or indirectly, from increases in circulating levels of steroid hormones, such as estrogens and progesterone.

Figure 9B:
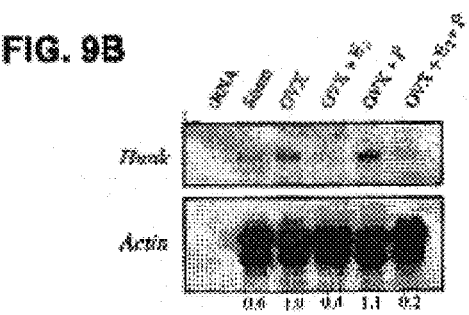

Treatment of mice with ovarian hormones also affected Hunk expression in the uterus (FIG. 9B). Steady-state Hunk mRNA levels were nearly 2-fold higher in oophorectomized animals compared with intact mice suggesting that circulating levels of 17b-estradiol may repress Hunk expression in the uteri of nulliparous mice. Consistent with this suggestion, treatment of oophorectomized animals with 17β-estradiol, either alone or in combination with progesterone, decreased Hunk expression to levels below those observed in either intact or oophorectomized animals.

In contrast to findings in the mammary gland, progesterone treatment had little if any effect on Hunk expression in the uterus. These results indicated that the increase in Hunk mRNA expression observed in the uterus following oophorectomy is due, either directly or indirectly, to loss of tonic inhibition of Hunk expression by estradiol. The observation that the combination of estradiol and progesterone has opposing effects on Hunk expression in the mammary gland and uterus is consistent with the opposing physiological effects of these hormones on proliferation and differentiation in these tissues.

The effects of estradiol and progesterone on Hunk expression in the mammary gland and uterus were confirmed by in situ hybridization analysis performed on tissues from the experimental animals described above (FIG. 9D, and data not shown). Consistent with RNase protection results, oophorectomy resulted in a marked decrease in Hunk mRNA expression in the mammary epithelium and the combination of 17b-estradiol and progesterone resulted in a synergistic increase in Hunk expression. Reminiscent of Hunk expression during early pregnancy, the up-regulation of Hunk mRNA levels in oophorectomized animals treated with a combination of 17b-estradiol and progesterone occurred in a subset of epithelial cells in both ducts and developing alveolar buds.

Since the above experiments involved the chronic administration of hormones, sufficient time elapsed during hormone treatment for significant developmental changes to occur in both the mammary glands and uteri of oophorectomized animals. As such, these experiments do not distinguish whether changes in Hunk expression reflect direct regulation by ovarian hormones, or are a consequence of the changes in epithelial proliferation and differentiation that occur in response to the chronic administration of ovarian hormones.

Figure 9C:
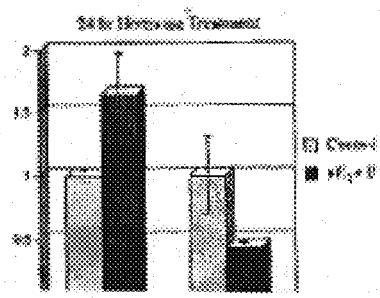
Figure 9:
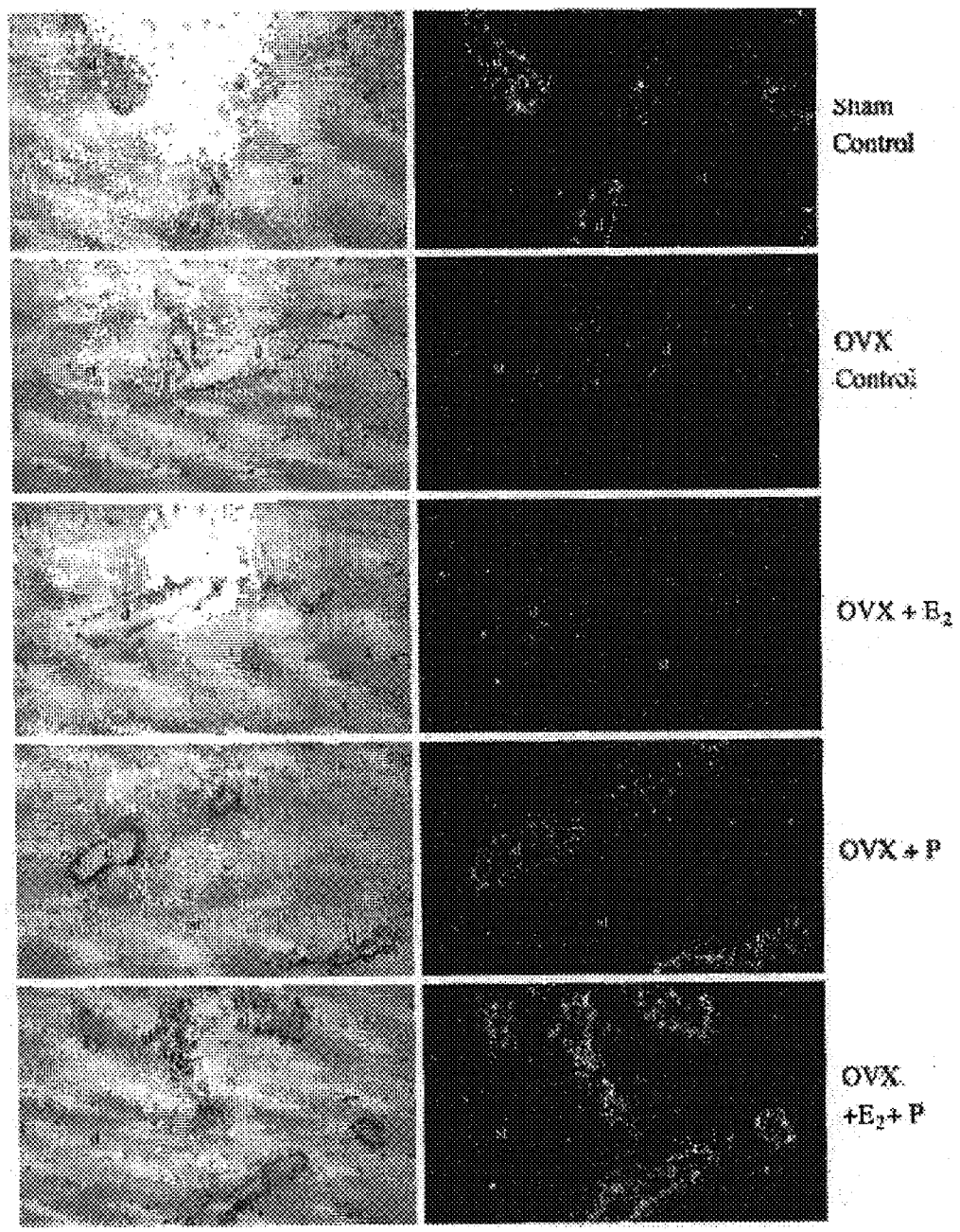

To address this issue, mice were treated with 17b-estradiol, progesterone, or a combination of 5 mg progesterone in 5% gum arabic and 20 μg of 17b-estradiol in PBS. Injection with PBS alone was used as control (FIG. 9C). Analysis of Hunk mRNA expression levels in these mice revealed a pattern similar to that observed in mice treated chronically with hormones. Within 24 hours of the administration of 17b-estradiol and progesterone, steady-state levels of Hunk mRNA increased in the mammary gland, and decreased in the uterus, but the mice treated in such a manner did not develop the marked morphological changes characteristic of long-term hormone administration. (FIG. 9C). Thus, these findings confirmed that the regulation of Hunk expression by estradiol and progesterone is not solely a consequence of changes in mammary and uterine tissue architecture that occur in response to chronic hormone treatment, but rather that the changes appear to result from direct regulation by these hormones.

Hunk overexpression results in impaired lactation

Consonant with the hypothesis that Hunk plays a role in mammary gland development during pregnancy, it was noted that the number of pups successfully reared by MHK3 transgenic females was significantly lower than those of wild type animals. Many of the pups died within 1–2 days of birth, independent of pup genotype. In contrast, offspring of transgenic males mated to wild type females displayed survival rates comparable with those observed for offspring of wild type crosses. These observations suggested that the inability to successfully rear pups was due to a defect in the ability of MHK3 transgenic females to lactate.

To confirm the initial observations regarding reduced RNA content in MHK3 mammary glands, the yield was determined of total RNA (500 μg), isolated from number 3 and number 5 mammary glands harvested from either wild type or MHK3 transgenic females during mammary development at the time points shown in FIG. 11A. The average total RNA yield for each group is represented as the mean ±s.e.m. At least three mice were analyzed from each group.

As expected, in wild type animals, this analysis revealed an approximately 20-fold increase in RNA yield from lactating when compared with nulliparous mammary glands, particularly seen at day 18.5 of pregnancy, and day 2 of lactation (t-test, P=0.047 and 0.0007, respectively). In contrast, the increase in RNA yield over this developmental interval was significantly lower in MHK3 transgenic glands, with the difference between wild type and transgenic glands becoming more pronounced towards late-pregnancy and lactation (wild type versus transgenic, t-test P=0.047 (day 18.5 of pregnancy) and P=0.0007 (day 2 of lactation). In fact, at day 2 of lactation only one third of the total amount of RNA was isolated from transgenic when compared with wild type glands. Non-expressing MHK3 transgenic females exhibited RNA yields that were indistinguishable from wild type animals, indicating that the reduction in RNA observed in MHK3 animals was dependent upon expression of the Hunk transgene (FIG. 11A).

These data suggest impaired mammary development in MHK3 animals during pregnancy and lactation. Consistent with the presence of a lactation defect in MHK3 mice, it was further noted that mammary glands from pregnant or lactating transgenic animals contained lower amounts of RNA as compared with their wild type counterparts. The amount of total RNA isolated from wild type murine mammary glands is highly dependent upon the developmental stage, and can increase almost two orders of magnitude from the nulliparous state to the peak of lactation. The dramatic increase in RNA content during pregnancy and lactation as compared with nulliparous animals is, therefore, due to a combination of increased epithelial cell number and increased milk protein gene expression by individual alveolar epithelial cells.

Hunk overexpression decreases epithelial proliferation during mid-pregnancy

Lobuloalveolar development during pregnancy involves both proliferation and differentiation of alveolar epithelial cells. Alveolar cell proliferation occurs primarily during the first two trimesters of pregnancy, while alveolar differentiation occurs in a graded and progressive manner throughout pregnancy. To determine whether the decrease in RNA yield obtained from MHK3 transgenic glands during pregnancy is related to a decrease in cellular proliferation in these mice, BrdU incorporation rates were compared in epithelial cells from wild type and transgenic mammary glands (FIG. 11B).

Wild type and MHK3 transgenic female mice at different developmental stages were pulse labeled with BrdU before sacrifice. Number 4 mammary glands were harvested from each at day 12.5 and day 18.5 of pregnancy, and day 2 of lactation. At least 3-transgene-expressing mice and 3-wild type mice were analyzed for each time point. The relative percentage of BrdU-positive epithelial cells in the mammary glands of wild type was determined by quantitative analysis of anti-BrdU-stained sections and compared with MHK3 transgenic mice during development (FIG. 11B). Two hours after treatment injections of 50 μg BrdU/g total body weight, the cells were fixed and paraffin embedded. Then paraffin-embedded 5 μm sections were dewaxed as above, pretreated in 2N HCl for 20 minutes at RT, washed in 0.1 M borate buffer, pH 8.5 (×2) and rinsed in PBS. Harvested glands were fixed and stained with Carmine dye in order to visualize epithelial ducts and alveoli. BrdU immunohistochemistry was performed using the Vectastain Elite ABC Kit (Vector Laboratories), rat anti-BrdU IgG (Vector Laboratories), and a secondary biotinylated rabbit anti-rat IgG antibody, according to manufacturer instructions. Sections were counter-stained with Methyl Green as described above.

BrdU incorporation was detected using an anti-BrdU antibody followed by ABC detection method (Vector Laboratories). The percentage of BrdU-positive epithelial cells was determined after normalizing nuclear area to the average nuclear size of either BrdU positive or negative cells. The fraction of BrdU-positive and negative nuclei in the epithelial cells was quantified by color segmentation analysis of digitally captured images using Image-Pro Plus software (Media Cybernetics LP, Silver Spring, Md.). At least four different fields/animal, and 3-animals/time point were analyzed for BrdU incorporation. A significant difference in the fraction of BrdU-positive cells was observed between wild type and transgenic mammary glands only at day 12.5 of pregnancy (t-test, P=0.004).

As predicted based upon the similar morphology of wild type and transgenic mammary glands in nulliparous animals (data not shown), no significant difference in the percentage of BrdU-positive cells was observed between wild type and transgene-expressing mammary glands harvested from nulliparous animals.

Moreover, a dramatic increase in epithelial proliferation was observed at day 6.5 of pregnancy both in wild type and transgenic animals relative to nulliparous females. In contrast, at day 12.5 of pregnancy, epithelial proliferation rates remained high in wild type glands, but dropped markedly in glands from MHK3 animals (wild type versus transgenic at day 12.5, t-test, P=0.004). By comparison, no differences in epithelial proliferation rates were observed between wild type and transgenic glands at day 18.5 of pregnancy. Furthermore, no differences in apoptosis rates were observed between wild type and MHK3 transgenic glands during virgin development, pregnancy or lactation, as evidenced by similar levels of TUNEL-positive cells (data not shown). Since MMTV-Hunk transgene expression levels in MHK3 animals are roughly comparable in the mammary gland throughout pregnancy and do not coincide with the observed defect in proliferation, it was concluded that Hunk overexpression inhibits mammary epithelial proliferation specifically during mid-pregnancy.

Hunk overexpression impairs lobuloalveolar development

The finding above, of increased pup death among offspring of MHK3 females, when taken together with the decreased RNA content of mammary glands from lactating MHK3 animals, suggested that MHK3 female glands may have a defect in lobuloalveolar development. To address this hypothesis directly, MHK3 transgenic females were sacrificed at different stages of pregnancy and lactation for morphological analysis. However, analysis of both whole mounts and Hematoxylin and Eosin stained sections at day 6.5 and day 12.5 of pregnancy revealed no obvious morphological differences between the mammary glands of wild type and MHK3 transgenic animals, despite the fact that epithelial cell proliferation is markedly impaired in MHK3 female mice at day 12.5 of pregnancy (FIG. 11B, FIG. 12, and data not shown).

In contrast, marked morphological differences were observed between wild type and transgenic animals at day 18.5 of pregnancy. Analysis of whole mounts and Hematoxylin and Eosin stained sections at this stage of development consistently showed decreased lobuloalveolar development in MHK3 transgenic animals (FIG. 12). In addition to their larger size, alveoli in wild type mice at day 18.5 of pregnancy contained copious amounts of lipid, whereas those of MHK3 mice did not.

Figure 12A:
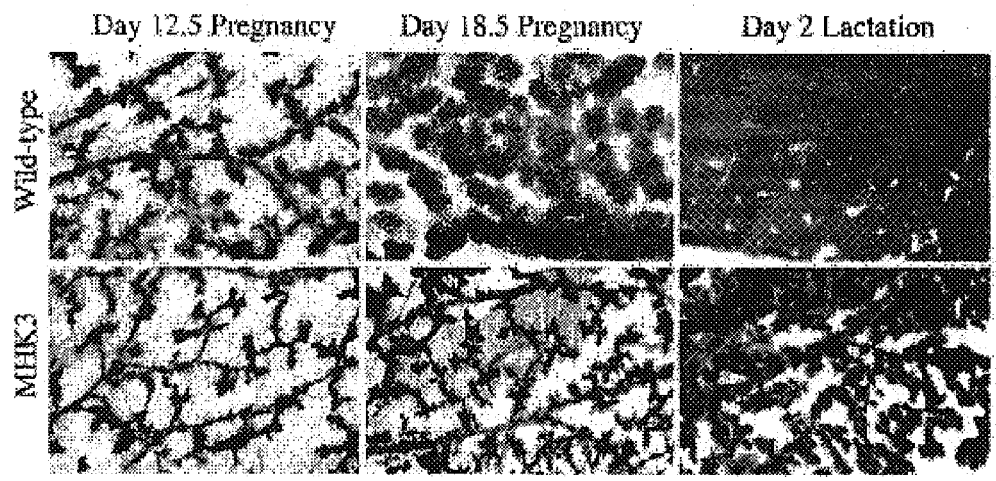
FIGS. 12A and 12B depict morphological defects in MHK3 transgenic mice during late pregnancy and lactation. Mammary glands from MHK3 transgenic and wild type females were harvested at day 12.5 and day 18.5 of pregnancy, and day 2 of lactation. At least 3-transgene-expressing mice and 3-wild type mice were analyzed for each time point. A representative photomicrograph is shown for each group.
Figure 12B:
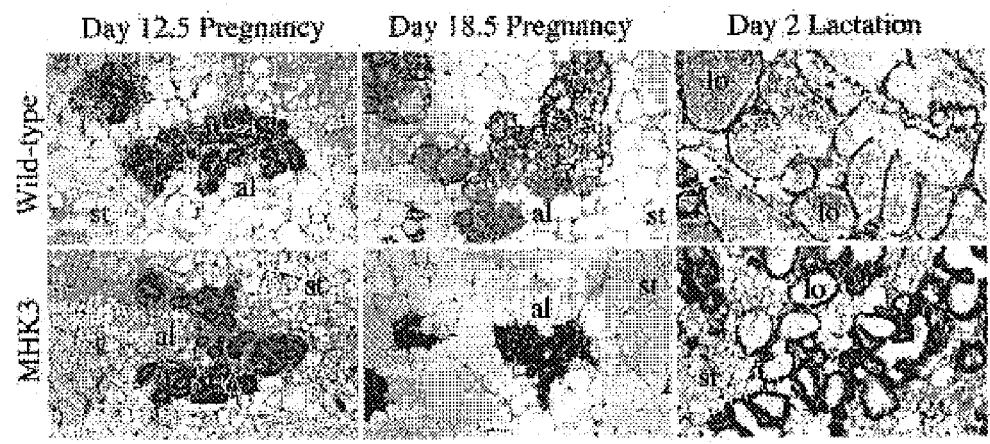

In addition to the abnormalities observed at day 18.5 of pregnancy, decreased lobuloalveolar development was also observed in MHK3 females at day 2 of lactation. Normally during lactation the mammary gland is filled with casein-secreting lobules, such that by whole-mount analysis the gland is entirely opaque, and by histological analysis no white adipose tissue is seen (FIG. 12). In contrast, lobuloalveolar units in lactating Hunk-overexpressing transgenic animals were smaller, and appeared less developed by whole-mount analysis as compared with wild type and non-expressing MHK3 females (FIG. 12A, and data not shown). Consequently, only half of the mammary fat pad of lactating MHK3 mice was occupied by secretory alveoli (FIG. 12B).

While this may be due in part to decreased epithelial cell proliferation observed during mid-pregnancy, morphometric analysis of Hematoxylin and Eosin stained sections from MHK3 mice at day 18.5 of pregnancy, and day 2 of lactation, revealed that compared with their wild type counterparts, the mammary glands of MHK3 animals consist of a normal number of alveoli that are uniformly smaller and less differentiated morphologically. They do not contain a smaller number of morphologically normal alveoli. (FIG. 12B, and data not shown). Moreover, alveoli in lactating transgenic animals were less distended with milk when compared with wild type glands. In contrast, similar analyses performed on the mammary glands of non-expressing MHK3 transgenic animals during lactation revealed no morphological defects (data not shown). These observations indicate that dysregulated expression of Hunk impairs terminal differentiation of the mammary gland during late pregnancy and lactation in a manner potentially distinct from the observed defect in epithelial proliferation.

Hunk overexpression inhibits mammary epithelial differentiation

The dramatic changes in epithelial differentiation that occur in the mammary gland during lobuloalveolar development are reflected on a molecular level by the tightly regulated and temporally ordered expression of genes for milk proteins (Robinson et al., *Development* 121:2079–2090 (1995)). While steady-state mRNA levels for each of these genes typically increase throughout pregnancy, each gene undergoes a maximal increase in expression at a characteristic time during pregnancy. These differential expression profiles permit individual genes to be classified as early (β-casein), intermediate (κ-casein, lactoferrin), late-intermediate (WAP, whey acidic protein), or late (ε-casein) markers of mammary epithelial differentiation (Robinson et al., 1995; D'Cruz, unpublished). As such, the expression of these genes can be used as a molecular correlate for the extent of mammary epithelial differentiation. Accordingly, analysis of temporal expression patterns of milk protein genes permits the degree of lobuloalveolar differentiation to be reproducibly and objectively determined at the molecular level.

To confirm that the defect in lobuloalveolar development observed in MHK3 transgenic mice included a defect in differentiation, and was not simply a consequence of reduced epithelial cell numbers, the expression of a panel of molecular differentiation markers was examined in wild type and MHk3 animals during lobuloalveolar development. Probes for milk protein gene expression were: β-casein, nucleotides 181–719 (GenBank Accession number X04490); κ-casein, nucleotides 125–661 (GenBank Accession number M 10114); lactoferrin, nucleotides 993–2065 (GenBank Accession number D88510); WAP, nucleotides 131–483 (GenBank Accession number X01158), and ε-casein, nucleotides 83–637 (GenBank Accession number V00740).

If the defect in lobuloalveolar development was solely due to reduced epithelial cell mass, then the absolute level of expression of milk protein genes in MHK3 animals should be similar to that observed in wild type animals when normalized for epithelial content. Similarly, if alveolar cells present in MHK3 glands differentiate normally during pregnancy, then the levels of expression of early, mid and late differentiation markers relative to each other should be similar to that observed in wild type animals. As such, the observation that the absolute levels of expression of multiple differentiation markers are reduced despite normalizing for epithelial content, or that the expression of these differentiation markers relative to each other is altered compared to wild type animals, would indicate that mammary epithelial differentiation is impaired in MHK3 animals and is independent of the observed proliferation defect.

To determine whether MHK3 animals manifest a defect in differentiation in addition to the defect in proliferation demonstrated above, mRNA expression levels were determined at day 6.5 of pregnancy (FIG. 13A), day 12.5 of pregnancy (FIG. 13B), day 18.5 of pregnancy (FIG. 13C) or at day 2 of lactation (FIG. 13D), for a panel of early (β-casein), intermediate (κ-casein, lactoferrin), late intermediate (WAP), and late (ε-casein) markers of mammary epithelial differentiation in mammary glands from transgenic and wild type animals.

Although few if any morphological differences were noted in transgenic mice before day 18.5 of pregnancy, when normalized to ε-actin expression, steady-state levels of expression for all five milk protein genes were reduced in mammary glands from MHK3 transgenic mice compared with wild type mice, beginning as early as day 6.5 of pregnancy and persisting throughout pregnancy and into lactation. In contrast, expression levels of the epithelial cell marker, cytokeratin 18, did not differ significantly between wild type and transgenic glands at any stage of pregnancy or lactation when normalized to β-actin expression (FIG. 13). Although β-actin levels did not change significantly on a per cell basis during pregnancy and lactation, the enormous contribution of the expression of milk protein genes to the total RNA pool results in an apparent decrease in the expression of reference genes when comparing equal amounts of total RNA (FIGS. 7 and 13). The magnitude of this dilutional effect correlated with the differentiation state of the mammary gland. Thus, the lower levels of expression of milk protein genes observed in the less differentiated MHK3 glands results in a less severe dilutional effect and apparent increases in β-actin and cytokeratin 18 expression in the mammary glands of MHK3 animals, as compared with wild type animals at day 18 of pregnancy, and day 2 of lactation. Therefore, in aggregate our findings indicate that the reduced expression of differentiation markers in MHK3 animals during pregnancy and lactation is not simply due to a reduction in epithelial cell content and suggests that mammary glands from Hunk-overexpressing transgenic mice are less differentiated than wild type glands at each stage of lobuloalveolar development.

Figure 14:
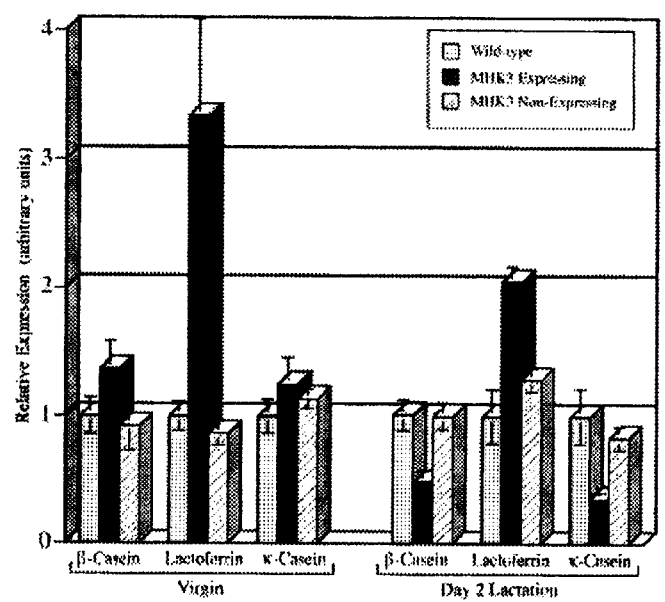
FIG. 14 graphically depicts up-regulation of lactoferrin expression at specific developmental stages in MHK3 mammary glands. Analysis of differentiation marker expression in mammary glands from either wild type (light-shaded boxes), MHK3 transgene-expressing (dark-shaded boxes), or non-expressing MHK3 transgenic (hatched boxes) female mice during puberty or day 2 of lactation, as described in FIG. 13. Northern hybridization analysis and quantification was performed on virgin or day 2 lactating mice. Total RNA was isolated from mammary glands using $^{32}$P-labeled cDNA probes specific for milk protein genes, as indicated. Expression of these genes was normalized to that of β-actin. Wild type expression values were set to 1.0 and are represented as the mean ±s.e.m. for each group.

As further controls for these experiments, expression of milk protein genes was analyzed in non-expressing MHK3 transgenic females at day 2 of lactation (FIGS. 13 and 14, and data not shown). No differences in the expression either of cytokeratin 18 or of alveolar differentiation markers were observed between non-expressing MHK3 glands and glands from wild type mice, consistent with the lack of morphological or functional defects in non-expressing MHK3 glands.

FIG. 13E summarizes a multivariate regression analysis of expression products shown in FIGS. 13A–13D, demonstrating the effects of transgene expression and developmental stage on the natural logarithm of cytokeratin 18 and expression levels of milk protein genes. All expression levels were normalized to β-actin. The average effect of transgene expression (Effect) on the expression of each milk protein gene is represented as the natural logarithm of the average fold-difference between transgenic and wild type values. The respective P value (significance of transgene effect) is shown for each milk protein gene. Notably, the transgene expression had no effect on cytokeratin 18 expression, and resulted in an average decrease in the expression levels of differentiation markers ranging from 2.0-fold (β-casein) to 6.5-fold (ε-casein). The $R^2$ value represents the degree to which the difference in the observed data from the null hypothesis is due to transgene expression. The P value for the significance of the regression model was <0.01 for all differentiation markers shown.

Northern analyses of expression products shown in FIGS. 13A–13D were quantified by phosphorimager quantification methods (as described in the previous Examples; Marquis et al., 1995)(see FIG. 13F). As above, the $^{32}$P-labeled cDNA probe for Hunk encompassed nucleotides 275 to 793 (GenBank Accession number AF167987). The number of mice analyzed in each group were: 4 Wt, 5 Tg (d6.5); 3 Wt, 3 Tg (d12.5 and d18.5); and 4 Wt, 4 Tg, 4 non-expressing Tg (d2 Lact). Together, these findings strongly suggested that the abnormalities in mammary epithelial differentiation observed in MHK3 mice are due to MMTV-Hunk transgene expression, rather than to site-specific integration effects, such as the insertional disruption of an endogenous gene.

To further analyze the impact of MMTV-Hunk transgene expression on lobuloalveolar development, a multivariate regression analysis was performed on the above normalized gene expression data to quantitate the effects of transgene expression on mammary epithelial differentiation during a developmental interval from day 6.5 of pregnancy to day 2 of lactation (FIG. 13E, 13F). This analysis revealed that the expression of four epithelial differentiation markers, β-casein, κ-casein, WAP, and ε-casein, was significantly lower in the mammary glands of transgenic animals compared with wild type animals across all developmental time points.

No differences were observed in cytokeratin 18 expression between wild type and transgenic glands, confirming that normalization to β-actin expression was sufficient to control for differences in epithelial cell content. These results indicated that the mammary glands of MHK3 animals were significantly less differentiated than wild type glands throughout pregnancy and into lactation.

Interestingly, the average reductions in mRNA expression levels observed for the late differentiation marker, ε-casein (Tg effect=−1.87; 6.5-fold), and the late-intermediate differentiation marker, WAP (Tg effect=−1.53; 4.6-fold), were considerably more pronounced than the reductions in expression observed for the early differentiation marker, β-casein (Tg effect=−0.70; 2.0-fold), and the intermediate differentiation marker, κ-casein (Tg effect=−0.94; 2.6-fold) (FIG. 13). The observation that transgene expression had a greater effect on the expression of late differentiation markers compared with early differentiation markers indicated that late events in mammary epithelial differentiation are disproportionately affected during lobuloalveolar development in MHK3 mice. This finding was consistent with the morphological defects observed in these mice during late pregnancy.

Hunk upregulates lactoferrin expression in MHK3 mice

Surprisingly, while the expression of all 5 epithelial differentiation markers examined was reduced in the mammary glands of MHK3 transgenic animals throughout pregnancy, expression of the gene for lactoferrin was actually higher in transgenic animals compared with wild type animals at day 2 of lactation (FIGS. 13D and 14). This finding led to an analysis of the impact of Hunk overexpression on lactoferrin expression in nulliparous MHK3 mice. Sample sizes were 16, 10 and 8 animals, respectively, for adolescent mice, and 4 animals per group for lactation points. Northern hybridization analysis and quantification was performed, as above, on 3 µg (virgin) or 5 µg (day 2 lactation) total RNA, isolated from mammary glands using $^{32}$P-labeled cDNA probes specific for milk protein genes as indicated in FIG. 14.

Consistent with results obtained in lactating MHK3 animals, steady-state levels of lactoferrin mRNA were significantly higher in the mammary glands of nulliparous MHK3 expressing transgenic animals compared with either non-expressing MHK3 transgenic animals or age-matched nulliparous wild type animals, after normalization to β-actin (FIG. 14). This effect was surprising. Therefore to determine whether the effects of Hunk overexpression on lactoferrin expression may be more specific than the generally inhibited mammary epithelial differentiation that results from Hunk overexpression during pregnancy and lactation, gene expression patterns were compared in wild type and MHK3 nulliparous transgenic glands using oligonucleotide-based cDNA microarrays. These microarray studies revealed that, of the approximately 5500 genes analyzed, the gene for lactoferrin is one of only 16 genes whose expression changes by more than 2.5-fold in transgenic animals, when compared with wild type glands. As noted above, the mammary glands of nulliparous MHK3 animals are morphologically indistinguishable from those of wild type littermates. Thus, the data indicate that the effects of Hunk overexpression on lactoferrin gene regulation are relatively specific, and are unlikely to be secondary to marked abnormalities in mammary gland morphology or to global changes in gene expression.

In contrast to lactoferrin, mRNA expression levels of the epithelial differentiation markers, β-casein, κ-casein, α-lactalbumin (Lalba—Mouse Genome Informatics,), WDNM1 (Expi—Mouse Genome Informatics), and WAP, in adolescent nulliparous females, were not significantly affected by Hunk overexpression (FIG. 14, and data not shown). Consistent with this finding, the rate of ductal elongation and extent of epithelial side-branching in mammary glands from 5- to 6-week-old nulliparous transgenic mice was comparable with that observed in wild type mice, as analyzed by whole-mount and histological analysis (data not shown). These observations indicated that Hunk does not cause precocious differentiation of the mammary gland during puberty, but may specifically activate pathways resulting in lactoferrin upregulation. Similarly, the observation that lactoferrin expression is up-regulated in the mammary glands of lactating MHK3 animals, despite the global inhibitory effect of Hunk overexpression on mammary epithelial differentiation during late pregnancy and lactation, confirmed the conclusion that the effects of Hunk on lactoferrin expression are distinct from those on mammary epithelial differentiation.

Finally, as shown, the treatment of mice with 17β-estradiol and progesterone results in the rapid and synergistic up-regulation of Hunk expression in the mammary gland, indicating that the up-regulation of Hunk expression in response to hormones is not a consequence of the marked changes in epithelial differentiation or epithelial cell number that occur either during early pregnancy or in response to the chronic administration of 17β-estradiol and progesterone. Interestingly, unlike the effect of steroid hormones on Hunk expression in the mammary gland, treatment of mice with 17β-estradiol either alone or in combination with progesterone results in down-regulation of Hunk expression in the uterus. The opposing effects of combined estradiol and progesterone treatment on Hunk expression in the mammary gland and uterus is reminiscent of the dichotomous effects of these hormones on epithelial proliferation in these tissues. As such, the data shows that the effect of steroid hormones on Hunk expression in the mammary gland and uterus parallels the dichotomous response of these tissues to estradiol and progesterone, thus providing additional support for the role of Hunk as a downstream effector of estrogen and progesterone, and offers an explanation for the dichotomous response of these tissues to steroid hormones.

EXAMPLE 5

HUNK Expression in Human Primary Ovarian and Colon Tumors

To investigate the potential involvement of HUNK, or a cell type in which HUNK is expressed, in human breast, ovarian and colon carcinogenesis, HUNK expression levels were determined in a panel of human primary breast, ovarian and colon cancers along with benign tissue samples from each of these organs. An RNase protection analysis was performed, as above, using 30 µg of total RNA isolated from tumors hybridized with a $^{32}$P-labeled antisense riboprobe specific for HUNK or for β-actin. As a negative control, tRNA was used for comparison.

RNA was isolated from 6 benign breast tissue samples and from 46 primary breast tumors obtained after surgery. An RNase protection analysis was performed using 10 µg of total RNA hybridized with a $^{32}$P-labeled antisense riboprobe specific for HUNK, cytokeratin 18 (CK18) or for β-actin. HUNK and β-actin expression levels were quantified by phosphorimager analysis, and HUNK expression levels were normalized to either CK18 or β-actin for each sample. HUNK expression levels in breast tumors were compared with benign tissue. Normalized HUNK expression levels in the benign tissues was set equal to 1.0. This analysis demonstrated that among all breast tumors, HUNK is expressed at a level that is 2.2-fold lower than in benign ovarian tissue. Moreover, when analyzed by subsets, 76% of all breast tumors were found to exhibit HUNK expression levels that were 5.0-fold lower than the average HUNK expression levels observed in benign tissue. Further analysis of HUNK expression as a function of breast tumor grade revealed that HUNK expression correlates negatively with tumor grade with poorly-differentiated (p=0.036) and moderately-differentiated (p=0.0029) tumors exhibiting lower levels of HUNK expression than benign tissues. Finally, expression of HUNK was also found to be decreased in both ductal carcinomas and lobular carcinomas.

In a similar manner, RNA was isolated from 16 benign ovarian tissue samples and from 22 primary ovarian tumors obtained after surgery. An RNase protection analysis was performed using 10 µg of total RNA hybridized with a $^{32}$P-labeled antisense riboprobe specific for HUNK or for β-actin. HUNK and β-actin expression levels were quantified by phosphorimager analysis, and HUNK expression levels were normalized to βactin for each sample. HUNK expression levels in ovarian tumors were compared with benign tissue. Normalized HUNK expression levels in the benign tissues was set equal to 1.0. This analysis demonstrated that HUNK is expressed in ovarian tumors at a level that is 10.3-fold higher than in benign ovarian tissue (p=0.0000034). Further analysis of HUNK expression as a function of ovarian tumor grade revealed that HUNK expression correlates positively with tumor grade with poorly-differentiated tumors and moderately-differentiated tumors exhibiting higher levels of HUNK expression than well-differentiated tumors.

Finally, RNA was isolated from 17 benign colon tissue samples and from 24 paired primary colon tumors obtained after surgery (e.g., benign samples were taken from the same patient as the tumor samples). An RNase protection analysis was performed using 10 µg of total RNA hybridized with a $^{32}$P-labeled antisense riboprobe specific for HUNK or for β-actin. HUNK and β-actin expression levels were quantified by phosphorimager analysis, and HUNK expression levels were normalized to β-actin for each sample. HUNK expression levels in colon tumors were compared with benign tissue. Normalized HUNK expression levels in the benign tissues was set equal to 1.0. This analysis demonstrated that HUNK is expressed in colon tumors at a level that is 1.9-fold higher than in benign colon tissue (p=0.035). Notably, this elevated level of expression of HUNK in colon tumors was primarily due to the massive overexpression of HUNK in a subset of colon tumors. Specifically, 4 tumors exhibited expression levels that were greater than 10 standard deviations from the mean of benign tissues. Finally, expression of the HUNK kinase has been shown to be increased in a subset of human colon carcinomas compared to benign tissue, and to be positively associated with tumor grade.

Each and every patent, patent application and publication that is cited in the foregoing specification is herein incorporated by reference in its entirety.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention. Such modifications, equivalent variations and additional embodiments are also intended to fall within the scope of the appended claims.

What is claimed is:

1. An isolated nucleotide sequence comprising the nucleotide sequence set forth in SEQID No: 1.

2. The isolated nucleotide sequence of claim 1, consisting of the nucleotide sequence set forth in SEQID No: 1.

3. A recombinant cell comprising the isolated nucleic acid of claim 1.

4. A vector comprising the isolated nucleic acid of claim 1.

5. An isolated nucleic acid sequence comprising a sequence complementary to all of the nucleic acid sequence of claim 1.

6. A mammalian cell comprising the isolated nucleic acid according to claim 5.

7. The isolated nucleic acid of claim 1, further comprising a reporter gene operably fused thereto, or a fragment thereof having reporter activity.

* * * * *